(12) United States Patent
Kranich et al.

(10) Patent No.: US 8,367,677 B2
(45) Date of Patent: *Feb. 5, 2013

(54) NON-GLYCOSYLATED/NON-GLYCOSIDIC/NON-PEPTIDIC SMALL MOLECULE PSGL-1 MIMETICS FOR THE TREATMENT OF INFLAMMATORY DISORDERS

(75) Inventors: Remo Kranich, Berlin (DE); Ewald Mirko Aydt, Berlin (DE)

(73) Assignee: Revotar Biopharmaceuticals AG, Henningsdorf (DE)

( * ) Notice: Subject to any disclaimer, the term of this patent is extended or adjusted under 35 U.S.C. 154(b) by 206 days.

This patent is subject to a terminal disclaimer.

(21) Appl. No.: 10/593,259
(22) PCT Filed: Mar. 18, 2005
(86) PCT No.: PCT/EP2005/002920
§ 371 (c)(1), (2), (4) Date: Jul. 26, 2007
(87) PCT Pub. No.: WO2005/090284
PCT Pub. Date: Sep. 29, 2005

(65) Prior Publication Data
US 2008/0249107 A1    Oct. 9, 2008

(30) Foreign Application Priority Data
Mar. 18, 2004 (EP) .................................... 04006461

(51) Int. Cl.
A61K 31/49    (2006.01)
(52) U.S. Cl. ............... 514/255.01; 514/563; 514/438; 514/535; 514/471; 544/391; 560/43; 549/486; 549/76; 562/457
(58) Field of Classification Search ............ 510/386; 548/339.1; 514/183, 255, 563, 438, 391, 514/43, 535, 471; 549/486, 76; 562/457
See application file for complete search history.

(56) References Cited

U.S. PATENT DOCUMENTS
4,363,813 A    12/1982    Kawasaki et al.
(Continued)

FOREIGN PATENT DOCUMENTS
EP    0217204 A1    4/1987
(Continued)

OTHER PUBLICATIONS

Blaakmeer et al. (Structure-Activity relationship of isolated avenanthramide alkaloids and synthesized related compounds as oviposition deterrents for *Pieris brassicae*, Journal of Natural Products, vol. 57, No. 8, pp. 1145-1151, Aug. 1994).*

(Continued)

*Primary Examiner* — Brandon Fetterolf
*Assistant Examiner* — Jean Cornet
(74) *Attorney, Agent, or Firm* — J.A. Lindeman & Co., PLLC

(57) ABSTRACT

Pharmaceutical compositions comprising at least one compound of the formulas (Ia) or (Ib) and a pharmaceutically acceptable carrier which is useful in a medicine

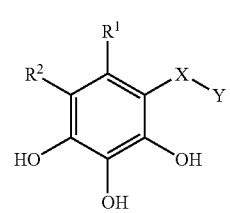

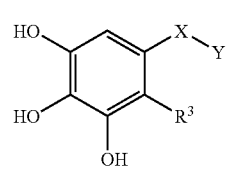

wherein the symbols, indices and substituents have the following meaning
$R^1$=H, CN, $NO_2$, $CF_3$, F, Cl, Br, I, $CH_3$
$R^2$=H, CN, $NO_2$, $CF_3$, F, Cl, Br, I, $CH_3$, Et, n-Pr, i-Pr, n-Bu, t-Bu, phenyl, thienyl, furyl, thiazolyl and
either $R^1$ or $R^2$ must be H
$R^3$=H, CN, $NO_2$, $CF_3$, F, Cl, Br, I, $CH_3$, Et, n-Pr, i-Pr, n-Bu, t-Bu, phenyl, thienyl, furyl, thiazolyl
then X is e.g.

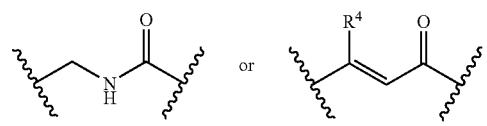

with $R^4$ being H, $CH_3$, $CH_2CH_3$
or

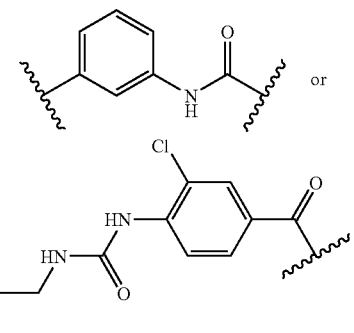

and Y being

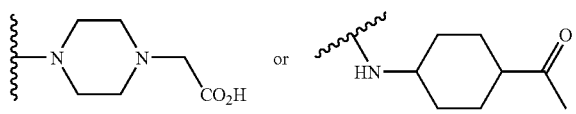

or the pharmaceutically acceptable salts, esters or amides and prodrugs of the above identified compounds of formulas (Ia) or (Ib). The compounds are applied to modulate the in-vitro and in-vivo binding processes mediated by E-, P- or L-selectin binding.

7 Claims, No Drawings

U.S. PATENT DOCUMENTS

| | | | |
|---|---|---|---|
| 4,476,219 | A | 10/1984 | Sakanoue et al. |
| 5,374,772 | A | 12/1994 | Carson et al. |
| 6,248,790 | B1 | 6/2001 | Uckun et al. |
| 6,340,700 | B1 | 1/2002 | Chabrier de Lassauniere et al. |
| 6,432,957 | B1 | 8/2002 | Kodoma et al. |
| 7,851,501 | B2 | 12/2010 | Aydt et al. |
| 7,919,532 | B2 | 4/2011 | Aydt et al. |
| 7,923,473 | B2 | 4/2011 | Aydt et al. |
| 2003/0187306 | A1 | 10/2003 | Sinha et al. |
| 2005/0113416 | A1 | 5/2005 | Wang et al. |
| 2006/0100245 | A1 | 5/2006 | Bakthavatchalam et al. |
| 2009/0030015 | A1 | 1/2009 | Kranich et al. |
| 2011/0053939 | A1 | 3/2011 | Aydt et al. |
| 2011/0142765 | A1 | 6/2011 | Aydt et al. |
| 2011/0152291 | A1 | 6/2011 | Aydt et al. |

FOREIGN PATENT DOCUMENTS

| | | |
|---|---|---|
| EP | 0465122 A1 | 1/1992 |
| EP | 0426468 B1 | 9/1995 |
| EP | 0840606 B1 | 6/2000 |
| EP | 1 081 151 A1 | 3/2001 |
| EP | 0758243 B1 | 3/2003 |
| EP | 1481669 A1 | 12/2004 |
| EP | 1577289 A1 | 9/2005 |
| EP | 1627644 A1 | 2/2006 |
| JP | 10-306024 | 11/1998 |
| JP | 2003-055369 A | 2/2003 |
| JP | 2003 055369 A | 6/2003 |
| WO | WO 97/01335 | 1/1997 |
| WO | WO 97/01569 A1 | 1/1997 |
| WO | WO 99/29705 A2 | 6/1999 |
| WO | WO 99/29705 A3 | 6/1999 |
| WO | WO 99/29706 A2 | 6/1999 |
| WO | WO 99/29706 A3 | 6/1999 |
| WO | WO 00/33836 A1 | 6/2000 |
| WO | WO 03/075905 A1 | 9/2003 |
| WO | WO 03/097658 A2 | 11/2003 |
| WO | WO 03/097658 A3 | 11/2003 |
| WO | 2004/018428 A1 | 3/2004 |
| WO | WO 2004/018502 A1 | 3/2004 |
| WO | 2004/054977 A1 | 7/2004 |
| WO | 2004056774 A2 | 7/2004 |
| WO | 20051046683 A1 | 5/2005 |
| WO | WO 2005/090284 A1 | 9/2005 |
| WO | WO 2007/039111 A3 | 4/2007 |
| WO | WO 2007/039112 A1 | 4/2007 |
| WO | WO 2007/039113 A1 | 4/2007 |
| WO | WO 2007/039114 A1 | 4/2007 |

OTHER PUBLICATIONS

Patani et al. (Bioisosterism: A Rational Approach in Drug Desing, Chemical Rev., 1996, 96 (8), 3147-3176).*

Merck Online Manuals, Crohn's disease, Revision Jan. 2007, by David B Bachar MD.*

Of Appeldoorm et al, Journal of Biochemical Chemistr, vol. 278, No. 12, Mar. 2009, pp. 10201-10207.*

Appeldoorn, C.C.M., et al., "Rational Optimization of a Short Human P-selectin-binding Peptide Leads to Nanomolar Affinity Antagonists," *J. Biol. Chem.* 278: 10201-10207, American Society for Biochemistry and Molecular Biology (Jan. 13, 2003).

STN Database Accession No. 1961:22545, English language abstract for Shingaki, T.,"Reaction of substituted benzazides with benzylamine," *Nippon Kagaku Zasshi* 80:55-58, Nippon Kagakukai (1959).

STN Database, Accession No. 1961:22544, English language abstract for Slyusarev, A.T. and Gershuns, A. L., "Gallic acid anilides," *Ukrains'kii Khemichnii Zhur.* 26:364-367, Naukova Dumka (1960).

STN Database Accession No. 1962:446635, English language abstract for Manning, D.L. and Blander, M., "Association constants of silver (I) and cyanide ions in molten equimolar sodium nitrate-potassium nitrate mixtures," *Inorg. Chem.* 1:594-599, American Chemical Society (1962).

STN Database Accession No. 1962:446636, English language abstract for Slyusarev, A.T and Gershuns, A. L., "Dissociation of p-carboxygallanilide," *Ukrainskii Khimicheskii Zhur.* 28:309-315, Naukova Dumka (1962).

STN Database Accession No. 1964: 86480, English language abstract for Lapin, N.N., and Efimenko, A.G., "Determination of titanium in heat-resistant steels," *Sb. Nauchn. Tr. Zhdanovsk. Met. Inst.* 9:103-107 (1963).

STN Database Accession No. 1964:428806, English language abstract for Slyusarev, A.T and Gershuns, A. L.,"Dissociation of p-carboxygallic anilide," *Inst. Khim.* 133:95-103 (1963).

STN Database Accession No. 1972:85515, English language abstract for Morlyan, N.M., et al., "N-(3,4,5-Trimethoxybenzoyl)-p-aminobenzoic acid," *Metody Poluch. Khim. Reaktiv. Prep.* 20:121-123 (1969).

STN Database Accession No. 1976:536659, English language abstract for Paschenko, E.N., et al., "Photometric determination of molybdenum in tungsten and its alloys as a carboxygallanilide complex," *Zhur. Anal. Khimii* 31:400-401, Izd—vo Akademii Nauk SSR (1976).

STN Database Accession No. 1975:612201, English language abstract for Russian Patent No. SU 480 000 (1975).

STN Database, Accession No. 1987:467992, English language abstract for Japanese Patent No. JP 61 282839 (1986).

STN Database, Accession No. 1990:45554, English language abstract for Japanese Patent No. JP 01 120554 (1989).

STN Database, Accession No. 1996:513596, English language abstract for Japanese patent No. JP 08 143525 (1996).

Beilstein Database, Registry No. 2763456, "*N*-(4-dimethylamino-phenyl)-3,4,5-trihydroxy-benzamide," Beilstein Institut zur Foerderung der Chemischen Wissenchaften, 2 pages (1989-1992).

Beilstein Database, Registry No. 2765383, "*N*-(4-diethylamino-phenyl)-3,4,5-trihydroxy-benzamide," Beilstein Institut zur Foerderung der Chemischen Wissenchaften, 2 pages (1989-1992).

International Search Report for International Application No. PCT/EP2005/002920, European Patent Office, Netherlands, mailed on Jun. 15, 2005.

Badcock et al., "The Chemistry of the 'Insoluble Red' Woods. Part IV. Some Mixed Benzoins," J. Chem. Soc. 2961-2965 (1950).

Whalley, "The Isomerization of isoFlavones," J. Chem. Soc. 3366-3371 (1953).

Feb. 17, 2012, Office Action in U.S. Appl. No. 13/032,760.

R.P. McEver, "8 Interactions of Selectins with PSGL-I and Other Ligands," Ernst Schering Res. Found. Workshop 44:137-147 (2004).

G. Constantin, "PSGL-I as a Novel Therapeutic Target," Drug News Perspect 17(9):579-586 (Nov. 2004).

Okazaki et al., "Enhancement of Metastatic Activity of Colon Cancer as influenced by Expression of Cell Surface Antigens," Journal of Surgical Research 78(JR985298):78-84 (Sep. 22, 1997).

A.M. Müller et al., "Heterogeneous expression of cell adhesion molecules by endothelial cells in ARDS," Journal of Pathology 198(2):270-275 (2002).

R.P. McEver, "Selectin-carbohydrate interactions during inflammation and metastasis," Glycoconjugate Journal 14:585-591 (1997).

R.P. McEver et al., "Perspectives Series: Cell Adhesion in Vascular Biology" "Role of PSGL-I Binding to Selectins in Leukocyte Recruitment," J. Clin. Invest., The American Society for Clinical Investigation, Inc. 100(3):485-492 (Aug. 1997).

A. Di Stefano et al., "Upregulation of Adhesion Molecules in the Bronchial Mucosa of Subjects with Chronic Obstructive Bronchitis," Am. J. Respir. Crit. Care. Med. 149(3):803-810 (1994).

S. Terajima et al., "An important role of tumor necrosis factor-$\alpha$ in the induction of adhesion molecules in psoriasis," Arch. Dermatol. Res. 290:246-252 (1998).

M. Sperandio et al., "Blocking Leukocyte Rolling: Does it have a Role in Disease Prevention?" Vascular Disease Prevention 1:185-195 (2004).

C.A. Lipinski et al., "Experimental and computational approaches to estimate solubility and permeability in drug discovery and development settings," Advanced Drug Delivery Reviews, 23:3-25 (1997).

H. Ulbrich et al., "Leukocyte and endothelial cell adhesion molecules as targets for therapeutic interventions in inflammatory disease," Trends in Pharmacological Sciences 24(12):640-647 (2003).

S.J. Romano, "Selectin Antagonists, Therapeutic Potential in Asthma and COPD," Treat. Respir. Med. 4(2):85-94 (2005).

M.P. Schön, "Inhibitors of selectin functions in the treatment of inflammatory skin disorders," Therapeutics and Clinical Risk Management 1(3):201-208 (2005).

M. Kumamoto et al., "Effects of pH and Metal Ions on Antioxidative Activities of Catechins," Biosci. Biotechnol. Biochem. 64(1):126-132 (2001).

E. Sergediene et al., "Prooxidant toxicity of polyphenolic antioxidants to HL-60 cells: description of quantitative structure-activity relationships," FEBS Letters 462:392-396 (1999).

K. Satoh et al., "Copper, but not Iron, Enhances Apoptosis-Inducing Activity of Antioxidants," Anticancer Research 17:2487-2490 (1997).

N. Sakuguchi et al., "Reactive Oxygen Species and Intracellular $Ca^{2+}$, Common Signals for Apoptosis Induced by Gallic Acid," Biochemical Pharmacology 55:1973-1981 (1998).

D. Bock et al., "Innovative Strategy in Inflammatory Diseases," New Drugs D04(28):28-30 (2003).

E. Aydt et al., "Development of Synthetic Pan-Selectin Antagonists: A New Treatment Strategy for Chronic Inflammation in Asthma," Pathobiology 70:297-301 (2002-2003).

N.V. Bovin, "Neoglycoconjugates: trade and art," Biochem. Soc. Symp. 69:143-160 (2002).

N.V. Bovin, "Polyacrylamide-based blycoconjugates as tools in glycobiology," Glycoconjugate Journal 15:431-446 (1998).

T.V. Pochechueva et al., "P-Selectin Blocking Potency of Multimeric Tyrosine Sulfates In Vitro and In Vivo," Bioorganic & Medicinal Chemistry Letters 13(10):1709-1712 (2003).

G. Weitz-Schmidt et al., "An E-Selectin Binding Assay Based on a Polyacrylamide-Type Glycoconjugate," Analytical Biochemistry 238:184-190 (1996).

T. Nomoto et al., "Preparation of hydroxybenzamide derivatives as prevention and treatment agents for bone diseases," Chemical Abstracts + Indexes, American Chemical Society 125(13):XP002047512 (Sep. 23, 1996).

R. Yamazaki et al., "Diarylheptanoids suppress expression of leukocyte adhesion molecules on human vascular endothelial cells," European Journal of Pharmacology 404(3):375-385, XP009062460 (Sep. 22, 2000).

C.C.M. Appeldoorn et al., "Gallic Acid Antagonizes P-Selectin-Mediated Platelet-Leukocyte Interactions, Implications for the French Paradox," Circulation 111:106-112 (Jan. 2005).

N. Kaila et al., "Quinic Acid Derivatives as Sialyl Lewis$^x$-Mimicking Selectin Inhibitors: Design, Synthesis, and Crystal Structure in Complex with E-Selectin," J. Med. Chem. 48:4346-4357 (2005).

D.H. Slee et al., "Development of Potent Non-Carbohydrate Imidazole-Based Small Molecule Selectin Inhibitors with Antiinflammatory Activity," J. Med. Chem. 44:2094-2107 (2001).

P.T. Mannisto et al., "Catechol-$O$-methyltransferase (COMT): Biochemistry, Molecular Biology, Pharmacology, and Clinical Efficacy of the New Selective COMT Inhibitors," Pharmacological Reviews, The American Society for Pharmacology and Experimental Therapeutics 51(4):593-628 (1999).

J. Axelrod et al., "Enzymatic O-Methylation of Epinephrine and Other Catechols," J. Biol. Chem. 223(3):702-705 (1958).

N. Haramaki et al., "Role of Ascorbate in Protection by Nitecapone Against Cardiac Ischemia—Reperfusion Injury," Biochemical Pharmacology 50(6):839-843 (1995).

E. Nissinen et al., "The COMT inhibitor, entacapone, reduces levedopa-induced elevations in plasma homocysteine in healthy adult rats," J. Neural. Transrn. 112:1213-1221 (2005).

Y.J. Suzuki et al., "Antioxidant Properties of Nitecapone (OR-462)," Free Radical Biology & Medicine 13:517-525 (1992).

L. Marcocci et al., "Nitecapone: A Nitric Oxide Radical Scaventer," Biochemistry and Molecular Biology International 34(3):531-541 (Oct. 1994).

T. Helkamaa et al., "Entacapone protects from angiotensin II-induced inflammation and renal injury," Journal of Hypertension 21:2353-2363 (2003).

Friedrich et al., "Pan-selectin antagonism improves psoriasis manifestation in mice and man," Arch Dermatol Res. 297:345-351, XP002370636 (2006).

Van De Waterbeemd H et al., "Property-Based Design: Optimization of Drug Absorption and Pharmacokinetics," J. Med. Chem. 44(9):1313-1333 (2001).

Harvey et al., "The results of five coded compounds: genistein, metaproterenol, rotenone, $p$-anisidine and resorcinol tested in the pH 6.7 Syrian hamster embryo cell morphological transformation assay," Mutagenesis 20(1):51-56 (2005).

Nov. 16, 2009, Office Action in U.S. Appl. No. 12/067,389.
Jul. 30, 2010, Office Action in U.S. Appl. No. 12/067,389.
Jul. 30, 2010, Office Action in U.S. Appl. No. 12/066,757.
Feb. 14, 2011, Office Action in U.S. Appl. No. 12/066,757.
Jan. 8, 2010, Office Action in U.S. Appl. No. 12/067,341.
Nov. 18, 2009, Office Action in U.S. Appl. No. 12/067,059.
Jul. 29, 2010, Office Action in U.S. Appl. No. 12/067,059.
Abstract of JP2003-055369 A.
Apr. 16, 2012, Office Action in U.S. Appl. No. 13/037,575.
Bakthavatchalam et al., "Substituted biphenyl-4-carboxylic acidarylamide analogues as VR1 receptors modulators," CAS 141:89019 (2004).
English-language abstract of JP 10-306024, Nov. 17, 1998.

* cited by examiner

NON-GLYCOSYLATED/NON-GLYCOSIDIC/ NON-PEPTIDIC SMALL MOLECULE PSGL-1 MIMETICS FOR THE TREATMENT OF INFLAMMATORY DISORDERS

The present invention relates generally to compounds, compositions and methods for modulating the in vitro and in vivo processes mediated by E-selectin, P-selectin or L-selectin. More specifically, a novel class of small molecule PSGL-1 mimetics and their use are described. The disclosed small molecules comprise trihydroxy phenyl subunits and inhibit selectin-mediated functions potently.

When a tissue has been invaded by a microorganism, is infected or has been damaged, the inflammatory process directs leukocytes and other immune system components to the site of infection or injury. Within this process, leukocytes (white blood cells) play a major role in the engulfment or digestion of microorganisms. Thus, the recruitment of leukocytes to infected or damaged tissue is critical for mounting an effective immune defense. Generally, white blood cells are found circulating through the bloodstream. To migrate from the blood stream into the affected tissue, the white blood cells must be able to recognize the invaded or damaged tissue, be able to bind to the wall of the capillary endothelium near the affected tissue and diffuse through the cell wall of the capillary into the affected tissue. Therefore, leukocytes have to roll onto and then adhere to the endothelial cell wall. This cell adhesion event is one of the most important aspects of the inflammatory response. The first steps of this cell adhesion are mediated by members of the selectin family. The selectin family of vascular adhesion molecules is comprised of three structurally related calcium-dependent carbohydrate binding cell surface proteins, E-, P- and L-selectin. E-selectin is expressed only on inflamed endothelium, P-selectin is expressed on inflamed endothelium as well as on platelets, and has structural similarity to E-selectin. L-selectin is expressed on leukocytes and also has structural similarity to P- and E-selectin.

The selectins are transmembrane proteins and are composed of an amino terminal lectin domain, an epidermal growth factor (EGF)-like domain, a variable number of complement receptor-related repeats, a hydrophobic domain spanning region and a cytoplasmic domain. The binding interactions which lead to the adhesion of the leukocytes appear to be mediated by contact of the lectin domain of the selectins and various carbohydrate ligands on the surface of the leukocytes. All three selectins can bind with low affinity to the carbohydrate sialyl Lewis$^x$ (sLe$^x$), a glycosyl moiety present on the surface of most leukocytes. A structurally related glycosyl moiety, sialyl Lexis$^a$ (sLe$^a$), is predominately found on the surface of cancer cells [K. Okazaki et al.; *J. Surg. Res.;* 1998; 78(1); 78-84 and R. P. McEver et al.; *Glycoconjugate Journal;* 1997; 14(5); 585-591]. In case of P-selectin, a distinct high affinity glycoprotein ligand has been described [R. P. McEver; R. D. Cummings; *J. Clin. Invest.;* 1997; 100; 485-492], the so-called PSGL-1 (P-selectin glycoprotein ligand-1), which contributes to a high affinity selectin binding by its sLe$^x$ moiety as well as by parts of its peptide components, in particular sulphated tyrosine residues [R. P. McEver; *Ernst Schering Res. Found. Workshop;* 2004; 44; 137-147]. PSGL-1 is one of the most important selectin ligands binding with highest affinity to P-selectin, but it also binds to E- and L-selectin [G. Constantin; *Drug News Perspect;* 2004; 17(9); 579-586]. It is a homodimeric sialomucin predominantely expressed on leukocytes.

In contrast to their low basal expression, E- and P-selectin expression is upregulated during inflammation, leading to a substantial recruitment of leukocytes into the inflamed tissue. Although selectin-mediated cell adhesion is required for fighting infection, there are various situations in which such cell adhesion is undesirable or excessive, resulting in severe tissue damage instead of repair. In the case of many acute as well as chronic inflammatory disorders [e.g., asthma, chronic obstructive pulmonary disease (COPD), psoriasis, etc.], an association between infiltration of activated leukocytes into the tissue simultaneously with a marked elevation of tissue expression of corresponding adhesion molecules, particularly E- and P-selectin, has been demonstrated.

White blood cell infiltration may also play a role in inflammatory symptoms in the course of transplant and graft rejection. Also the process of blood clotting is further promoted by leukocyte-leukocyte and leukocyte-platelet binding, which occurs because leukocytes possess both L-selectin and its corresponding ligand PSGL-1 and can thus interact with themselves via PSGL-1, and they can also bind to platelets which carry P-selectin.

Therefore, the inhibition of selectin-mediated cell adhesion offers a promising possibility to interfere with and stop the inflammation cascade at a very early step. Small molecule selectin inhibitors should inhibit all three selectins simultaneously as pan-selectin-antagonists to circumvent possible redundancies between the selectins [M. Sperandio et al.; *Vascular Disease Prevention;* 2004; 1; 185-195].

Besides sLe$^x$/sLe$^a$, the natural, high affinity ligand PSGL-1 is another template structure for the design of small molecule selectin inhibitors. As compared to sLe$^x$/sLe$^a$, PSGL-1 shows high affinity for all three selectins. To find and to detect novel small molecule drugs that compete with PSGL-1 for selectin binding is therefore a promising strategy to develop a novel class of effective pan-selectin antagonists for treating inflammatory disorders. Selectin inhibitors may be designed using selectins as well as a ligand like PSGL-1 as a template structure, since they are intended to inhibit the binding between selectins and PSGL-1 or other ligands with similar binding motifs.

Novel small molecule selectin inhibitors could meet certain requirements to be drug-like and to have potential oral bioavailability. The term drug likeness is described in the literature [Lipinski; *Adv. Drug Dev. Rev.;* 1997; 23; 3-25]. Beside other molecular properties, passively transported molecules are supposed to have a relative molecular weight of less than 500 in order to be drug like. According to these rules it is common to define compounds with a relative molecular weight less than 500 as small molecules, which is a prerequisite for molecules to be drug like and thereby orally bioavailable. Also the presence of a highly polar carbohydrate moiety or a peptidic component is not in accordance with the concept of drug likeness [H. Ulbrich et al.; *Trends Pharmacol. Sci.;* 2003; 24(12); 640-647. D. Slee et al.; *J. Med. Chem.;* 2001; 44; 2094-2107]. Moreover, the desired compounds must be stable during the passage through the gastrointestinal tract so that they can be ingested/absorbed latest by the cells of the small intestines, which is not the case for most glycosidic molecules and peptidic structures. Most structures cited below as typical prior art examples with selectin inhibitory capacity have either high potency while being large, non-drug-like molecules with unfavourable ADME properties or low potency while being small to mid-sized sLe$^x$- or sLe$^a$-glycomimetics with unfavourable ADME properties.

EP 1 081 151 A 1 discloses novel bioactive compounds for the treatment of abnormal angiogenesis.

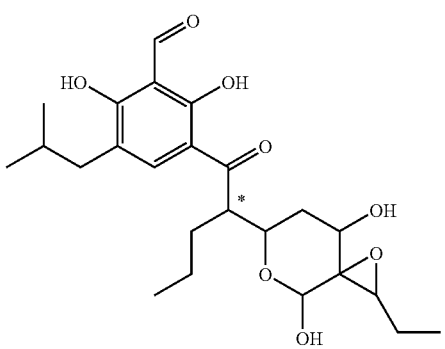 [SMILES: CCCC(C(=O)c1cc(CC(C)C)c(O)c(C=O)c1O)C1CC(O)C2(OC2CC)C(O)O1]

The structures are novel anti-inflammatory substances being also potential inhibitors of VCAM as well as E-selectin expression, but no inhibitors of selectin-mediated binding.

U.S. Pat. No. 6,340,700 B1 provides compounds which have an inhibitory activity against NO-synthase enzymes producing nitrogene monoxide NO and/or an activity which traps the reactive oxygene species (ROS) and which may produce this way favourable effects in treatment of inflammatory diseases. A typical compound is

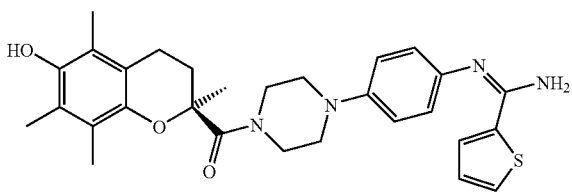

Also mentioned is the preparation of smaller intermediates leading to these compounds. A medical use of these intermediates is not claimed. E.g. one of these intermediates is

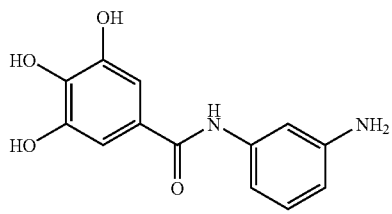 [SMILES: Nc1cccc(NC(=O)c2cc(O)c(O)c(O)c2)c1]

The disalicylates and disalicylate-based C-glycosides of WO 99/29706 act as selectin-ligand structural mimetics in medicaments. They may lack the sialic acid and/or fucose of the natural selectin ligand being sLe$^x$. A typical compound of the group of carbohydrate free sLe$^x$-glycomimetics with low to moderate biological activity is

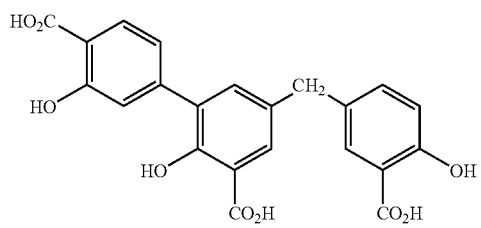 [SMILES: O=C(O)c1ccc(-c2cc(Cc3ccc(O)c(C(=O)O)c3)cc(C(=O)O)c2O)cc1O]

Due to the presence of three polar, possibly charged carboxylic groups, this structure is not in agreement with Lipinski's rules—as defined before—, indicating a possibly poor oral bioavailability. An additional carbohydrate moiety further reduces the potential of oral bioavailability.

According to WO 03/097658 the compounds for modulating in vitro and in vivo processes mediated by selectin binding are benzyl amino sulfonic acids, which may be linked to carbohydrate or a glycomimetic. The compounds disclosed have mostly activities in the mM range. One of the most potent compounds with a relative molecular weight of 1505 is

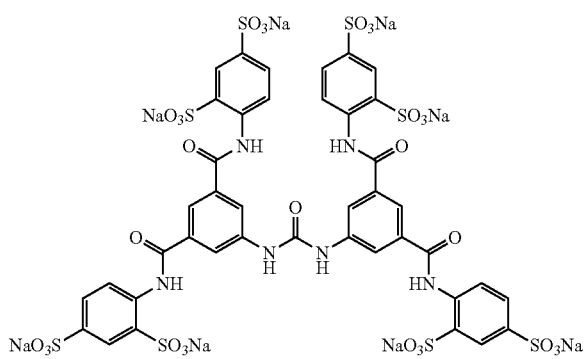

WO 99/29705 describes sLe$^x$- and sLe$^a$-glycomimetics, which may be useful in the treatment of selectin-mediated disorders. A typical compound is

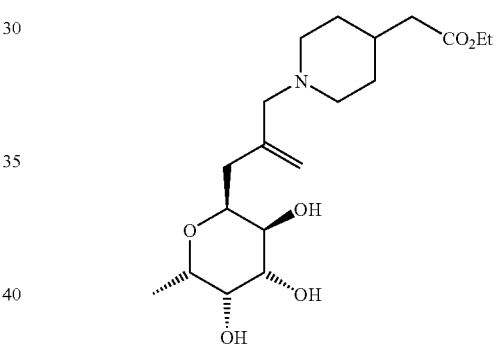

Most of the compounds cover carbohydrate-like structures and are therefore likely to have the typical pharmacokinetic disadvantages associated with carbohydrates. Few non-glycosidic sLe$^x$- and sLe$^a$-glycomimetics are described. On average the activities of the disclosed structures are in the mM range.

WO 97/01569 discloses diglycosylated 1,2 diols as mimetics of sLe$^x$ and sLe$^a$. These glycosidic compounds are large and prone to digestive degradation in the intestine, which both impairs oral bioavailability. An example is

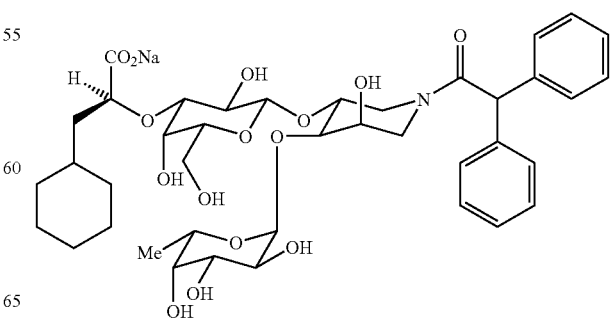

The substituted 5-membered heterocycles of WO 00/33836 exhibit inhibitory activity against E- and P-selectin only. The compounds are sLe$^x$-glycomimetics. One of the most potent compounds is

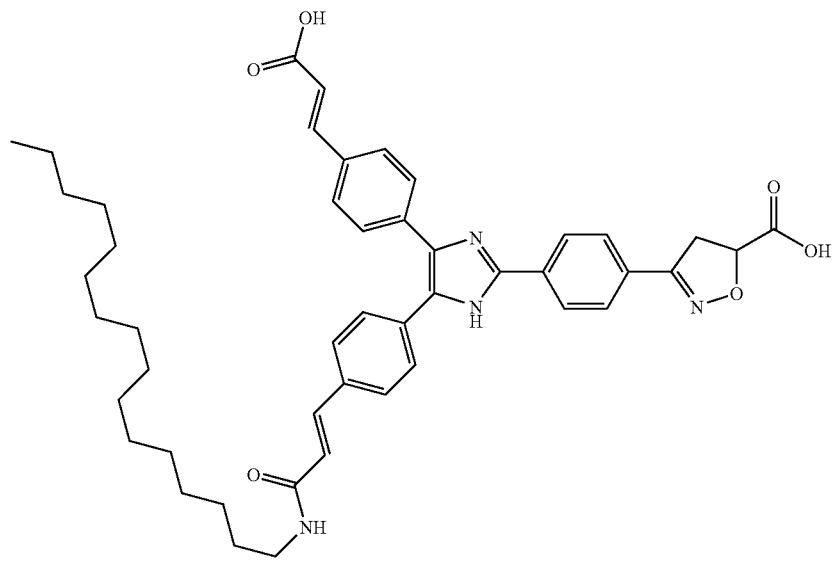 [SMILES: CCCCCCCCCCCCCCCCNC(=O)/C=C/c1ccc(-c2[nH]c(-c3ccc(C4=NOC(C(=O)O)C4)cc3)nc2-c2ccc(/C=C/C(=O)O)cc2)cc1]

with a relative molecular weight of 773. Clinical development has not been reported for these molecules.

EP 0 758 243 B1 describes Mannopyranosyloxy-phenyl-benzoic acid or similar acids as components in a medicine for treating or preventing diseases, characterized by the binding of E-, P- and/or L-selectin to sLe$^x$ or sLe$^a$ being present on the cell surface through the inhibition of such binding. Besides inflammatory diseases (like psoriasis or rheumatoid arthritis) other diseases like septic shock, reperfusion injury and cancer are mentioned. These molecules also possess a carbohydrate moiety and could therefore have only low bioavailability.

D. Bock et al., [*New Drugs*, 2003, D04, 28; p. 28] describe the role of selectin antagonists, especially bimosiamose, as inhibitor of selectins being an inflammation target:

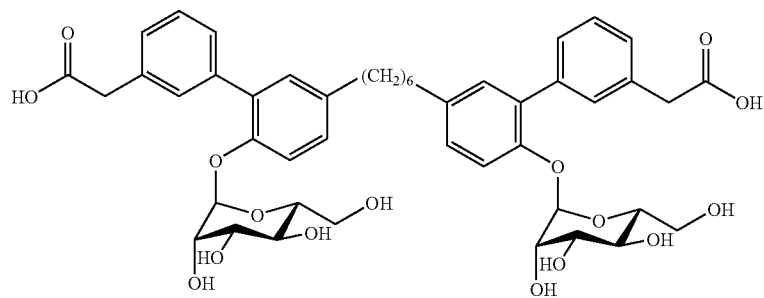

From EP 0 840 606 B1 compounds like bimosiamose are known, e.g., 1,6-Bis-[3-(carb-oxymethylphenyl)-4-(2-α-D-mannopyranosyloxy)phenyl]hexan and derivatives thereof including heptan, butan and pentan derivatives. Again, their use for inhibiting the selectin binding to sLe$^x$ or sLe$^a$ is mentioned. Bimosiamose and related compounds have been developed originally as sLe$^x$- and sLe$^a$-glycomimetics. However, recent investigations support the hypothesis that bimosiamose can be considered as PSGL-1 mimetic [E. Aydt, G. Wolff; *Pathobiology;* 2002-2003; 70; 297-301]. Bimosiamose has a relative molecular weight of 862 and covers two mannose units, which presumably prevents the molecule to be orally bioavailable. This seems to be the only selectin inhibitor, which is currently in clinical trials. Yet, these molecules possess even more than one carbohydrate moiety and are known to lack oral bioavailability.

A different method for inhibiting the binding between a first cell having a selectin and a second cell having a ligand for selectin in vitro is described in EP 0 902 681 B1 in permitting a covalently cross-linked lipid composition to interact with the first cell. A proportion of the lipids has an attached saccharide like fucooligosaccharides, lactose, or an acidic monosaccharide, further proportions are cross-linked and a proportion without attached saccharides has an acidic group being negatively charged at neutral pH. These lipid compositions are used in local alterations in the adherence of leukocytes or cancer cells to vascular endothelium, platelets or lymphatic tissue. Since these compositions are covalently cross-linked, they will resemble multimers with a relative molecular weight, which by far exceeds 500. Moreover, they contain as well carbohydrate moieties. All these properties render oral bioavailability highly improbable.

WO 2004/018502 describes derivatives of compounds which bind selectively to human P-selectin being peptide containing structures with Glu-Trp-Val-Asp-Val consensus motif to which gallic acid or 1,3,5-benzenetricarboxylic acid at the N-terminus may be added. In addition to the use of such compounds in therapeutic or diagnostic methods to treat inflammatory disorders is mentioned. The necessity to consider PSGL-1 as template structure for developing high affinity selectin inhibitors is described. The type of biological in vitro assays they are using for compound assessment also reflects this. The molecules described have high inhibition potency against human P-selectin, but not against E- and L-selectin. However, their molecular and biological properties render them most probably not orally biovailable. They are unlikely to pass the digestive tract due to their peptidic moieties, which will be degraded by peptidases. In case traces should reach the small intestines, they will probably not be absorbed by passive transport due to their high molecular weight. The most potent compounds have relative molecular weights over 700 and can therefore no longer be considered as small molecule drugs. Two typical substituents are

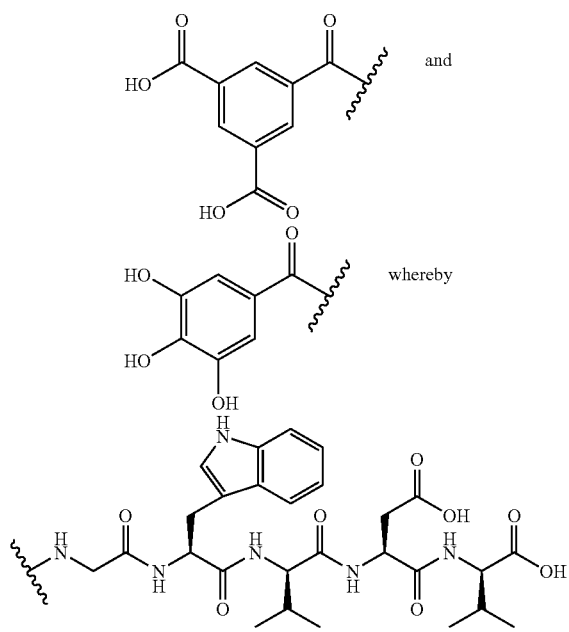

is a typical peptide entity.

WO 01/89531 provides methods for identifying agents which interact with (activate or inhibit) the crystal and three-dimensional structures of a) the lectin and EGF-like (LE) domains of P-selectin, of b) P-selectin LE and E-selectin LE each complexed with sLe$^x$, and c) P-selectin LE complexed with a functional fragment of the PSGL-1 peptide modified by both tyrosine sulfation and sLe$^x$.

In such a very complex pharmaceutical field, there is a strong medical need in the art for identifying novel kinds of inhibitors of selectin-mediated function, e.g. of selectin-dependent cell adhesion, and for the development of methods employing such compounds to inhibit conditions associated with selectin-ligand interaction. Most of the available anti-inflammatory pharmaceutical therapies, which are available on the market comprise mostly corticosteroids or NSAIDs (non steroidal anti-inflammatory drugs) which have several serious drawbacks/side effects, and target different steps of the inflammatory cascade. Unlike this, inhibiting the selectin function is a therapeutic concept intervening the inflammation cascade at a very early stage. Almost all promising selectin inhibitors so far failed to become marketed drugs, not at least because of their low biological activity and/or high molecular weight that causes problems in their absorption-distribution-metabolism-excretion (ADME) behaviour and thus in oral bioavailability which is required for the treatment of most inflammatory disorders like rheumatoid arthritis, septic shock, atherosclerosis, reperfusion injury and many others.

Most of the compounds published in the field of selectin inhibitors are peptide- and/or carbohydrate-bearing structures, which are prone to degradation and modification by peptidases and/or glycosidases. Carbohydrate-bearing structures have further disadvantages such as high molecular weight, high degree of chirality, anomericity, and low probability of transport through lipid bilayers. Similar disadvantages are known for peptide-bearing compounds. Thus, these compounds cannot be considered as small and drug-like molecules, a prerequisite for the development of orally bioavailable selectin inhibitors and drugs in general to be marketed.

Few non-glycosidic and non-peptidic compounds have been described in this field, which are molecules with high relative molecular weight and/or low biological activity. Almost all compounds have been designed on the basis of sLe$^x$ and sLe$^a$ and are therefore glycomimetics. However, the concept of designing sLe$^x$- and sLe$^a$-glycomimetics to treat inflammatory disorders has not proven to be successful to date.

Object of the invention is to provide novel small molecules, especially non-glycosylated/non-glycosidic and non-peptidic compounds, which are able to potently inhibit selectin-mediated processes and which have less negative side effects during their in vitro or in vivo application than prior art compounds.

Unlike most of these glycomimetics, the inventive compounds are not prone to glycosidases or peptidases. Most of the selectin inhibitors developed so far are sLe$^x$- or sLe$^a$-glycomimetics. This invention, however, provides novel potent small and drug like selectin inhibitors that have been invented on the basis of PSGL-1-like biological in vitro assays. A bioassay has been established implying a PSGL-1-substitute as a selectin-ligand and P-, E-, or L-selectin chimera as binding molecule/receptor. The PSGL-1-substitute used is sLe-Tyrosin-sulfate-polymer. Tyrosin-sulfate residues as well as sLe$^x$-residues have been covalently linked to a polyacrylamid matrix where they are statistically distributed. This technique to mimic the mucin-like molecule PSGL-1 and structurally related ligands is widely used and usage of sLe$^x$-Tyrosin-sulfate-polymer gives very good selectin-binding results [N. V. Bovin; *Biochem Soc Symp.*; 2002; (69):143-60. N. V. Bovin; *Glycoconj. J.*; 1998; 15(5); 431-46. T. V. Pochechueva et al.; *Bioorg Med Chem. Lett.*; 2003; 13(10); 1709-12. G. Weitz-Schmidt et al.; *Anal. Biochem.*; 1996; 238; 184-190]. Also, this technique has been used to establish an assay in WO 2004/018502, but with the restriction, that the carbohydrate moiety of the ligand is not sLe$^x$, but sLe$^a$. sLe$^a$ is a ligand which is not generally known to be involved in physiological PSGL-1 binding and has not been described as carbohydrate moiety of PSGL-1, unlike sLe$^x$. Furthermore, the said molecules should show a good bioavailability when applied as an active ingredient in a medicine.

The present invention provides pharmaceutical compositions comprising at least one compound having the general structure of formulas (Ia) or (Ib) and a pharmaceutically acceptable carrier which is useful in medicine

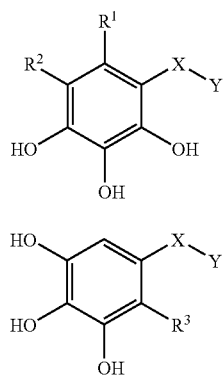

Ia

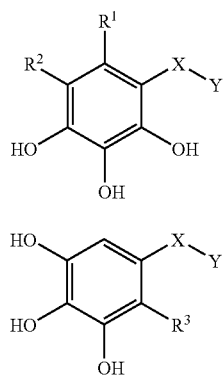

Ib wherein the symbols, indices and substituents have the following meaning $R^1$=H, CN, $NO_2$, $CF_3$, F, Cl, Br, I, $CH_3$ $R^2$=H, CN, $NO_2$, $CF_3$, F, Cl, Br, I, $CH_3$, Et, n-Pr, i-Pr, n-Bu, t-Bu, phenyl, thienyl, furyl, thiazolyl and either $R^1$ or $R^2$ must be H $R^3$=H, CN, $NO_2$, $CF_3$, F, Cl, Br, I, $CH_3$, Et, n-Pr, i-Pr, n-Bu, t-Bu, phenyl, thienyl, furyl, thiazolyl

—X—=

(a)

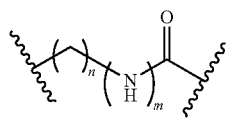

with m=0,1; n=an integer from 1 to 6

(b)

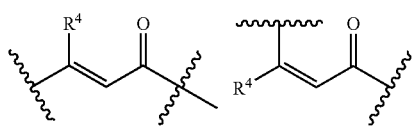

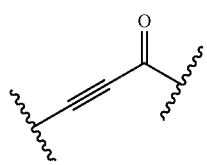

with $R^4$ being H, $CH_3$, $CH_2CH_3$ c)

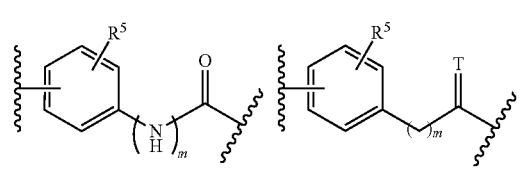

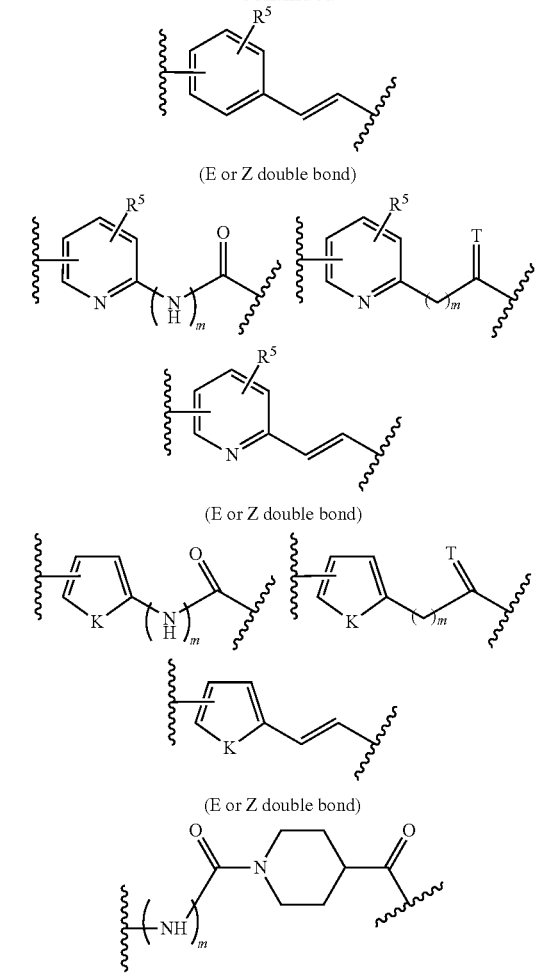

with $R^5$ being H, $NO_2$, $CF_3$, F, Cl, Br, I, CN, $CH_3$, $NH_2$, NHAlkyl, NHAryl, NHAcyl and —K— being —S— or —O— and T being O, S or [H,H]

(d)

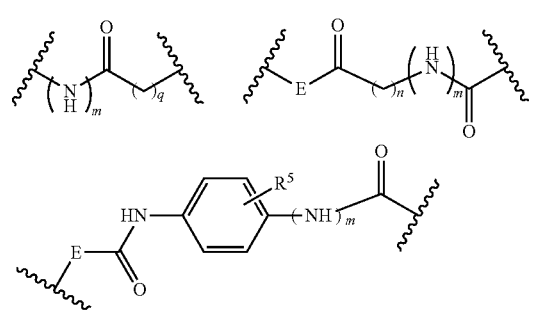

-continued

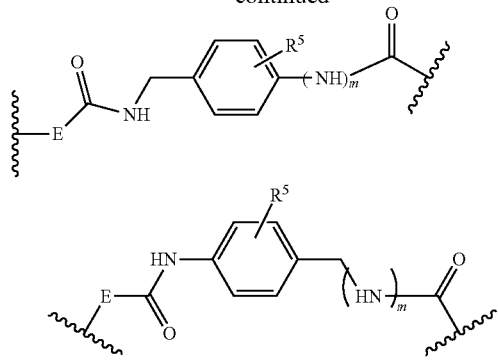

with -E- being —(CH$_2$—)$_k$NH— and k=0, 1, 2, 3 and with q being an integer from 1 to 6

—Y=

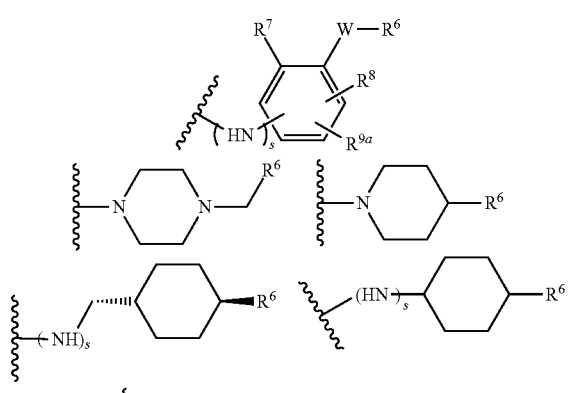

(both enantiomers)

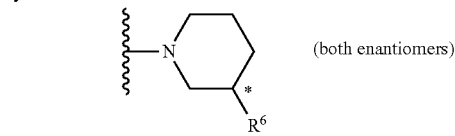

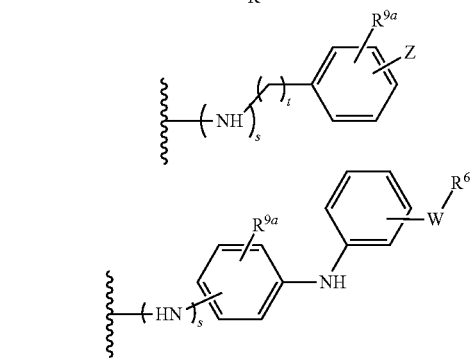

with s being 0 or 1,

R$^6$ being CO$_2$H, CO$_2$Alkyl, CO$_2$Aryl, CO$_2$NH$_2$, CO$_2$Aralkyl, SO$_3$H, SO$_2$NH$_2$, PO(OH)$_2$, 1-H-tetrazolyl-, CHO, COCH$_3$, CH$_2$OH, NH$_2$, NHAlkyl, N(Alkyl)Alkyl', OCH$_3$, CH$_2$OCH$_3$, SH, F, Cl, Br, I, CH$_3$, CH$_2$CH$_3$, CN, CF$_3$ R$^7$ independently from R$^6$ being H, CH$_3$, CH$_2$CH$_3$, CF$_3$, F, Cl, Br, I, CN, NO$_2$ and R$^8$ independently from R$^6$ and R$^7$ being H, CH$_3$, CH$_2$CH$_3$, CF$_3$, F, Cl, Br, I, CN, NO$_2$, R$^6$ R$^{9a}$ being H, NO$_2$, CF$_3$, F, Cl. Br, I, CN, CH$_3$, OCH$_3$, SH, NH$_2$ t being 0,1,2 and —W—=—(CH$_2$—)$_v$, cis-CH=CH— or trans-CH=CH—, and v being 0,1,2;

in case that R$^6$=NH$_2$R$^7$ or R$^8$ or R$^{9a}$ must not be H;

in case that —W— is cis-CH=CH— or trans-CH=CH—, R$^6$ must not be NH$_2$ or SH;

—Z=

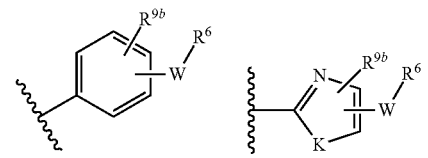

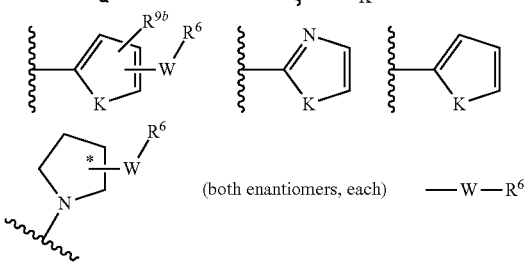

(both enantiomers, each)    —W—R$^6$

R$^{9b}$ independently from R$^{9a}$ being H, NO$_2$, CF$_3$, F, Cl. Br, I, CN, CH$_3$, OCH$_3$, SH, NH$_2$, or the pharmaceutically acceptable salts, esters or amides and prodrugs of the above identified compounds of formulas (Ia) or (Ib).

Preferred pharmaceutical compositions comprise compounds of formulas (A1), (B1), (A2) or (B2)

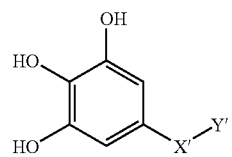
A1

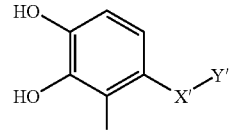
B1

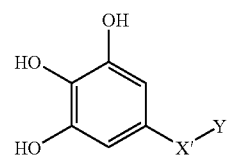
A2

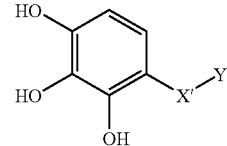
B2 wherein —X— and —Y are like defined above and wherein —X'— is

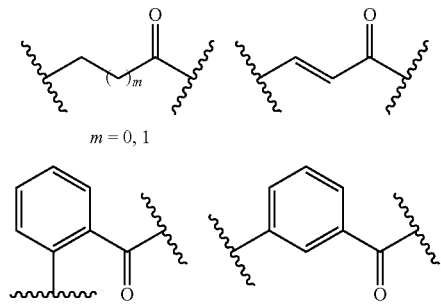

and wherein —Y' is

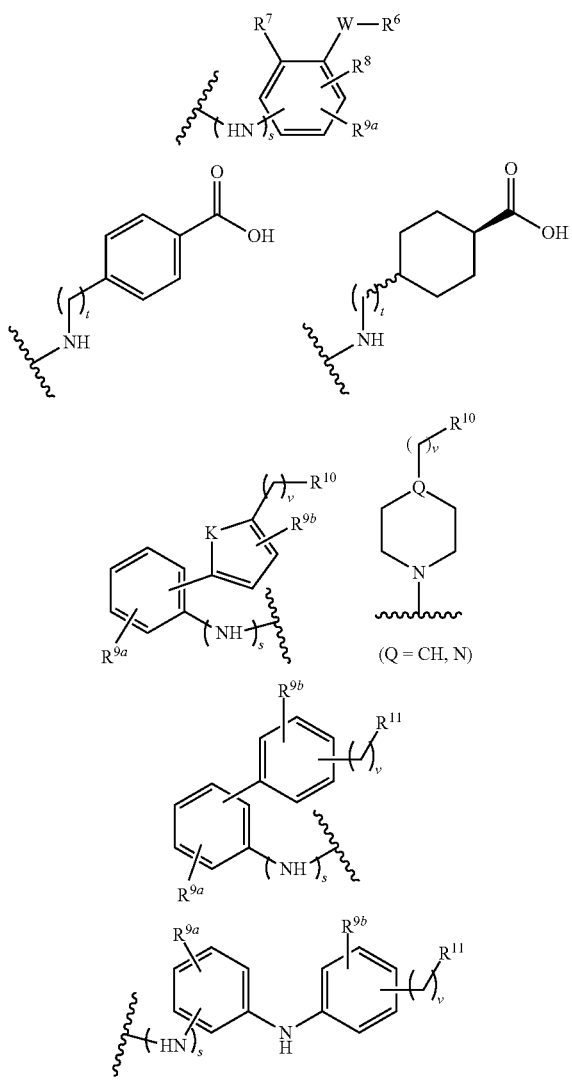

with $R^{10}$ being $CO_2H$, $CO_2$alkyl, $CO_2$aryl, $CO_2NH_2$, $CO_2$aralkyl, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2NH$alkyl, $CH_2N$(alkyl)alkyl', $CH_2OCH_3$, $CH_2SH$, $R^{11}$ being $CO_2H$, $CO_2$alkyl, $CO_2$aryl, $CO_2NH_2$, $CO_2$aralkyl, $SO_3H$, $SO_2NH_2$, $PO(OH)_2$, 1-H-tetrazolyl, CHO, $COCH_3$, OH, $NH_2$, NHalkyl, N(alkyl)alkyl', $OCH_3$, SH Further particularly preferred pharmaceutical compositions comprise compounds of formulas (C) and (D)

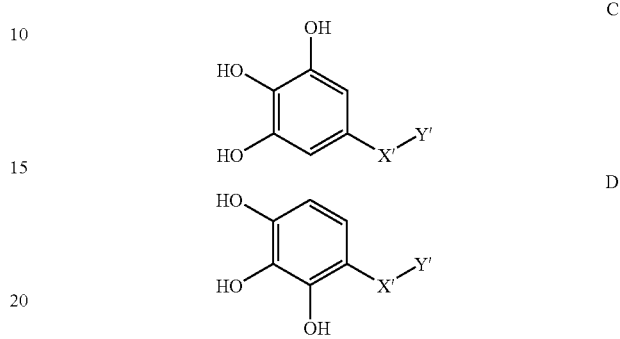

wherein —X'— and —Y' are like defined above.

These compounds (C) and (D) are also new compounds for themselves.

All compounds as described before present the ability of inhibiting cell adhesion and inhibit selectin-as well as PSGL-1-like mediated binding. The compounds have the ability to inhibit the interaction of selectins with $sLe^x/sLe^a$ and also the interaction between selectins and tyrosinesulfate residues. Therefore they are useful for the treatment of acute and chronic inflammatory disorders, as well as other medical conditions where selectin mediated processes play a role.

The term "pharmaceutical" includes also diagnostic applications.

The term "pharmaceutical" includes also prophylactic applications in order to prevent medical conditions where selectin mediated processes play a role.

The term "pharmaceutical" includes also applications, where compounds of the present invention may be used as vehicles for drug targeting of diagnostics or therapeutics.

In a further preferred variant the invention provides pharmaceutical compositions comprising at least one compound of formula (A1), (A2), (B1), (B2), (C) or (D).

The present invention further provides a method of inhibiting the binding of P-selectin, L-selectin or E-selectin to $sLe^x$ or $sLe^a$ and tyrosinesulfate residues comprising the step of administering to a patient an effective amount of at least one compound having the structure of formulas (Ia) or (Ib) to inhibit the binding of P-, E- or L-selectin to $sLe^x$ or $sLe^a$ and tyrosinesulfate. It has been found that compounds having the formulas (Ia) or (Ib) shown above act to inhibit E-, P- or L-selectin binding.

As used herein the term "alkyl" shall mean a monovalent straight chain or branched chain group of 1 or 2 or 3 or 4 or 5 or 6 or 7 or 8 or 9 or 10 or 11 or 12 carbon atoms including, but not limited to, methyl, ethyl, n-propyl, isopropyl, n-butyl, sec-butyl, tert-butyl and the like.

The term "aryl" shall mean carbocyclic and heterocyclic aromatic groups including, but not limited to, phenyl, 1-naphthyl, 2-naphthyl, fluorenyl, (1,2)-dihydronaphthyl, indenyl, indanyl, thienyl, benzothienyl, thienopyridyl and the like.

The term "aralkyl" (also called arylalkyl) shall mean an aryl group appended to an alkyl group including, but not limited to, benzyl, 1-naphthylmethyl, 2-naphthylmethyl, fluorobenzyl, chlorobenzyl, bromobenzyl, iodobenzyl, alkoxybenzyl (wherein "alkoxy" means methoxy, ethoxy, isopropoxy, n-butoxy, sec-butoxy, tert-butoxy an the like), hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with tissues of patients without undue toxicity, irritation, allergic response and the like, commensurate with a reasonable benefit/risk ratio, and effective for their intended use, as well as the zwitterionic forms, where possible, of the compounds of the present invention. The term "salts" refers to the relatively non-toxic, inorganic and organic acid addition salts of the compounds of the present invention. These salts can be prepared in situ during the final isolation and purification of the compounds or by separately reacting the purified compounds in its free form with a suitable inorganic or organic acid or base and isolating the salt thus formed. Representative salts of the compounds of the present invention include the hydrobromide, hydrochloride, sulfate, bisulfate, nitrate, acetate, oxalate, valerate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkalineearth metals, such as sodium, lithium, potassium, calcium, magnesium and the like, as well as non-toxic ammonium, quaternary ammonium and amine cations including, but not limited to, ammonium, tetramethylammonium, tetraethylammonium, methylamine, dimethyl amine, trimethylamine, triethylamine, ethylamine, and the like.

Examples of the pharmaceutically acceptable, non-toxic esters of the compounds of this invention include $C_1$, $C_2$, $C_3$, $C_4$, $C_5$ and $C_6$ alkyl esters wherein the alkyl group is a straight or branched chain. Acceptable esters also include $C_5$, $C_6$ and $C_7$ cycloalkyl esters as well arylalkyl esters such as, but not limited to, benzyl. $C_1$, $C_2$, $C_3$, $C_4$, $C_5$ and $C_6$ alkyl ester are preferred. Esters of the compounds of the present invention may be prepared according to conventional methods.

Examples of pharmaceutically acceptable, non-toxic amides of compounds of this invention include amides derived from ammonia, primary $C_1$, $C_2$, $C_3$, $C_4$, $C_5$ and $C_6$ alkyl amines and secondary $C_1$, $C_2$, $C_3$, $C_4$, $C_5$ and $C_6$ dialkyl amines wherein the alkyl groups are straight or branched chains. In the case of secondary amines the amine may also be in the form of a 5 or 6 membered heterocycle containing one nitrogen atom. Amides derived from ammonia, $C_1$, $C_2$ and $C_3$ alkyl primary amides and $C_1$ to $C_2$ dialkyl secondary amides are preferred. Amides of the compounds of the present invention may be prepared according to conventional methods.

The term "prodrug" refers to one or more compounds that are rapidly transformed in vitro and from a non-active to active state in vivo to yield to the parent compound of the above formulas (Ia) or (Ib), for example by hydrolysis in blood or in vivo metabolism.

It is also contemplated that pharmaceutically active compositions may contain a compound of the present invention or other compounds that inhibit or compete with E-selectin or P-selectin or L-selectin binding.

Pharmaceutically active compositions of the present invention comprise a pharmaceutically acceptable carrier and a compound of formulas (Ia) or (Ib), whereby a pharmaceutically acceptable carrier can also be a medically appropriate nano-particle, dendrimer, liposome, microbubble or polyethylene glycol (PEG). The pharmaceutical compositions of the present invention may include one or more of the compounds having the above structure (Ia) or (Ib) formulated together with one or more, physiologically acceptable carriers, adjuvants or vehicles, which are collectively referred to herein as carriers, for parenteral injection, for oral administration in solid or liquid form, for rectal or topical administration and the like.

The compositions can be administered to humans and animals either orally, rectally, parenterally (intravenously, intramuscularly, intradermaly or subcutaneously), intracisternally, intravaginally, interperitoneally, locally (powders, ointments or drops), or as a buccal or by inhalation (nebulized, or as nasal sprays).

Compositions suitable for parenteral injection may comprise physiologically acceptable sterile aqueous or nonaqueous solutions, stabilizers, antioxidants, preservatives (e.g. ascorbic acid, sodium sulfite, sodium hydrogene sulfite, benzyl alcohol, EDTA), dispersions, suspensions or emulsions and sterile powders for reconstitution into sterile injectable solution or dispersion. Examples of suitable aqueous and nonaqueous carriers, diluents, solvents or vehicles include water, ethanol, polyol, (propylene glycol, polyethylene glycol, glycerol and the like), suitable mixtures thereof, vegetable oils (such as olive or canola oil) and injectable organic esters such as ethyl oleate. Proper fluidity can be maintained, for examples, by the use of a coating such as lecithin, by the maintenance of the required particle size in the case of dispersions and by the use of surfactants.

These compositions may also contain adjuvants such as preserving, wetting, emulsifying, and dispersing agents. Prevention of the actions of microorganisms can be ensured by various antibacterial and antifungal agents, for examples, parabens, chlorobutanol, phenol, sorbic acid, and the like. It may also be desirable to include isotonic agents, for examples sugars, sodium chloride and the like. Prolonged absorption of the injectable pharmaceutical form can be brought about by the use of agents delaying absorption, for examples aluminium monostearate and gelatin.

If desired, and for more effective distribution, the compounds can be incorporated into slow or timed release or targeted delivery systems such as polymer matrices, liposomes, and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound or a prodrug ester is admixed with at least one inert customary excipient (or carrier) such as sodium citrate or dicalcium phosphate or (i) fillers or extenders, as for example, starches, lactose, sucrose, glucose, mannitol and silicic acid, (ii) binders, as for example, carboxymethylcellulose, alginates, gelatine, polyvinylpyrrolidone, sucrose and acacia, (iii) humectants, as for example, glycerol, (div disintegrating agents, as for example, agar-agar, calcium carbonate, potato or tapioca starch, aliginic acid, certain complex silicates and sodium carbonate, (v) solution retarders, as for examples, paraffin, (vi) absorption accelerators, as for example, quaternary ammonium compounds, (vii) wetting agents; as for examples, cetyl alcohol and glycerol monostearate, (viii) adsorbents, as for example, kaolin and bentonite, and (ix) lubricants, as for example, talc, calcium stearate, magnesium stearate, solid polyethylene glycols, sodium lauryl sulfate and mixtures thereof. In the case of capsules, tablets, and pills, the dosage forms may also comprise buffering agents.

Solid compositions of a similar type may also be employed as fillers in soft and hard-filled gelatine capsules using excipients as lactose or milk sugars as well as high molecular polyethylene glycols and the like. Solid dosage forms such as tablets, dragées, capsules, pills and granules can be prepared with coatings and shells, such as enteric coatings and others well known in the art. They may contain opacifying agents, and can also be of such compositions that they release the active compound or compounds in a certain part of the intestinal tract in a delayed manner. Examples of embedding compositions that can be used are polymeric substances and waxes. The active compounds can also be in microencapsulated form, if appropriate, with one or more of the above-mentioned excipients Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, cannola oil, caster oil and sesame seed oil, glycerol, tetrahydrofurfuryl alcohol, polyethylene glycols and fatty acid esters of sorbitan or mixtures of these substances, and the like. Besides such inert diluents, the compositions can also include adjuvants, such as wetting agents, emulsifying and suspending agents, sweeting, flavouring and perfuming agents.

Suspensions, in addition to the active compounds, may contain suspending agents, for example, ethoxylated isostearyl alcohols, polyoxyethylene sorbitol and sorbitan esters, microcrystalline cellulose, aluminium metahydroxide, bentonite, agar-agar, tragacanth or mixtures of these substances and the like.

Compositions for rectal administrations are preferably suppositories, which can be prepared by mixing the compounds of the present invention with suitable nonirritating excipients or carriers such as cacao butter, polyethylene glycol or a suppository wax, which are solid at ordinary temperatures but liquid at body temperature and therefore melt in the rectal or vaginal cavity and release the active component. Dosage forms for topical administration of a compound of this invention include ointments, powder, sprays and inhalants.

The active component is admixed under sterile conditions with a physiologically acceptable carrier and any needed preservatives, buffers or propellants as may be required. Ophthalmic formulations, eye ointments, suspensions, powder and solutions are also contemplated as being within the scope of this invention.

The compounds of the present invention can also be incorporated into or connected to liposomes or administrated in the form of liposomes. As is known in the art, liposomes are generally derived from phospholipids or other lipid substances. Liposomes are formed by mono or multilamellar hydrated liquid crystals that are dispersed in an aqueous medium. Any non-toxic, physiologically acceptable metabolized lipid capable of forming liposomes can be used. The present compositions in liposome form can contain, in addition to the selectin binding inhibitors of the present invention, stabilizers, preservatives, excipients and the like. The preferred lipids are the phospholipids and the phosphatidyl cholines (lecithins), both natural and synthetic. Methods to form liposomes are well known in the art.

Non-parenteral dosage forms may also contain a bioavailability enhancing agent (e.g. enzyme inhibitors, antioxidants) appropriate for the protection of the compounds against degradation. Actual dosage levels of active ingredient in the composition of the present invention may be varied so as to obtain an amount of active ingredient that is effective to obtain the desired therapeutic response for a particular composition and method of administration. The selected dosage level, therefore, depends on the desired therapeutic effect, on the route of administration, on the desired duration of treatment and other factors. The total daily dosage of the compounds on this invention administered to a host in single or divided doses may be in the range up to 50 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex diet, time and route of administration, rates of absorption and excretion, combination with other drugs and the severity of the particular disease being treated.

In particular, the compounds of the present invention may be used to treat a variety of diseases relating to inflammation and cell-cell recognition and adhesion. For example, the compounds of the present invention may be administrated to a patient to treat COPD, acute respiratory distress syndrome (ARDS), Crohn's disease, septic shock, chronic to inflammatory diseases such as psoriasis, atopic dermatitis, and rheumatoid arthritis, and reperfusion tissue injury that occurs following heart attacks, strokes, atherosclerosis, and organ transplants, traumatic shock, multi-organ failure, autoimmune diseases like multiple sclerosis, asthma and inflammatory bowel disease. In each case, an effective amount of the compounds of the present invention is administered either alone or as part of a pharmaceutically active composition to a patient in need of such treatment. It is also recognized that a combination of the compounds may be administered to a patient in need of such administration. The compounds of the present invention may also be administered to treat other diseases that are associated with cell-cell adhesion. As the present compounds inhibit the binding of E-selectin or P-selectin or L-selectin, any disease that is related to this interaction may potentially be treated by the inhibition of this binding interaction.

In addition to being found on some white blood cells, sLe$^a$ is found on various cancer cells, including lung and colon cancer cells. It has been suggested that cell adhesion involving sLe$^a$ may be involved in the metastasis of certain cancers and inhibitors of sLe$^a$ binding might be useful in treatment of some forms of cancer.

Many of the compounds of the present invention may be synthesized according to the following general synthetic schemes.

SCHEME 1

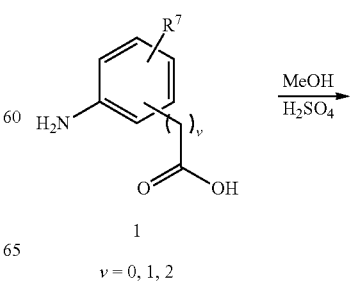

$v = 0, 1, 2$

-continued

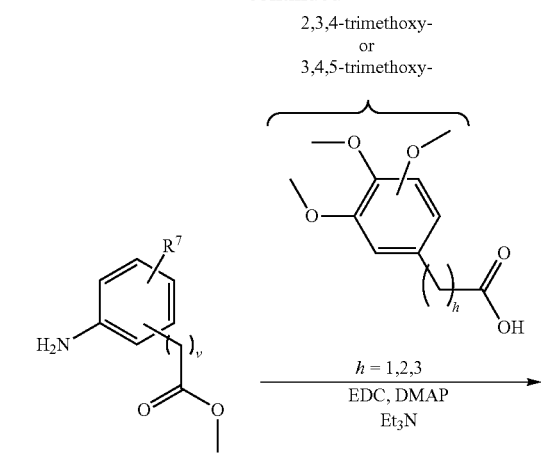

2

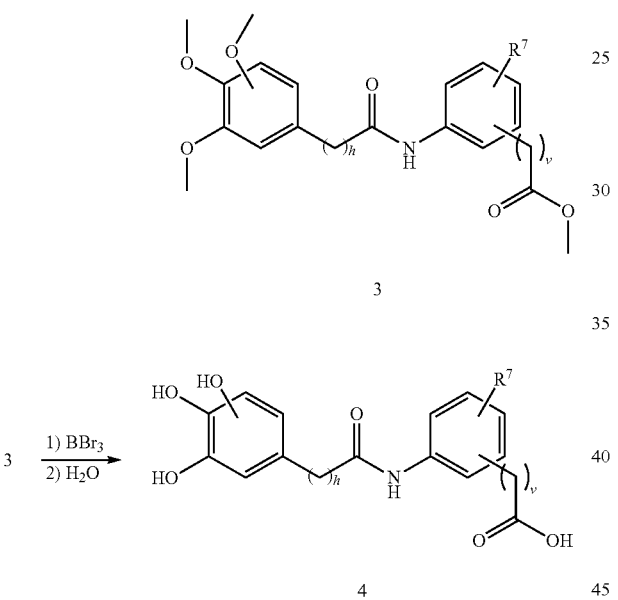

3

4

SCHEME 2

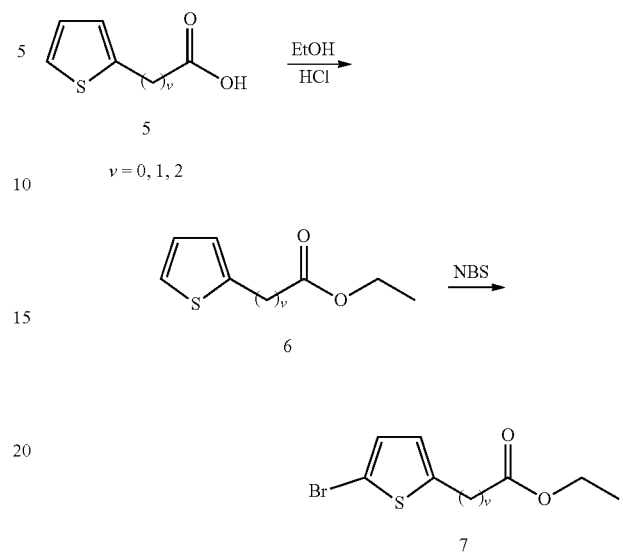

In SCHEME 1 an amino acid of type (1) is reacted to the corresponding methyl ester (2) under heating with acidic methanol. Ester (2) is reacted with a trimethoxy-phenyl-alkylic acid under state-of-the-art conditions (i.e. N'-(3-dimethylaminopropyl)-N-ethyl carbodiimide (EDC), triethylamine and 4-dimethylaminopyridine (DMAP) in a chlorinated solvent) to the amide (3). Alternatively diisopropyl carbodiimide (DIC) and hydroxybenzotriazole (HOBt) may be used for this reaction step. Amide (3) is converted to acid (4) by treating it with an excess of boron tribromide at −78° C. up to rt in a halogenated solvent followed by aqueous workup. However, in some cases it may be necessary to hydrolize the ester (3) with i.e. aqueous lithium hydroxide in acetonitrile before treating it with boron tribromide. The synthesis sequence shown in SCHEME 1 leading to compounds like (4) is not only reduced to the Y—H building blocks like (1) but may be generally applied to all other Y—H type building blocks leading to compounds of type (A1), (A2), (B1) and (B2) as shown in the paragraph before.

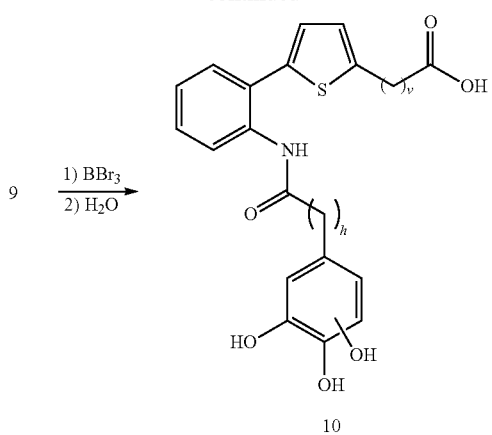

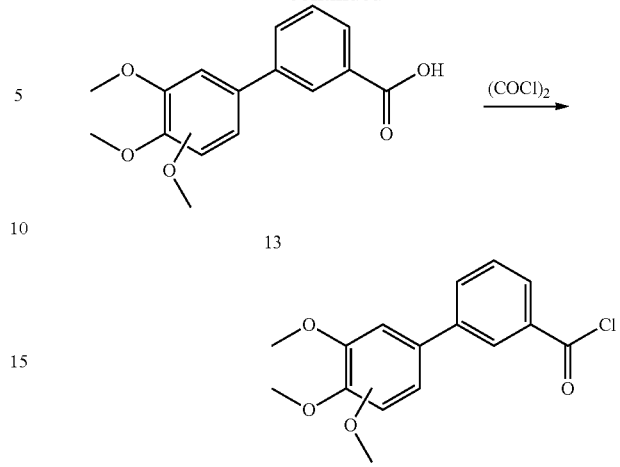

In SCHEME 2 a carboxy substituted thiophene like (5) is reacted to the corresponding ethyl ester (6) under heating in acidic ethanol. Ester (6) is brominated with N-bromosuccinimide in anhydrous chloroform and glacial acetic acid to give (7) which is further reacted with 2-Amino-benzeneboronic acid under a state-of-the-art Suzuki transformation (i.e. Tetrakis(triphenylphosphine)-palladium, aqueous sodium carbonate, ethanol, toluene) to the biaryl (8). Biaryl (8) is reacted with a trimethoxy-phenyl-alkylic acid, EDC, triethylamine and DMAP in a chlorinated solvent to the amide (9). Alternatively DIC and HOBt may be used for this reaction step. Amide (9) is converted to acid (10) by treating it with an excess of boron tribromide at −78° C. up to rt in a halogenated solvent followed by aqueous workup. However, in some cases it may be necessary to hydrolize the ester (9) with i.e. aqueous lithium hydroxide in acetonitrile before treating it with boron tribromide.

In SCHEME 3 Methyl-3-bromobenzoate (11) is reacted under inert conditions with a Trimethoxyphenylboronic acid under Suzuki-type basic conditions ($Pd(PPh_3)_4$ and aqueous sodium bicarbonate in dimethoxymethane) to a biphenyl of type (12) which is further hydrolized with aqueous lithium hydroxide in acetonitrile to give the corresponding carboxylic acid (13) which was converted to building block of type (14) by reaction with oxalyl chloride in anhydrous dichloromethane.

SCHEME 4

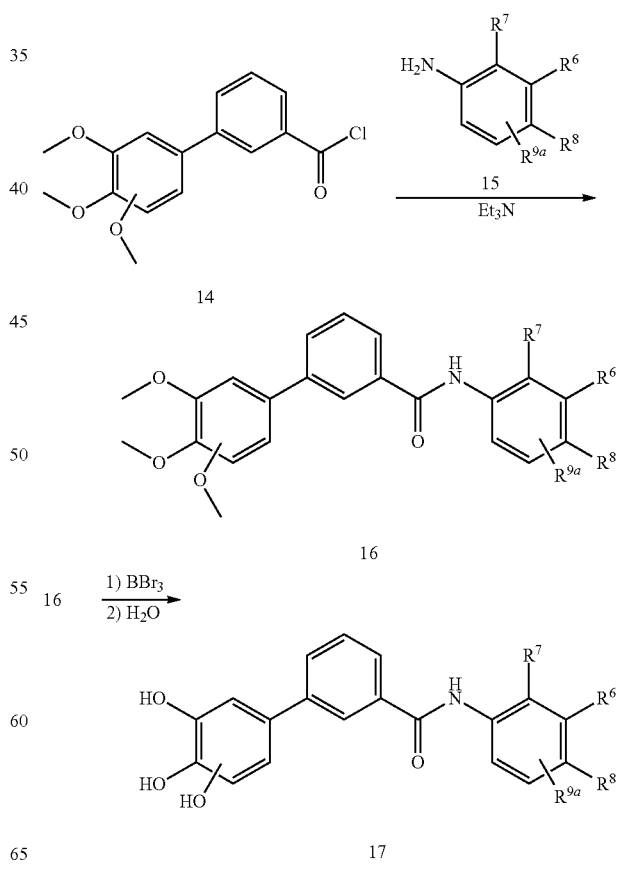

SCHEME 3

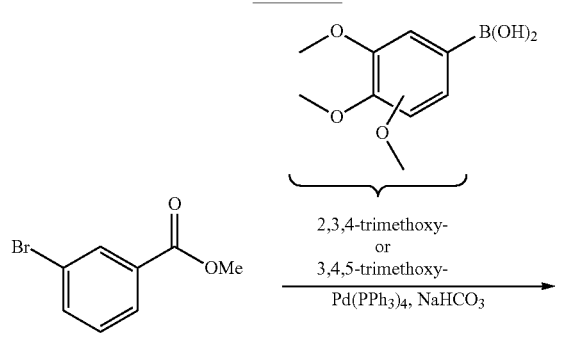

In SCHEME 4 an acid chloride like (14) is reacted with an aniline of general type (15) under basic conditions (triethylamine in a chlorinated solvent) to form the anilide (16).

Alternatively pyridine may be used for this reaction step. Anilide (16) is converted to trihydroxyphenyl (17) by treating it with an excess of boron tribromide at −78° C. up to rt in a halogenated solvent followed by aqueous workup.

In case that $R^6$ and/or $R^8$ contain carboxylic acid functionalities, those are protected as their corresponding methyl or ethyl esters before and hydrolized afterwards to release the carboxylic acid functionalities. The ester hydrolysis was done whether with LiOH in MeCN or THF/MeOH or under treatment with $BBr_3$ in followed by addition of water.

The synthesis sequence shown in SCHEME 4 leading to compounds like (17) is not only reduced to X—Y—H and Y—H building blocks like (15) but may be generally applied to all other X—Y—H and Y—H type building blocks leading to compounds of type (A1), (A2), (B1) and (B2) as shown in the paragraphs before.

SCHEME 5

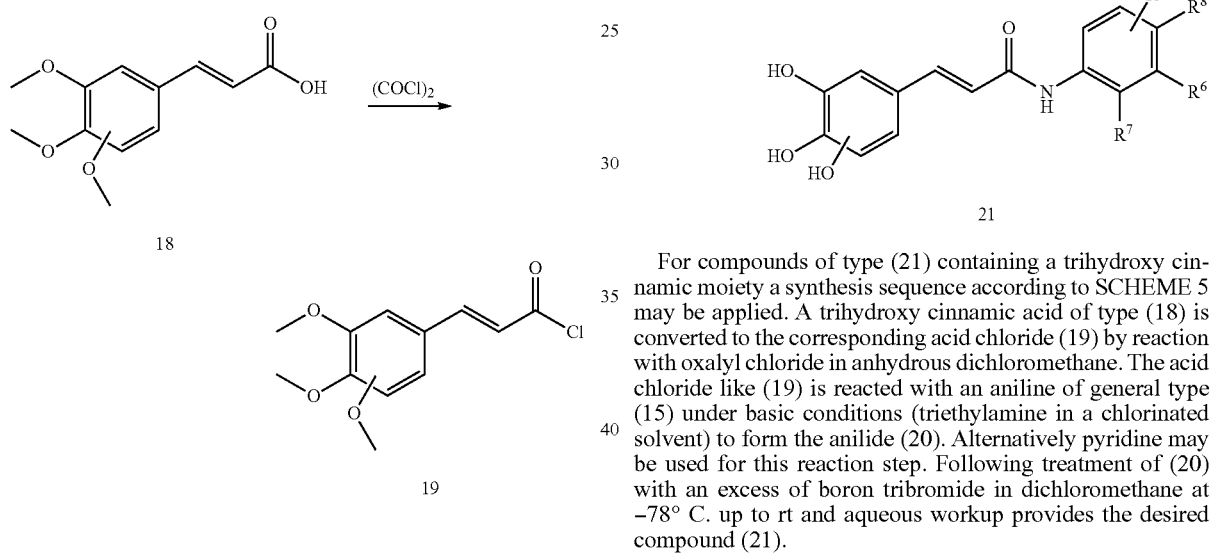

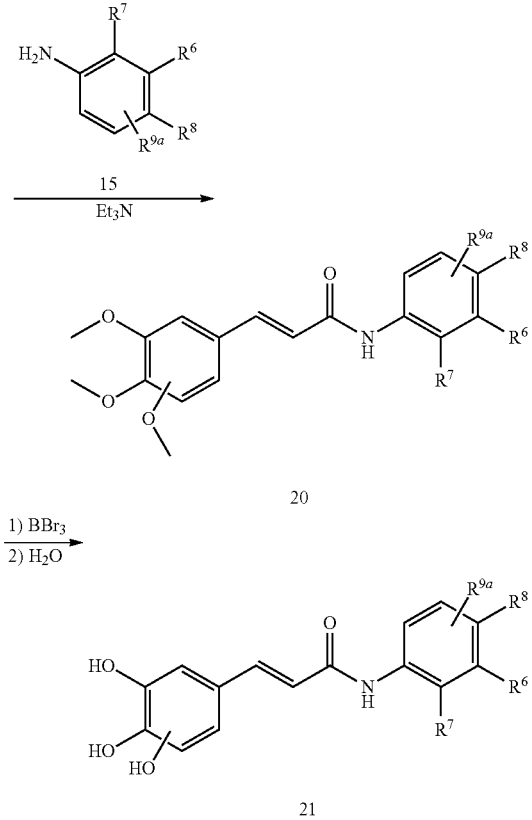

For compounds of type (21) containing a trihydroxy cinnamic moiety a synthesis sequence according to SCHEME 5 may be applied. A trihydroxy cinnamic acid of type (18) is converted to the corresponding acid chloride (19) by reaction with oxalyl chloride in anhydrous dichloromethane. The acid chloride like (19) is reacted with an aniline of general type (15) under basic conditions (triethylamine in a chlorinated solvent) to form the anilide (20). Alternatively pyridine may be used for this reaction step. Following treatment of (20) with an excess of boron tribromide in dichloromethane at −78° C. up to rt and aqueous workup provides the desired compound (21).

SCHEME 6

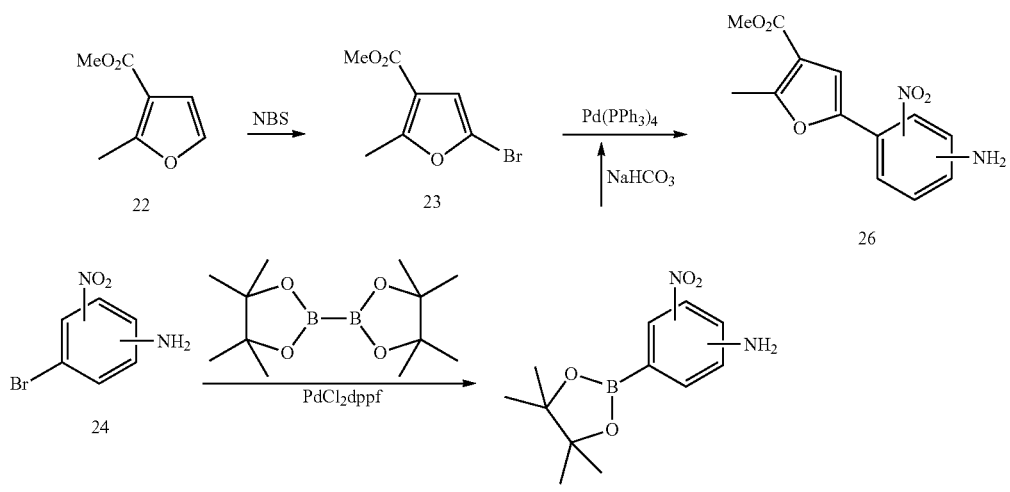

In SCHEME 6 the generation of building block (26) is outlined, whereby the furane (23) is available by NBS-bromination of methyl furoate (22) and pinacolyl borane of type (25) is available by Pd-catalyzed boration of anilines like (24). Suzuki-type coupling of (23) and (25) with Pd(PPh$_3$)$_4$ leads to biaryls of type (26).

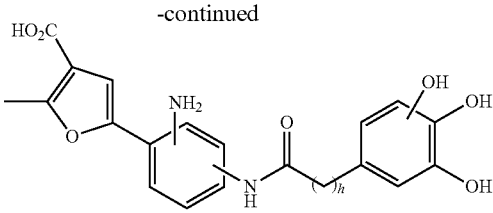

30

In SCHEME 7 a biaryl of type (26) is reacted with a trimethoxy-phenyl-alkylic acid under state-of-the-art conditions (i.e. N'-(3-dimethylaminopropyl)-N-ethyl carbodiimide (EDC), triethylamine and 4-dimethylaminopyridine (DMAP) in a chlorinated solvent) to the amide of type (27). Alternatively diisopropyl carbodiimide (DIC) and hydroxybenzotriazole (HOBt) may be used for this reaction step. (27) is then hydrolized to acid of type (28) whether with LiOH in MeCN or THF/MeOH. Treatment of (28) with an excess of boron tribromide in dichloromethane at −78° C. up to rt and aqueous workup provides compounds (29) which are finally hydrogenated with Pd on Carbon and ammonium formate to the desired compounds of general structure (30).

The present invention is furthermore illustrated by the following representative examples.

EXAMPLE 1

{3-[3-(2,3,4-Trihydroxy-phenyl)-propionylamino]-phenyl}-acetic acid (34)

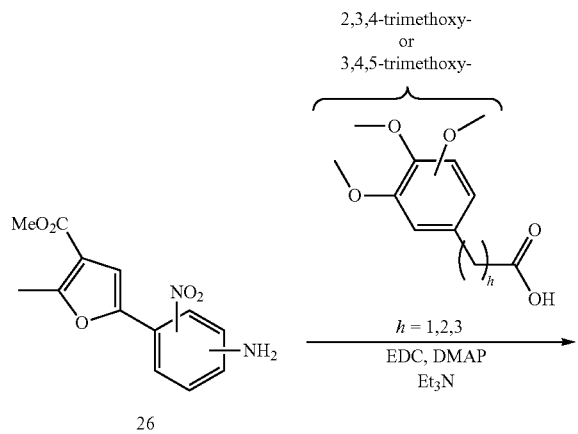

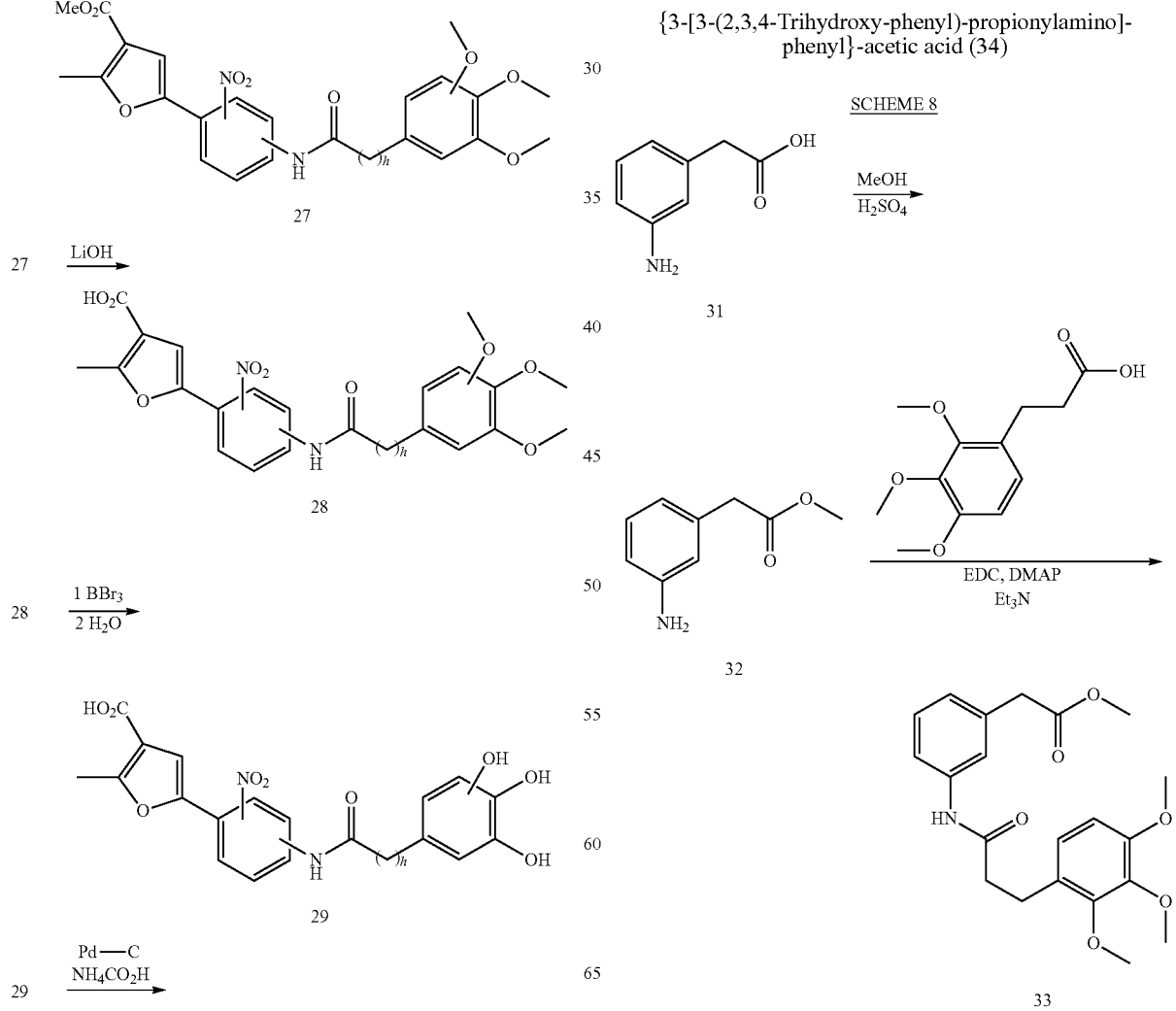

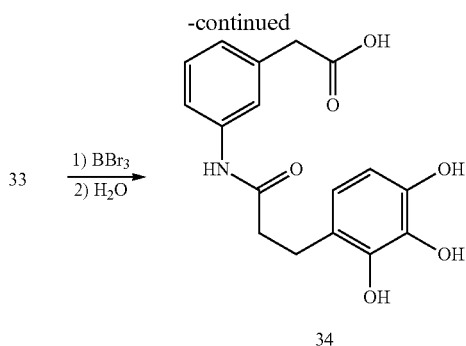

Step 1:
Dissolve (3-Amino-phenyl)-acetic acid ((31), 700 mg, 4.63 mmol) in MeOH (21 mL) and add conc. sulfuric acid (0.27 mL, 5.09 mmol). Stir the reaction mixture for 2d under reflux. Cooled mixture to room temperature (rt), remove solvent under reduced pressure and prepurify the residue by flushing it over a short pad of silica gel using EtOAc.

Remove solvent again and partition the residue between EtOAc and saturated aqu. NaHCO$_3$ (1+1). Extracte the aqueous layer 3 times with EtOAc, washe the combined organic layers with brine and dried with Na$_2$SO$_4$. Remove solvent under reduced pressure and dry the residue without further purification in oil pump vacuum to obtain product (32) as a light yellow oil (708 mg, 92%). $^1$H NMR (400 MHz, CDCl$_3$): 3.51 (s, 2H); 3.67 (s, 3H); 6.57 (dd, 1H, J=7.8 Hz, J$_2$=1.8 Hz); 6.60 (br.Ψt, 1H, J=1.8 Hz); 6.65 (br.d, 1H, J=7.8 Hz); 7.08 (Ψt, 1H, J=7.8 Hz).

Step 2:
(The following reaction is done in an anhydrous N$_2$ atmosphere.) Dissolve EDC hydrochloride (187 mg, 0.98 mmol) and triethylamine (0.14 mL, 1.00 mmol) in anhydrous dichloromethane (3.5 mL) and stir for 5 min at rt. Added 3-(2,3,4-Trimethoxy-phenyl)-propionic acid (234 mg, 0.97 mmol) and DMAP (12 mg, 0.10 mmol) and stir for 10 min. Add ester (32) (107 mg, 0.65 mmol) and stir the reaction solution overnight at rt.

Hydrolize the reaction solution with saturated aqu. NH$_4$Cl followed by water, separate layers, extracte aqu. layer with dichloromethane (3 times) and washe the combined organic layers with water and brine and dry with Na$_2$SO$_4$. Remove solvent under reduced pressure.

Purify crude product by preparative radial chromatography (silica gel 60 PF, EtOAc/CyH 1+1) to obtain product (33) as a white solid (209 mg, 83%). [K. C. Nicolaou; P. S. Baran; Y.-L. Zhong; K. Sugita; *J. Am. Chem. Soc.;* 2002; 124; 10; 2212-2220]. $^1$H NMR (400 MHz, CDCl$_3$): 2.62 (t, 2H, J=7.5 Hz); 2.95 (t, 2H, J=7.5 Hz); 3.58 (s, 2H); 3.67 (s, 3H); 3.82 (s, 3H); 3.84 (s, 3H); 3.91 (s, 3H); 6.59 (d, 1H, J=8.6 Hz); 6.86 (d, 1H, J=8.6 Hz); 6.98 (br.d, 1H, J=7.8 Hz); 7.32 (Ψt, 1H, J=7.8 Hz); 7.38 (br.d, 1H, J=7.8 Hz); 7.41 (br.s, 1H).

Step 3:
(The following reaction is done in an anhydrous N$_2$ atmosphere.) Dissolve (33) (139 mg, 0.36) in anhydrous dichloromethane (1.8 mL), cooled to −78° C. (acetone/dry ice bath) and add slowly BBr$_3$ (0.51 mL, 5.39 mmol). Stir the reaction mixture for additional 30 min at −78° C. Remove cooling bath and stir the reaction mixture for 3 h at rt.

Cool reaction mixture to 0° C., add slowly water (0.50 mL) under vigorous stirring followed by dichloromethane (1.0 mL) and methanol (2.0 mL). Extract the mixture with EtOAc (3 times) and dry the combined organic layers with Na$_2$SO$_4$. Remove solvent under reduced pressure and purify crude product by preparative RP HPLC (gradient, water/MeCN 95:5 to 5:95) to obtain {3-[3-(2,3,4-Trihydroxy-phenyl)-propionylamino]-phenyl}-acetic acid (34) as a white solid (69 mg, 57%). [T. P. Kogan; B. Dupré; H. Bui; K. L. McAbee; J. M. Kassir; I. L. Scott; X. Hu; P. Vanderslice; P. J. Beck; R. A. F. Dixon *J. Med. Chem.;* 1998; 41; 1099-1111]. $^1$H NMR (400 MHz, CD$_3$OD): 2.67 (t, 2H, J=7.6 Hz); 2.92 (t, 2H, J=7.6 Hz); 3.61 (s, 2H); 6.31 (d, 1H, J=8.3 Hz); 6.50 (d, 1H, J=8.3 Hz); 7.05 (br.d, 1H, J=7.8 Hz); 7.28 (Ψt, 1H, J=7.8 Hz); 7.48 (br.d, 1H, J=7.8 Hz); 7.49 (br.s, 1H).

EXAMPLE 2

(5-{2-[(2-(2,3,4-Trihydroxyphenyl)-acetylamino]-phenyl}-thiophen-2-yl]acetic acid (41)

SCHEME 9

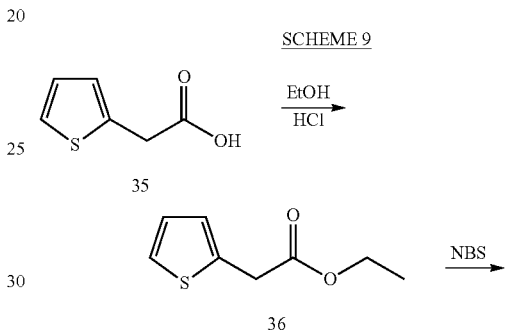

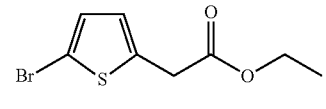

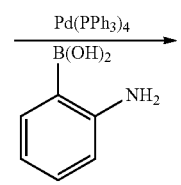

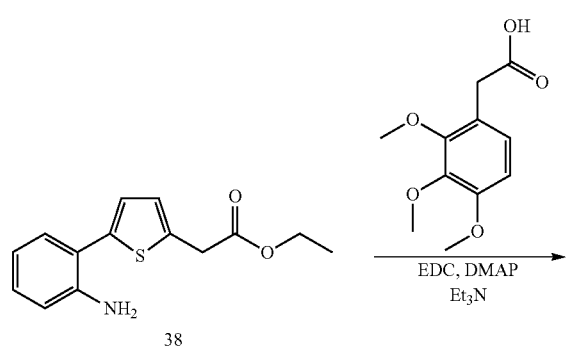

-continued

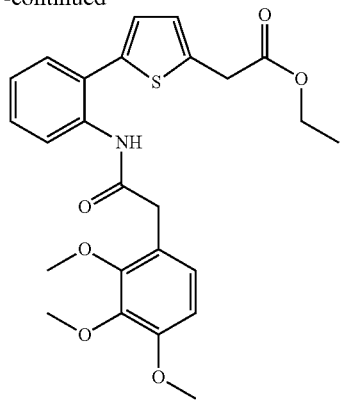

39

39 →(LiOH)

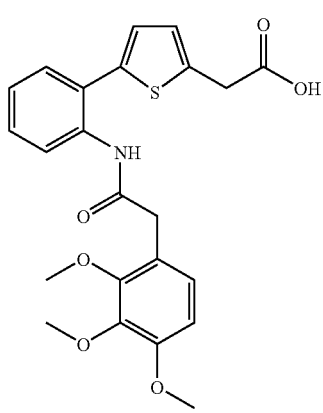

40

1) BBr₃
2) H₂O

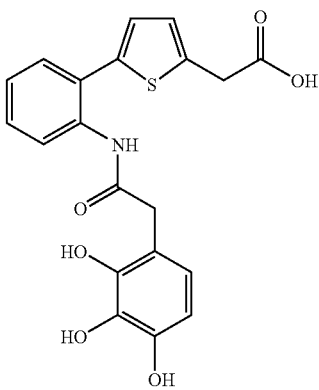

41

Step 1:

Dissolve Thiophene-2-yl-acetic acid (35) (2.44 g, 17.1 mmol) in ethanol (35 mL) and add fuming aqu. hydrochloric acid (few drops). Stir the reaction mixture for 19 h at 70° C. Cool mixture to rt, remove solvent under reduced pressure and resolve the residue in EtOAc. Wash this organic layer 3 times with 5% aqu. $Na_2CO_3$ and extract the combined aqueous layer 3 times with EtOAc. Wash the combined organic layers with brine and dry with $Na_2SO_4$. Remove solvent under reduced pressure and dry the residue without further purification in oil pump vacuum to obtain product (36) as a light brown oil (2.78 g, 95%). [J. Kunes; V. Balsanek; M. Pour; V. Buchta; *Collect. Czech. Chem. Commun.*, 2001, 66; 12; 1809-1830]. ¹H NMR (400 MHz, $CDCl_3$): 1.26 (t, 3H, J=7.1 Hz); 3.81 (s, 2 H); 4.17 (q, 2H, J=7.1 Hz); 6.91-6.96 (m, 2H); 7.20 (d, 1H, J=4.8 Hz).

Step 2:

(The following reaction is done in an anhydrous $N_2$ atmosphere.) Dissolve ester (36) (1.30 g, 7.64 mmol) in anhydrous chloroform (6.0 mL) and glacial acetic acid (6.0 mL), add N-Bromosuccinimide (1.39 g, 7.79 mmol) in portions and stir the mixture for 23 h at rt. The mixture is diluted with an equal volume of water, the organic layer separated and washed with a 1M aqu. NaOH, water, again with 1M aqu. NaOH and water (2 times). Finally wash the organic layer with brine and dry with $Na_2SO_4$. Remove solvent under reduced pressure. Purify crude product by preparative radial chromatography (silica gel 60 PF, CyH/EtOAc 5+1] to obtain product (37) as an impured (according to NMR: 20% sideproduct) orange liquid (1.61 g, 85%) which is used without any further purification. [P. M. Jackson; C. J. Moody; P. Sha; *J. Chem. Soc. Perkin Trans.* 1; 1990; 2909-2918]. ¹H NMR (400 MHz, $CDCl_3$): 1.26 (t, 3H, J=7.1 Hz), 3.73 (s, 2H); 4.17 (q, 2H, J=7.1 Hz); 6.67 (d, 1H, J=3.5 Hz); 6.88 (d, 1H, J=3.5 Hz).

Step 3:

(The following reaction is done in an oxygenfree $N_2$ atmosphere.) Ethanol (1.47 mL), Tetrakis-(triphenylphosphine)-palladium(0) (59.0 mg, 2.5 mol %) and aqu. $Na_2CO_3$ (1.60 g, 5.60 mmol; presolved in 2.0 mL $H_2O$) are subsequently added to dissolved 2-Amino-benzeneboronic acid (341 mg, 2.20 mmol) in toluene (16 mL). The reaction mixture is degassed 5 times and flooded with $N_2$ again. Add bromide (37) (498 mg, 2.00 mmol) and rinse with toluene (4.5 mL), degas again (5 times) and stir the reaction solution 21 h at 100° C. Partition the reaction solution between EtOAc and brine (1+1) and extract the separated aqueous layer 3 times with EtOAc. Wash combined organic layer with brine and dry with $Na_2SO_4$. Remove solvent under reduced pressure and purify the crude product by preparative radial chromatography (silica gel 60 PF, CyH/EtOAc 6+1, later 3+1] to obtain product (38) as a light yellow solid (300 mg, 57%). [N. Miyaura; A. Suzuki; *Chem. Rev.*; 1995; 95; 2457]. ¹H NMR (400 MHz, $CDCl_3$): 1.28 (t, 3H, J=7.1 Hz); 3.82 (s, 2H); 4.19 (q, 2H, J=7.1 Hz); 6.77-6.84 (m, 2H); 6.91 (d, 1H, J=3.5 Hz); 7.04 (d, 1H, J=3.5 Hz); 7.13 (td, 1H, J=7.8 Hz, 1.3 Hz); 7.25 (d, 1H, J=7.8 Hz).

Step 4:

(The following reaction is done in an anhydrous $N_2$ atmosphere.) Suspend EDC hydrochloride (86.3 mg, 0.45 mmol) in anhydrous dichloromethane (1.4 mL), add triethylamine (0.063 mL, 0.45 mmol) and stir for 10 min at rt. Add 2-(2,3,4-Trimethoxy-phenyl)-acetic acid (74.7 mg, 0.33 mmol) and DMAP (3.7 mg, 0.03 mmol) and stir for 15 min Added ester (38) (64.9 mg, 0.30 mmol) and stir the reaction solution 22 h at rt. Partition the reaction solution between dichloromethane and water (1+1), separate layers and extract aqu. layer with dichloromethane (3 times). Wash the combined organic layer with brine and dry with $Na_2SO_4$. Purify crude product by preparative radial chromatography (silica gel 60 PF, CyH/EtOAc 3+2) to obtain product (39) as yellow oil (118 mg, 84%). ¹H NMR (400 MHz, $CDCl_3$): 1.29 (t, 3H, J=7.1 Hz); 3.58 (s, 2H); 3.74 (s, 3H); 3.78 (s, 3H); 3.79-3.80 (m, 2H); 3.86 (s, 2H); 4.20 (q, 2H, J=7.1 Hz); 6.58 (d, 1H, J=8.6 Hz); 6.59 (d, 1H, J=3.5 Hz); 6.75 (d, 1H, J=3.5 Hz); 6.85 (d, 1H, J=8.6 Hz); 7.05 (t, 1H, J=7.8 Hz); 7.26 (dd, 1H, J=7.8 Hz, 1.3 Hz); 7.30 (td, 1H, J=7.8 Hz, 1.3 Hz); 7.90 (br.s; 1H), 8.38 (d, 1H, J=8.3 Hz).

Step 5:

Dissolve ester (39) (118 mg, 0.25 mmol) in methanol (8.0 mL), add a 1M aqu. LiOH solution (1.76 mL, 1.76 mmol) and stir 20 h at rt. Remove solvent under reduced pressure and partition residue between CHCl₃ and 0.5M HCl (1+1). Separate the aqueous layer and extract 3 times with CHCl₃. Wash the combined organic layer with brine and dry with Na₂SO₄. Remove solvent under reduced pressure and dry the residue without further purification in oil pump vacuum to obtain crude product (40) as light brown foam (120 mg, quant.). ¹H NMR (400 MHz, CDCl₃): 3.58 (s, 2H); 3.73 (s, 3H); 3.78 (s, 3H); 3.85 (s, 2 H); 3.86 (s, 3H); 6.58-6.61 (m, 1H); 6.59 (d, 1H, J=8.3 Hz); 6.77 (d, 1H, J=3.5 Hz); 6.86 (d, 1H, J=8.3 Hz); 7.06 (t, 1H, J=7.8 Hz); 7.22-7.27 (m, 1H); 7.31 (td, 1H, J=7.8 Hz, 1.3 Hz); 7.86 (br.s, 1H); 8.37 (d, 1H, J=8.3 Hz).

Step 6:

(The following reaction is done in an anhydrous N₂ atmosphere.) Dissolve (40) (118 mg, 0.27 mmol) in anhydrous dichloromethane (2.5 mL), cool to −78° C. (acetone/dry ice) and add slowly a 1M BBr₃ solution in dichloromethane (1.61 mL, 1.61 mmol). Stir the reaction mixture for additional 30 min at −78° C. Remove cooling bath and stir the reaction mixture for 4 h at rt. Cool reaction mixture to 0° C., add slowly water (1.00 mL) under vigorous stirring. Partition the reaction mixture between EtOAc and water (1+1). Extract the separated aqueous layer with EtOAc (2 times) and wash the combined organic layer with brine and dry with Na₂SO₄. Remove solvent under reduced pressure and purify crude product by preparative RP HPLC (gradient, water/CH₃CN 95:5 to 5:95) to obtain (5-{2-[2-(2,3,4-Trihydroxyphenyl)-acetylamino]-phenyl}-thiophen-2-yl)acetic acid (41) as a light brown foam (53 mg, 50%). ¹H NMR (400 MHz, CDCl₃): 3.54 (s, 2H); 3.82 (s, 2H); 6.34 (d, 1H, J=8.3 Hz); 6.49 (d, 1H, J=8.3 Hz); 6.76 (d, 1H, J=3.3 HZ); 6.81 (d, 1H, J=3.3 Hz); 7.18 (t, 1H, J=7.6 Hz); 7.32 (t, 1H, J=7.8 Hz); 7.39 (d, 1H, J=7.3 Hz); 7.90 (d, 1H, J=8.1 Hz); 8.20 (br.s, 1H).

EXAMPLE 3

(5-{2-[(2',3',4'-Trihydroxy-biphenyl-3-carbonyl)-amino]-phenyl}-thiophen-2-yl)-acetic acid (48) and (5-{2-[(2',3',4'-Trihydroxy-biphenyl-3-carbonyl)-amino]-phenyl}-thiophen-2-yl)-acetic acid methyl ester (49)

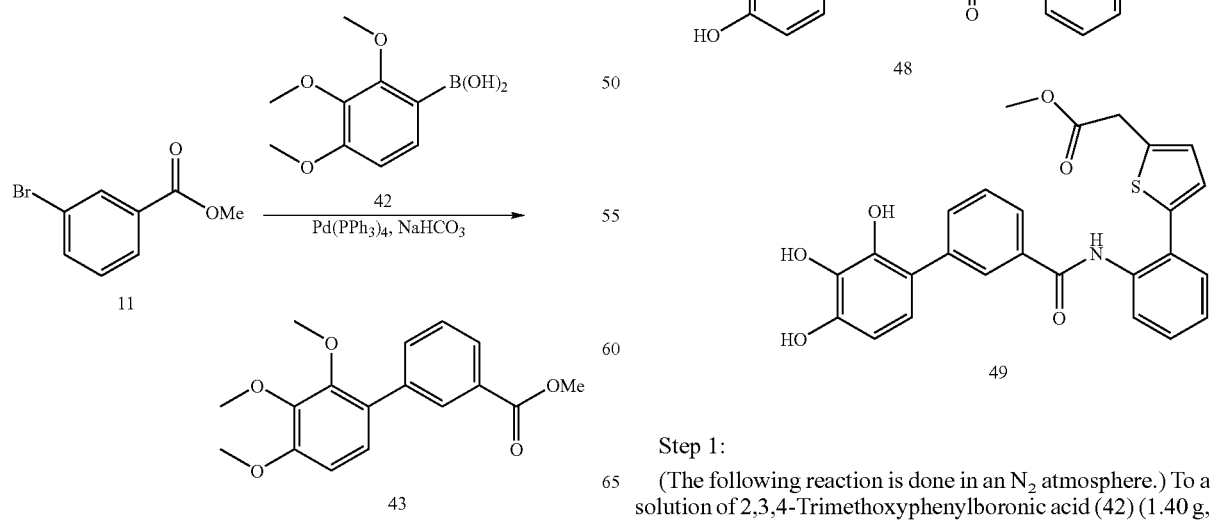

Step 1:

(The following reaction is done in an N₂ atmosphere.) To a solution of 2,3,4-Trimethoxyphenylboronic acid (42) (1.40 g, 6.60 mmol) in toluene (15.0 mL) is added EtOH (2.0 mL), Pd(PPh$_3$)$_4$ (208 mg, 0.18 mmol) and Na$_2$CO$_3$.10H$_2$O (4.81 g, 16.80 mmol) in water (5.2 mL). The resulting mixture is carefully degassed (5 times alternating vacuum and flushing with N$_2$). A solution of Methyl-3-bromobenzoate (11) (1.29 g, 6.00 mmol) in toluene (9.0 mL) is added by syringe, the resulting mixture is again carefully degassed and stirred overnight at 100° C. Partition the mixture between brine/EtOAc (1+1), separate layers, extract the aqu. layer with EtOAc (3×), wash the combined organic layer with brine, dry with Na$_2$SO$_4$ and remove solvent. Purify crude product by preparative radial chromatography (silica gel, EtOAc/CyH 1+5) to obtain 2',3',4'-Trimethoxy-biphenyl-3-carboxylic acid methyl ester (43) as a yellowish oil (1.07 g, 58%). $^1$H NMR (400 MHz, CDCl$_3$): 3.66 (s, 3H); 3.89 (s, 3H); 3.92 (s, 6H); 6.74 (d, 1H, J=8.6 Hz); 7.03 (d, 1H, J=8.6 Hz); 7.44 (t, 1H, J=7.8 Hz); 7.70 (d, 1H, J=7.6 Hz); 7.97 (d, 1H, J=7.8 Hz); 8.15 (br.s 1H).

Step 2:

Dissolve 2',3',4'-Trimethoxy-biphenyl-3-carboxylic acid methyl ester (43) (566 mg, 1.87 mmol) in MeCN (19.0 mL) at rt and add 1M aqu LiOH (9.36 mL, 9.36 mmol). Stir reaction mixture overnight at rt. Quench reaction mixture (cooling bath) with 1M aqu. HCl (to get pH ca. 3). Extract the mixture with EtOAc (3×), wash the combined organic layer with brine and dry with Na$_2$SO$_4$. Recrystallize crude product from EtOAc/CyH 1+3 to obtain 2',3',4'-Trimethoxy-biphenyl-3-carboxylic acid (44) as a white solid (392 mg, to 72%). $^1$H NMR (400 MHz, CD$_3$OD: 3.68 (s, 3H); 3.93 (br.s, 6H); 6.92 (d, 1H, J=8.6 Hz); 7.11 (d, 1H, J=8.6 Hz); 7.54 (t, 1H, J=7.7 Hz); 7.75 (d, 1H, J=7.6 Hz); 8.01 (d, 1H, J=7.8 Hz); 8.18 (br.s 1H).

Step 3:

(The following reaction is done in an anhydrous N$_2$ atmosphere.) Dissolve 2',3',4'-Trimethoxy-biphenyl-3-carboxylic acid (44) (107 mg, 0.37 mmol) in anhydrous DCM (3.0 mL) and add anhydrous DMF (3 drops, cat. amount). Then add slowly oxalyl chloride (42 μL, 0.48 mmol) by keeping temperature at ca. 15° C. with a water bath and stir the turbid mixture for additional 2 h at rt. Transfer the formed crude solution of 2',3',4'-Trimethoxy-biphenyl-3-carbonyl chloride (45) to an ice cooled solution of [5-(2-Amino-phenyl)-thiophen-2-yl]-acetic acid methyl ester (46) (70 mg, 0.28 mmol) in anhydrous DCM (4.5 mL) and anhydrous pyridine (0.75 mL). Stir the reaction mixture for 3 h at rt. Pour the reaction mixture into ice cooled 1M aqu. HCl, extract with DCM (3×), wash the combined organic layer with brine and dry with Na$_2$SO$_4$. Purify the crude product by preparative radial chromatography (silica gel, EtOAc/CyH 1+3, later 1+2) to obtain (5-{2-[(2',3',4'-Trimethoxy-biphenyl-3-carbonyl)-amino]-phenyl}-thiophen-2-yl)-acetic acid methyl ester (47) as a brownish sticky solid (96 mg, 65%). $^1$H NMR (400 MHz, CDCl$_3$): 3.64 (s, 3H); 3.71 (s, 3H); 3.84 (s, 2H); 3.90 (s, 3H); 3.92 (s, 3H); 6.75 (d, 1H, J=8.8 Hz); 6.97 (d, 1 H, J=3.5 Hz); 7.01 (d, 1H, J=8.8 Hz); 7.03 (d, 1H, J=3.5 Hz); 7.16 (br.t, 1H, J=7.6 Hz); 7.36-7.43 (m, 2H); 7.46 (t, 1H, J=7.7 Hz); 7.67 (Ψdd, 2H, J$_1$=7.6 Hz, J$_2$=1.5 Hz); 7.91 (br.s 1H); 8.41 (br.s 1H); 8.50 (d, 1H, J=8.6 Hz).

Step 4:

(The following reaction is done in an anhydrous N$_2$ atmosphere.) Dissolve (5-{2-[(2',3',4'-Trimethoxy-biphenyl-3-carbonyl)-amino]-phenyl}-thiophen-2-yl)-acetic acid methyl ester (47) (66 mg, 0.13 mmol) in anhydrous DCM (3.4 mL) at −78° C., add dropwise a 1M solution of BBr$_3$ in DCM (1.05 mL, 1.05 mmol) and stir for additional 30 min at −78° C. After slowly warming up stir the reaction solution for additional 4 h at rt. Cool reaction mixture to 0° C., add dropwise water and DCM under vigorous stirring followed by MeOH to homogenize the mixture. Partition the hydrolyzed reaction mixture between water and EtOAc, extract the aqu. layer with EtOAc (3×), wash combined organic layer with brine and dry it with Na$_2$SO$_4$. Purify the crude product by preparative RP HPLC (gradient, water/CH$_3$CN 95:5 to 5:95) to obtain (5-{2-[(2',3',4'-Trihydroxy-biphenyl-3-carbonyl)-amino]-phenyl}-thiophen-2-yl)-acetic acid (48) (8 mg, 13%) as a white solid and (5-{2-[(2',3',4'-Trihydroxy-biphenyl-3-carbonyl)-amino]-phenyl}-thiophen-2-yl)-acetic acid methyl ester (49) (14 mg, 23%) as a brown foam. $^1$H NMR (400 MHz, CD$_3$OD) (48): 3.86 (s, 2H); 6.49 (d, 1H, J=8.6 Hz); 6.74 (d, 1H, J=8.6 Hz); 6.98 (d, 1H, J=3.0 Hz); 7.19 (d, 1H, J=3.3 Hz); 7.36 (t, 1H, J=7.6 Hz); 7.43 (t, 1H, J=7.6 Hz); 7.51 (t, 1H, J=7.8 Hz); 7.62 (d, 1H, J=7.8 Hz); 7.71-7.84 (m, 3 Hz); 8.08 (br.s 1H); (49): 3.66 (s, 3H); 3.88 (s, 2H); 6.49 (d, 1H, J=8.3 Hz); 6.74 (d, 1H, J=8.3 Hz); 6.97 (d, 1H, J=3.5 Hz); 7.19 (d, 1H, J=3.5 Hz); 7.36 (td, 1H, J$_1$=7.6 Hz, J$_2$=1.5 Hz); 7.43 (td, 1H, J$_1$=7.6 Hz, J$_2$=1.5 Hz); 7.51 (t, 1H, J=7.8 Hz); 7.62 (dd, 1H, J$_1$=7.6 Hz, J$_2$=1.5 Hz); 7.73 (d, 1H, J=7.8 Hz); 7.81 (Ψdd, 2H, J$_1$=7.6 Hz, J$_2$=1.5 Hz); 8.09 (br.s 1H).

EXAMPLE 4

4-Methyl-3-[3-(2,3,4-trihydroxy-phenyl)-acryloylamino]-benzoic acid (54) and 4-Methyl-3-[3-(2,3,4-trihydroxy-phenyl)-acryloylamino]-benzoic acid methyl ester (55)

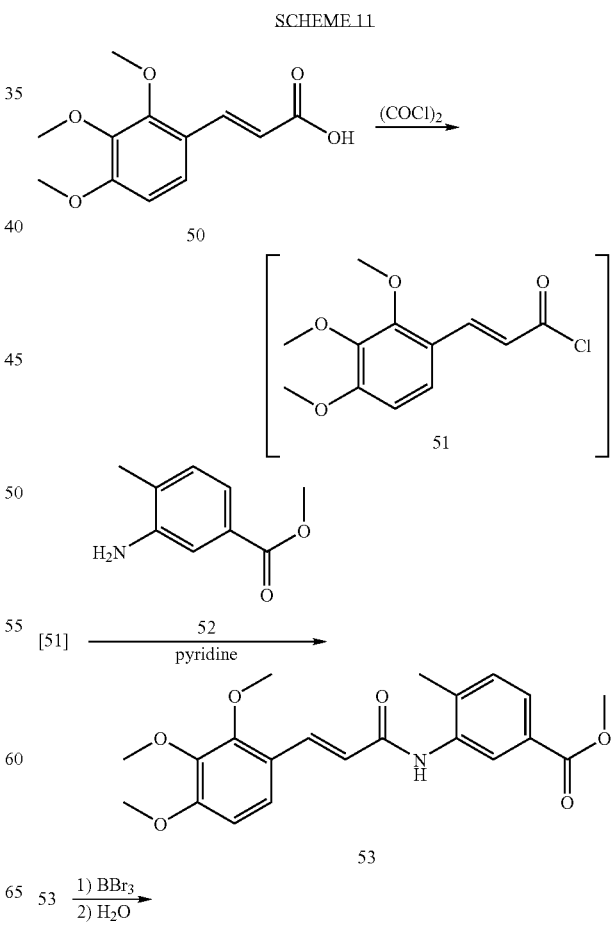

SCHEME 11

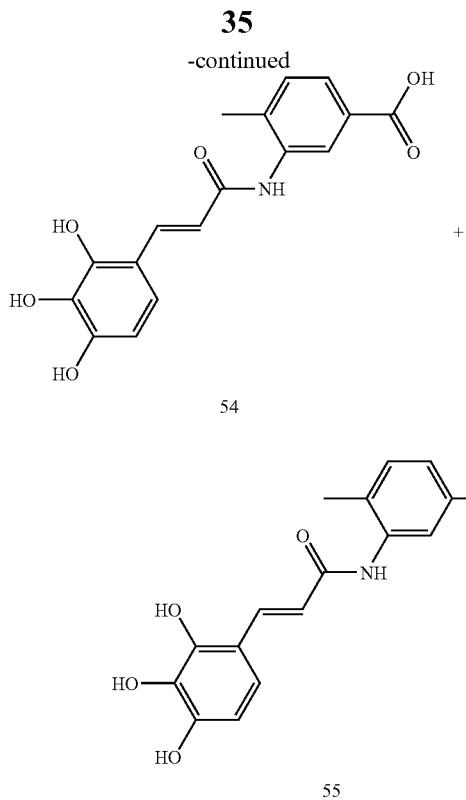

Step 1:

(The following reaction is done in an anhydrous $N_2$ atmosphere.) Dissolve trans-2,3,4-Trimethoxycinnamic acid (50) (200 mg, 0.84 mmol) in anhydrous DCM (4.4 mL) at it and add anhydrous DMF (3 drops, cat. amount). Then add slowly oxalyl chloride (96 μL, 1.09 mmol) stir the turbid mixture for additional 2 h at rt. Remove solvent and dry the residue in oil pump vacuum to obtain trans-2,3,4-Trimethoxycinnamic acid chloride (51) (ca. 0.84 mmol) as an yellow solid. Dissolve acid chloride (51) (108 mg, 0.42 mmol) in anhydrous DCM (4.0 mL) and add it to an ice cooled solution of Methyl 3-amino-4-methylbenzoate (52) (69 mg, 0.42 mmol) in anhydrous DCM (2.0 mL) and anhydrous pyridine (1.2 mL). Stir the resulting reaction mixture at rt overnight. Pour the reaction mixture into ice cooled 1M aqu. HCl, extract with EtOAc (3×), wash the combined organic layer with brine and dry it with $Na_2SO_4$. Purify the crude product by filtration through a short pad of silica gel with EtOAc and remove solvent to obtain 4-Methyl-3-[3-(2,3,4-trimethoxy-phenyl)-acryloylamino]-benzoic acid methyl ester (53) (99 mg, 61%) as a light yellow solid. $^1$H NMR (400 MHz, $CDCl_3$): 2.35 (s, 3H); 3.87 (s, 3H); 3.88 (s, 6H); 3.91 (br.s, 3H); 6.59 (d, 1H, J=15.6 Hz); 6.68 (d, 1H, J=8.6 Hz); 7.08 (br.s, 1H); 7.20-7.29 (m, 2H); 7.77 (br.d, 1H, J=8.6 Hz); 7.90 (d, 1H, J=15.6 Hz); 8.55 (br.s 1H).

Step 2:

(The following reaction is done in an anhydrous $N_2$ atmosphere.) Dissolve anilide (53) (40 mg, 0.10 mmol) in anhydrous DCM (1.3 mL) at −78° C., add dropwise a 1M solution of $BBr_3$ in DCM (830 μL, 0.83 mmol) and stir for additional 30 min at −78° C. After slowly warming up stir the reaction solution for additional 4 h at rt. Cool reaction mixture to 0° C., add dropwise water and DCM under vigorous stirring followed by MeOH to homogenize the mixture. Partition the hydrolized reaction mixture between water and EtOAc, extract the aqu. layer with EtOAc (3×), wash combined organic layer with brine and dry it with $Na_2SO_4$. Purify the crude product by preparative RP HPLC (gradient, water/$CH_3CN$ 95:5 to 5:95) to obtain 4-Methyl-3-[3-(2,3,4-trihydroxy-phenyl)-acryloylamino]-benzoic acid (54) (6.5 mg, 19%) as an yellowish solid and 4-Methyl-3-[3-(2,3,4-trihydroxy-phenyl)-acryloylamino]-benzoic acid methyl ester (55) (9 mg, 25%) as an yellowish solid. $^1$H NMR (400 MHz, $CD_3OD$) (54): 2.40 (s, 3H); 6.43 (d, 1H, J=8.6 Hz); 6.90 (d, 1H, J=15.6 Hz); 6.97 (d, 1H, J=8.6 Hz); 7.40 (d, 1H, J=8.1 Hz); 7.83 (dd, 1H, $J_1$=8.1 Hz, $J_2$=1.5 Hz); 7.93 (d, 1H, J=15.6 Hz); 8.17 (br.s, 1H); (55): 2.40 (s, 3H); 3.93 (s, 3H); 6.43 (d, 1H, J=8.6 Hz); 6.90 (d, 1H, J=15.7 Hz); 6.97 (d, 1H, J=8.6 Hz); 7.40 (d, 1H, J=8.1 Hz); 7.82 (dd, 1H, $J_1$=7.8 Hz, $J_2$=1.7 Hz); 7.93 (d, 1H, J=15.9 Hz); 8.18 (br.s, 1H).

EXAMPLE 5

5-{2-Amino-4-[2-(3,4,5-trihydroxy-phenyl)-acetylamino]-phenyl}-2-methyl-furan-3-carboxylic acid (62)

SCHEME 12

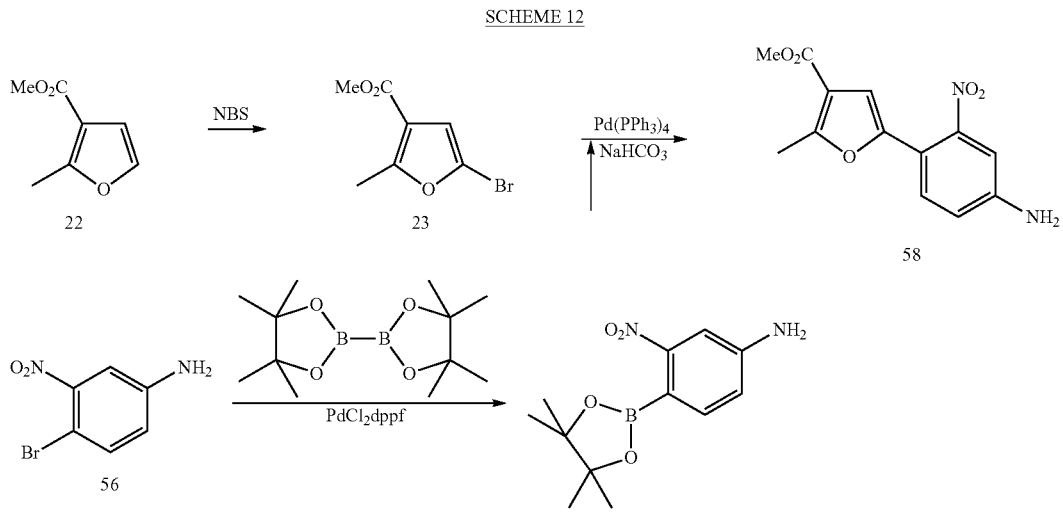

-continued

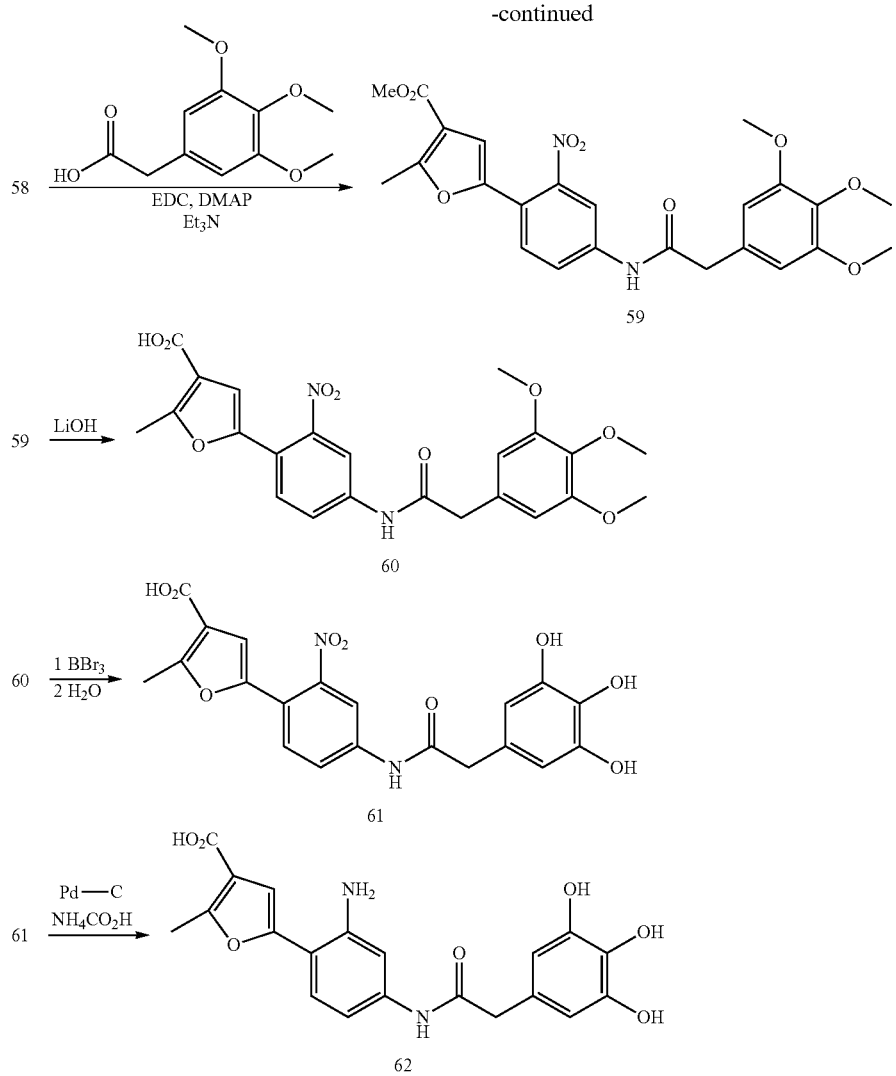

Step 1:

(The following reaction is done under exclusion of light.) Dissolve 2-Methyl-furan-3-carboxylic acid methyl ester (22) (2.00 mL, 15.9 mmol) in chloroform (11 mL) and glacial acetic acid (11 mL) and add NBS (3.85 g, 21.6 mmol) portionwise in between a period of 75 min. Stir the reaction suspension for additional 16 h at rt. Add water to the reaction mixture and extract the aqu. layer with DCM (2 times), wash the combined organic layer with 2M aqu. NaOH, water and brine and dry it with $Na_2SO_4$ to obtain 5-Bromo-2-methyl-furan-3-carboxylic acid methyl ester (23) (2.80 g, 80%) as a red brown oil. No further purification. $^1$H NMR (400 MHz, $CDCl_3$): 2.54 (s, 3H); 3.80 (s, 3H); 6.53 (s, 1H).

Step 2:

(The following reaction is done in a $N_2$ atmosphere.) Dissolve $PdCl_2(dppf) \cdot CH_2Cl_2$ (245 mg, 0.30 mmol), KOAc (2.52 g, 25.7 mmol) and Bis-(pinacolato)diboron (3.81 g, 15.00 mmol) in anhydrous DMSO (50 mL) and add 4-Bromo-3-nitro-phenylamine (56) (2.17 g, 10.00 mmol). Degas the mixture carefully and flush with $N_2$ again (5 times) and stir it for 24 h at 80° C. Cool the reaction mixture to it and partition it between water and toluene. Extract the aqu. layer with EtOAc (3 times), wash the combined organic layer with water and brine and dry it with $Na_2SO_4$. The obtained crude residue is filtrated through a short pad of silica gel using EtOAc/CyH (1+1) to obtain 3-Nitro-4-(4,4,5,5-tetramethyl-[1,3,2]dioxaborolan-2-yl)-phenylamine (57) (2.04 g, 77%) as a dark red solid. No further purification. $^1$H NMR (400 MHz, $CDCl_3$): 1.37 (s, 12H); 3.95 (br.s, 2H); 6.87 (dd, 1H, $J_1$=7.8 Hz, $J_2$=2.3 Hz); 7.30 (d, 1H, J=8.1 Hz); 7.35 (d, 1H, J=2.3 Hz).

Step 3:

(The following reaction is done in a $N_2$ atmosphere.) Dissolve $Pd(PPh_3)_4$ (59 mg, 0.05 mmol) and 5-Bromo-2-methyl-furan-3-carboxylic acid methyl ester (23) (447 mg, 2.04 mmol) in DME (3 mL) and stir for 10 min at rt. Add 3-Nitro-4-(4,4,5,5-tetramethyl-[1,3,2]dioxaborolan-2-yl)-phenylamine (57) (465 mg, 1.76 mmol) followed by an aqu. 1M sodium bicarbonate solution (5.10 mL, 5.10 mmol). Degas the reaction mixture carefully, flush with $N_2$ (5 times) and stir for 4.5 h at 90° C. (reflux). Cool reaction mixture to rt, remove organic solvent under reduced pressure and partition the residue between water and EtOAc. Extract the aqu. layer with EtOAc (3 times), wash the combined organic layer with water and brine and dry it with $Na_2SO_4$. Purify the obtained crude product by flash chromatography (silica gel, EtOAc/CyH 1+3, later 1+2) to obtain 5-(4-Amino-2-nitro-phenyl)-2-methyl-furan-3-carboxylic acid methyl ester (58) (167 mg, 34%) as a red solid. $^1$H NMR (400 MHz, CDCl$_3$): 2.57 (s, 3H); 3.81 (s, 3H); 4.05 (br.s, 2H); 6.68 (s, 1 H); 6.81 (dd, 1H, J$_1$=8.3 Hz, J$_2$=2.3 Hz); 6.99 (d, 1H, J=2.3 Hz); 7.39 (d, 1H, J=8.3 Hz).

Step 4:

(The following reaction is done in an anhydrous N$_2$ atmosphere.) Suspend EDCHCl (138 mg, 0.72 mmol) and Et$_3$N (101 µL, 0.72) in anhydrous DCM (4.5 mL) and stir the resulting solution for 5 min at rt. Add 2-(3,4,5-Trimethoxyphenyl)-acetic acid (163 mg, 0.72 mmol) and DMAP (8 mg, 0.07 mmol) and stir the resulting solution for 10 min. Add 5-(4-Amino-2-nitro-phenyl)-2-methyl-furan-3-carboxylic acid methyl ester (58) (100 mg, 0.36 mmol) and stir the reaction solution for 22 h at rt. Quench reaction solution with sat. aqu. NH$_4$Cl and water, separate layers and extract aqu. layer with DCM (3 times). Wash the combined organic layer with water and brine and dry with Na$_2$SO$_4$. Purify the crude product by preparative radial chromatography (silica gel, EtOAc/CyH 1+1) to obtain 2-Methyl-5-{2-nitro-4-[2-(3,4,5-trimethoxy-phenyl)-acetylamino]-phenyl}-furan-3-carboxylic acid methyl ester (59) (96 mg, 55%) as an yellow solid. $^1$H NMR (400 MHz, CDCl$_3$): 2.55 (s, 3H); 3.65 (s, 2H); 3.79 (s, 3H); 3.81 (s, 6H); 3.82 (s, 3H); 6.50 (s, 2H); 6.77 (s, 1H); 7.53 (d, 1H, J=8.6 Hz); 7.66 (dd, 1H, J$_1$=8.6 Hz, J$_2$=2.0 Hz); 7.93 (br.s, 1 H); 7.96 (d, 1H, J=2.0 Hz).

Step 5:

Dissolve 2-Methyl-5-{2-nitro-4-[2-(3,4,5-trimethoxy-phenyl)-acetylamino]-phenyl}-furan-3-carboxylic acid methyl ester (59) (50 mg, 0.10 mmol) in THF (1.0 mL) and MeOH (0.5 mL) at rt and add 1M aqu LiOH (525 µL, 0.52 mmol). Stir the reaction mixture for 17 h at rt. Add dropwise 1M aqu. HCl (5804, 0.58 mmol) and extract the mixture with EtOAc (3 times), wash the combined organic layer with brine and dry it with Na$_2$SO$_4$. Purify the obtained crude product by preparative TLC (silica gel, EtOAc/MeOH 9+1) to obtain 2-Methyl-5-{2-nitro-4-[2-(3,4,5-trimethoxy-phenyl)-acetylamino]-phenyl}-furan-3-carboxylic acid (60) (35 mg, 71%) as a brown sticky solid. $^1$H NMR (400 MHz, CDCl$_3$): 2.61 (s, 3H); 3.70 (s, 2H); 3.86 (s, 3H); 3.87 (s, 6H); 6.51 (s, 2H); 6.85 (s, 1H); 7.29 (br.s, 1H); 7.58 (d, 1H, J=8.6 Hz); 7.62 (dd, 1H, J$_1$=9.0 Hz, J$_2$=2.2 Hz); 7.98 (d, 1H, J=2.0 Hz).

Step 6:

(The following reaction is done in an anhydrous N$_2$ atmosphere.) Dissolve 2-Methyl-5-{2-nitro-4-[2-(3,4,5-trimethoxy-phenyl)-acetylamino]-phenyl}-furan-3-carboxylic acid (60) (33 mg, 0.07 mmol) in anhydrous DCM (1.0 mL), cool the solution to −78° C. and add dropwise BBr$_3$ (66 µL, 0.70 mmol). Stir the reaction mixture for 10 min at −78° C. and after slowly warming up for additional 2 h at rt. Cool reaction mixture to 0° C., add dropwise water and DCM followed by MeOH to homogenize the mixture and remove solvent. Suspend the crude product in MeOH and filtrate it through a short pad of celite to obtain 2-Methyl-5-{2-nitro-4-[2-(3,4,5-trihydroxy-phenyl)-acetylamino]-phenyl}-furan-3-carboxylic acid (61) (22 mg, 72%) as a brown solid. $^1$H NMR (400 MHz, CD$_3$OD): 2.62 (s, 3H); 3.53 (s, 2H); 6.40 (s, 2H); 6.88 (s, 1H); 7.73 (d, 1H, J=8.6 Hz); 7.80 (dd, 1H, J$_1$=8.6 Hz, J$_2$=2.0 Hz); 8.24 (d, 1H, J=2.0 Hz).

Step 7:

(The following reaction is done in an N$_2$ atmosphere.) Dissolve 2-Methyl-5-{2-nitro-4-[2-(3,4,5-trihydroxy-phenyl)-acetylamino]-phenyl}-furan-3-carboxylic acid (61) (21 mg, 0.05 mmol) in MeOH (1.5 mL) and add Pd on carbon (10% (w/w) Pd content, 11.5 mg, 0.005 mmol) followed by NH$_4$CO$_2$H (68 mg, 1.08 mmol) at rt. Degas the reaction mixture carefully (flush with N$_2$) and stir it for 17 h at rt. Filtrate reaction mixture through a short pad of celite and remove solvent. Purify the crude product by preparative RP HPLC (gradient, water/CH$_3$CN 95:5 to 5:95) to obtain 5-{2-Amino-4-[2-(3,4,5-trihydroxy-phenyl)-acetylamino]phenyl}-2-methyl-furan-3-carboxylic acid (62) (4.6 mg, 23%) as a white solid. $^1$H NMR (400 MHz, CD$_3$OD): 2.69 (s, 3H); 3.50 (s, 2H); 6.39 (s, 2H); 6.91 (s, 1H); 7.13 (br.d, 1H, J=8.6 Hz); 7.57 (d, 1H, J=8.6 Hz) 7.65 (br.s, 1H).

EXAMPLE 6

{4-[2-(3,4,5-Trihydroxy-phenyl)-acetyl]piperazin-1-yl}-acetic acid ethyl ester (65)

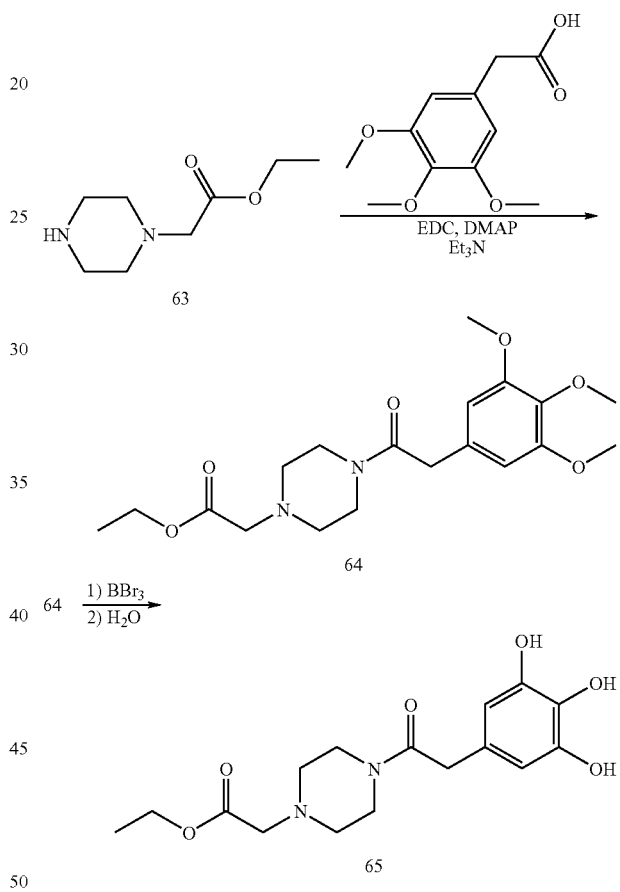

SCHEME 13

Step 1:

(The following reaction is done in an anhydrous N$_2$ atmosphere.) Suspend EDCHCl (188 mg, 0.98 mmol) and Et$_3$N (137 mL, 0.98 mmol) in anhydrous DCM (1.0 mL) and stir the resulting solution for 5 min at rt. Add 2-(3,4,5-Trimethoxyphenyl)-acetic acid (163 mg, 0.72 mmol) and DMAP (8 mg, 0.07 mmol) and stir the resulting solution for 10 min. Add 1-(Ethoxycarbonylmethyl)piperazine (63) (112 mg, 0.65 mmol) and stir the reaction solution overnight at rt. Quench reaction solution with sat. aqu. NH$_4$Cl and water, separate layers and extract aqu. layer with DCM (3 times). Wash the combined organic layer with water and brine and dry with Na$_2$SO$_4$. Purify the crude product by preparative radial chromatography (silica gel, EtOAc/MeOH 10+1) to obtain {4-[2-(3,4,5-Trimethoxy-phenyl)-acetyl]-piperazin-1-yl}-acetic acid ethyl ester (64) (99 mg, 40%) as a colorless oil. $^1$H NMR (400 MHz, CDCl$_3$): 1.25 (t, 3H, J=7.1 Hz); 2.48 (br.m, 2H); 2.58 (br.m, 2H); 3.21 (br.s, 2H); 3.53 (br.m, 2H); 3.65 (s, 2H); 3.71 (br.m, 2H); 3.81 (s, 3H); 3.82 (s, 6H); 4.16 (q, 2H, J=7.1 Hz); 6.42 (s, 2H).

Step 2:

(The following reaction is done in an anhydrous N$_2$ atmosphere.) Dissolve {4-[2-(3,4,5-Trimethoxy-phenyl)-acetyl]-piperazin-1-yl}-acetic acid ethyl ester (64) (99 mg, 0.26 mmol) in anhydrous DCM (6.0 mL), cool the solution to −78° C. and add dropwise a 1 M BBr$_3$ solution in DCM (2.30 mL, 2.30=101). Stir the reaction mixture for 30 min at −78° C. and after slowly warming up for additional 4 h at −20° C. Add dropwise water and extract the mixture with EtOAc (3 times). Wash the combined organic layer with brine and dry it dry with Na$_2$SO$_4$. Purify the crude product by preparative RP HPLC (gradient, water/CH$_3$CN 95:5 to 5:95) to obtain {4-[2-(3,4,5-Trihydroxy-phenyl)-acetyl]-piperazin-1-yl}-acetic acid ethyl ester (65) (34 mg, 40%) as a sticky brownish solid. $^1$H NMR (400 MHz, CD$_3$OD): 1.35 (t, 3H, J=7.1 Hz); 3.14-3.24 (br.m, 2H); ca. 3.32 (br.m, 2H); 3.65 (s, 2H); 3.78-4.00 (br.m, 4H); 4.12 (s, 2H); 4.34 (q, 2H, J=7.1 Hz); 6.29 (s, 2H).

EXAMPLE 7

{4-[3-(3,4,5-Trihydroxy-phenyl)-propionyl]-piperazin-1-yl}-acetic acid (68)

SCHEME 14

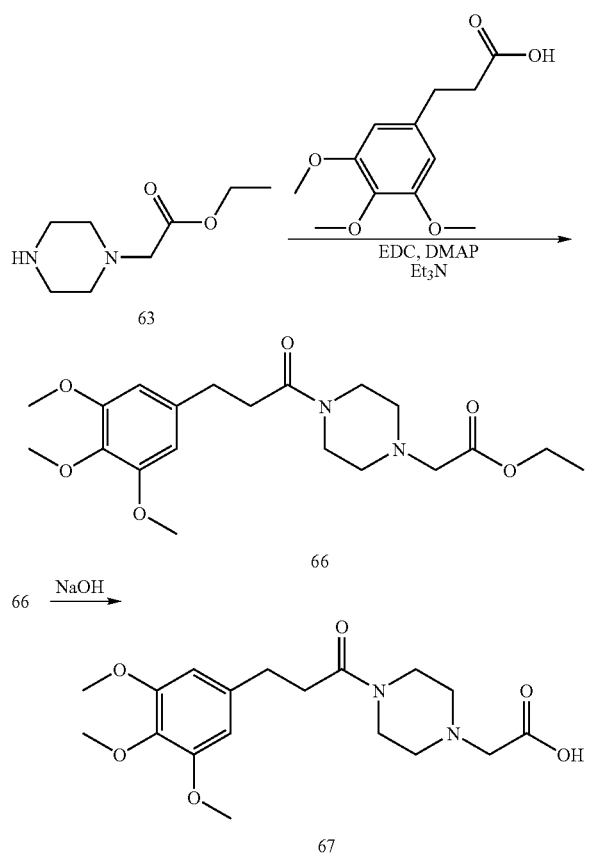

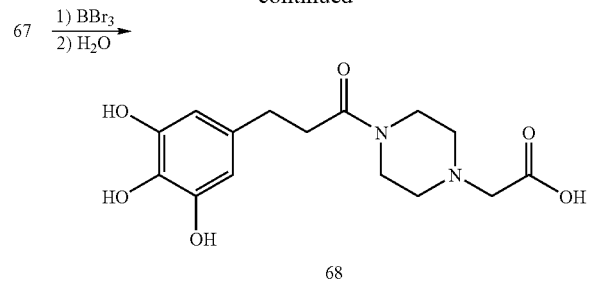

Step 1:

(The following reaction is done in an anhydrous N$_2$ atmosphere.) Suspend EDCHCl (376 mg, 1.96 mmol) and Et$_3$N (275 μL, 1.96 mmol) in anhydrous DCM (2.0 mL) and stir the resulting solution for 5 min at rt. Add 3-(3,4,5-Trimethoxy-phenyl)-propionic acid (346 mg, 1.44 mmol) and DMAP (17 mg, 0.14 mmol) and stir the resulting solution for 15 min. Add 1-(Ethoxycarbonylmethyl)piperazine (63) (224 mg, 1.30 mmol) and stir the reaction solution overnight at rt. Quench reaction solution with water, separate layers and extract aqu. layer with EtOAc (3 times). Filtrate the combined organic layer through a short pad of silica gel and remove solvent. Purify the crude product by preparative radial chromatography (silica gel, EtOAc/MeOH 9+1) to obtain {4-[3-(3,4,5-Trimethoxy-phenyl)-propionyl]-piperazin-1-yl}-acetic acid ethyl ester (66) (426 mg, 83%) as a colorless oil. $^1$H NMR (400 MHz, CDCl$_3$): 1.26 (t, 3H, J=7.1 Hz); 2.45-2.70 (br.m, 6H); 2.89 (t, 2 H, J=7.7 Hz); 3.26 (br.s, 2H); 3.43-3.56 (br.m, 2H); 3.61-3.76 (br.m, 2H); 3.80 (s, 3H); 3.83 (s, 6H); 4.18 (q, 2H, J=7.1 Hz); 6.41 (s, 2H).

Step 2:

Dissolve {4-[3-(3,4,5-Trimethoxy-phenyl)-propionyl]-piperazin-1-yl}-acetic acid ethyl ester (66) (100 mg, 0.25 mmol) in MeOH (2.0 mL) at it and add 2M aqu NaOH (260 μL, 0.52 mmol). Stir the reaction mixture for 1 h under reflux. Add dropwise 1M aqu. HCl (550 μL, 0.55 mmol), extract the mixture with EtOAc (3 times) and remove solvent obtain {4-[3-(3,4,5-Trimethoxy-phenyl)-propionyl]piperazin-1-yl}-acetic acid (67) (88 mg, 95%) as a brown sticky solid. No further purification. $^1$H NMR (400 MHz, CDCl$_3$/CD$_3$OD 9+1): 2.54 (br.t, 2H); 2.78 (t, 2H, J=7.5 Hz); 2.83-3.10 (br.m, 2H); 3.24 (s, 2H); 3.43-3.62 (br.m, 2H); 3.68 (s, 3H); 3.73 (s, 6H); 3.74-3.85 (br.m, 4H); 6.34 (s, 2 H).

Step 3:

(The following reaction is done in an anhydrous N$_2$ atmosphere.) Dissolve {4-[3-(3,4,5-Trimethoxy-phenyl)-propionyl]-piperazin-1-yl}-acetic acid (67) (88 mg, 0.24 mmol) in anhydrous DCM (10 mL), cool the solution to −78° C. and add dropwise BBr$_3$ (3304, 3.50 mmol). Stir the reaction mixture for 30 min at −78° C. and after slowly warming up for additional 4 h at −20° C. Add dropwise water and remove solvent. Purify the crude product by preparative RP HPLC (gradient, water/CH$_3$CN 95:5 to 5:95) to obtain {4-[3-(3,4,5-Trimethoxy-phenyl)-propionyl]-piperazin-1-yl}-acetic acid (68) (2 mg, 2%) as a white solid. $^1$H NMR (400 MHz, CD$_3$OD): 2.67 (t, 2H, J=6.9 Hz); 2.79 (t, 2H, J=6.9 Hz); 2.86-2.96 (br.m, 2H); 3.23-3.31 (br.m, 2H); 3.67-3.77 (br.m, 2H); 3.80-3.93 (br.m, 2H); 3.95 (s, 2H); 6.25 (s, 2H).

EXAMPLE 8

{2'-[3-(3,4,5-Trihydroxy-phenyl)-propionylamino]-biphenyl-3-yl}-acetic acid methyl ester (73)

SCHEME 15

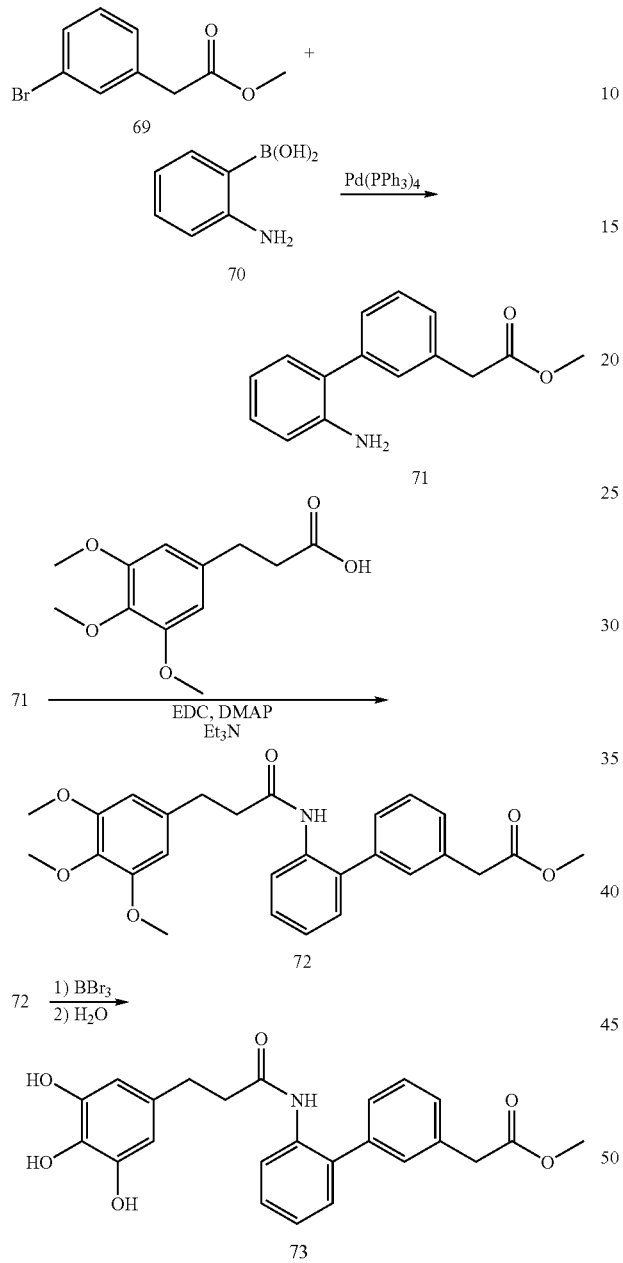

Step 1:

(The following reaction is done in an oxygenfree $N_2$ atmosphere.) Add ethanol (0.8 mL), Tetrakis-(triphenylphosphine)-palladium(0) (30 mg, 2.2 mol %) and $Na_2CO_3$ decahydrate (944 mg, 3.30 mmol; presolved in 1.2 mL $H_2O$) subsequently to dissolved 2-Amino-benzeneboronic acid (70) (201 mg, 1.30 mmol) in toluene (6.0 mL). Degas the reaction mixture for 5 times and flood with $N_2$ again. Add (3-Bromo-phenyl)-acetic acid methyl ester (69) (270 mg, 1.18 mmol) in toluene (6.0 mL), degas again (5 times) and stir the reaction solution overnight at 100° C. Partition the reaction solution between EtOAc and brine (1+1) and extract the separated aqueous layer 3 times with EtOAc. Wash combined organic layer with brine and dry with $Na_2SO_4$. Remove solvent under reduced pressure and purify the crude product by preparative radial chromatography (silica gel 60 PF, CyH/EtOAc 3+1) to obtain (2'-Amino-biphenyl-3-yl)-acetic acid methyl ester (71) as an orange oil (304 mg, 81%). $^1$H NMR (400 MHz, $CDCl_3$): 3.66 (s, 2H); 3.69 (s, 3H); 3.62-3.86 (br.s, 2H); 6.75 (d, 1H, J=8.1 Hz); 6.80 (t, 1H, J=7.3 Hz); 7.11 (d, 1 H, J=7.3 Hz); 7.15 (d, 1H, J=8.1 Hz); 7.22-7.26 (br.m, 1H); 7.32-7.42 (m, 3H).

Step 2:

(The following reaction is done in an anhydrous $N_2$ atmosphere.) Suspend EDCHCl (61 mg, 0.32 mmol) and $Et_3N$ (44 µL, 0.32 mmol) in anhydrous DCM (1.0 mL) and stir the resulting solution for 5 min at rt. Add 3-(3,4,5-Trimethoxy-phenyl)-propionic acid (55 mg, 0.23 mmol) and DMAP (2 mg, 0.02 mmol) and stir the resulting solution for 15 min. Add (2'-Amino-biphenyl-3-yl)-acetic acid methyl ester (71) (50 mg, 0.21 mmol) and stir the reaction solution overnight at rt. Quench reaction solution with water, separate layers and extract aqu. layer with DCM (3 times). Wash combined organic layer with brine and dry with $Na_2SO_4$. Purify the crude product by preparative radial chromatography (silica gel, EtOAc/CyH 1+1) to obtain {2'-[3-(3,4,5-Trimethoxy-phenyl)-propionylamino]-biphenyl-3-yl}-acetic acid methyl ester (72) (46 mg, 48%) as a yellow oil. $^1$H NMR (400 MHz, $CDCl_3$): 2.50 (t, 2H, J=7.6 Hz); 2.90 (t, 2H, J=7.7 Hz); 3.64 (s, 2H); 3.65 (s, 3H); 3.77 (s, 6H); 3.78 (s, 3H); 6.38 (s, 2H); 7.09-7.18 (m, 3H); 7.19-7.28 (m, 3H); 7.34 (d, 1H, J=8.1 Hz); 7.38 (d, 1H, J=7.8 Hz); 8.31 (br.d, 1H, J=7.8 Hz).

Step 3:

(The following reaction is done in an anhydrous $N_2$ atmosphere.) Dissolve {2'-[3-(3,4,5-Trimethoxy-phenyl)-propionylamino]-biphenyl-3-yl}-acetic acid methyl ester (72) (46 mg, 0.10 mmol) in anhydrous DCM (1.0 mL), cool the solution to −78° C. and add dropwise $BBr_3$ (85 µL, 0.90 mmol). Stir the reaction mixture for 30 min at −78° C. and after slowly warming up for additional 2 h at rt. Add dropwise ice water, separate layers and extract aqu. layer with DCM (3 times). Wash combined organic layer with brine and dry with $Na_2SO_4$. Purify the crude product by preparative RP HPLC (gradient, water/$CH_3CN$ 95:5 to 5:95) to obtain {2'-[3-(3,4,5-Trihydroxy-phenyl)-propionylamino]-biphenyl-3-yl}-acetic acid methyl ester (73) (2 mg, 5%). $^1$H NMR (400 MHz, $CD_3CN$): 2.43 (t, 2H, J=7.6 Hz); 2.69 (t, 2H, J=7.6 Hz); 3.66 (s, 3H); 3.70 (s, 2H); 6.25 (s, 2H); 7.18-7.34 (m, 5 H); 7.35-7.44 (m, 2H); 7.65 (br.s, 1H); 7.89 (br.d, 1H, J=8.3 Hz).

EXAMPLE 9

4-[3-(3,4,5-Trihydroxy-phenyl)-propionylamino]-cyclohexanecarboxylic acid (76)

SCHEME 16

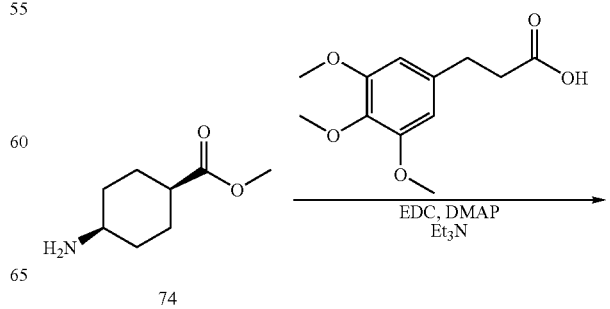

1.91-2.02 (m, 2H); 2.42 (t, 2H, J=7.6 Hz); 2.47-2.54 (m, 1H); 2.71 (t, 2H, J=7.3 Hz); 3.75-3.84 (m, 1H); 6.23 (s, 2H).

EXAMPLE 10

4-[3-(3,4,5-Trihydroxy-phenyl)-propionylamino]-benzoic acid (79)

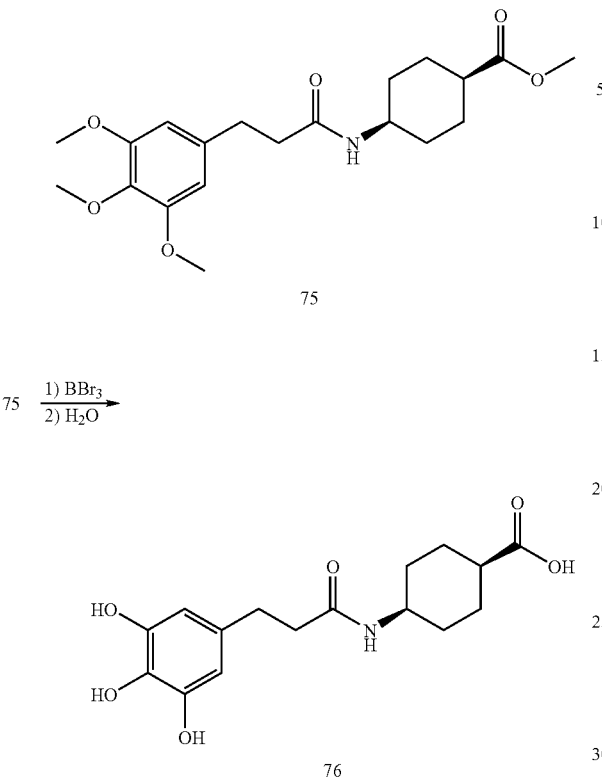

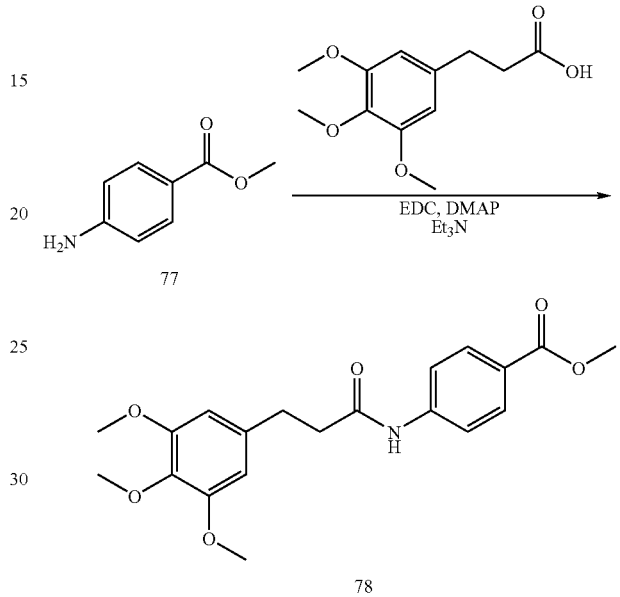

Step 1:

(The following reaction is done in an anhydrous $N_2$ atmosphere.) Suspend EDCHCl (175 mg, 0.91 mmol) and $Et_3N$ (127 μL, 0.91 mmol) in anhydrous DCM (8.0 mL) and stir the resulting solution for 5 min at rt. Add 3-(3,4,5-Trimethoxy-phenyl)-propionic acid (219 mg, 0.91 mmol) and DMAP (22 mg, 0.18 mmol) and stir the resulting solution for 10 min. Add cis-4-Amino-cyclohexanecarboxylic acid methyl ester (74) (136 mg, 0.87 mmol) and stir the reaction solution 2d at rt Remove solvent and purify the crude product by flash chromatography (silica gel, EtOAc/CyH 3+1, later EtOAc) to obtain cis-{4-[3-(3,4,5-Trimethoxy-phenyl)-propionylamino]-cyclohexanecarboxylic acid methyl ester (75) (254 mg, 76%) as a colorless viscous oil. $^1$H NMR (400 MHz, $CDCl_3$): 1.40-1.51 (m, 2 H); 1.59-1.70 (m, 4H); 1.70-1.82 (m, 2H); 2.40-2.48 (m, 3H); 2.88 (t, 2H, J=7.6 Hz); 3.65 (s, 3H); 3.79 (s, 3H); 3.82 (s, 6H); 3.86-3.95 (m, 1H); 5.33 (br.d, 1H, J=7.3 Hz); 6.40 (s, 2H).

Step 2:

(The following reaction is done in an anhydrous $N_2$ atmosphere.) Dissolve cis-{4-[3-(3,4,5-Trimethoxy-phenyl)-propionylamino]-cyclohexanecarboxylic acid methyl ester (75) (82 mg, 0.21 mmol) in anhydrous DCM (2.0 mL), cool the solution to −78° C. and add dropwise $BBr_3$ (205 μL, 2.17 mmol). Stir the reaction mixture for 20 min at −78° C. and after slowly warming up for additional 2 h at rt Add dropwise water, followed by DCM and MeOH and remove solvent. Purify the crude product by preparative RP HPLC (gradient, water/$CH_3CN$ 95:5 to 5:95) to obtain cis-4-[3-(3,4,5-Trihydroxy-phenyl)-propionylamino]-cyclohexanecarboxylic acid (76) (7 mg, 10%) as a colorless sticky solid. $^1$H NMR (400 MHz, $CD_3OD$): 1.47-1.60 (m, 2H); 1.62-1.73 (m, 4H);

Step 1:

(The following reaction is done in an anhydrous $N_2$ atmosphere.) Suspend EDCHCl (80 mg, 0.41 mmol) and $Et_3N$ (58 μL, 0.41 mmol) in anhydrous DCM (2.0 mL) and stir the resulting solution for 5 min at rt. Add 3-(3,4,5-Trimethoxy-phenyl)-propionic acid (70 mg, 0.29 mmol) and DMAP (5 mg, 0.04 mmol) and stir the resulting solution for 10 min. Add 4-Amino-benzoic acid methyl ester (77) (42 mg, 0.27 mmol) and stir the reaction solution 2d at rt. Quench reaction solution with water, separate layers and extract aqu. layer with DCM (3 times). Wash combined organic layer with brine, dry with $Na_2SO_4$ and filtrate it through a short pad of silica gel using EtOAc to obtain 4-[3-(3,4,5-Trimethoxy-phenyl)-propionylamino]-benzoic acid methyl ester (78) (91 mg, 88%) as a white solid. No further purification. $^1$H NMR (400 MHz, $CDCl_3$): 2.60 (t, 2H, J=7.6 Hz); 2.91 (t, 2H, J=7.6 Hz); 3.70 (s, 6H); 3.76 (s, 3H); 3.83 (s, 3H); 6.35 (s, 2H); 7.55 (d, 2H, J=8.3 Hz); 7.91 (d, 2H, J=8.6 Hz); 8.09 (s, 1H).

Step 2:

(The following reaction is done in an anhydrous $N_2$ atmosphere.) Dissolve 4-[3-(3,4,5-Trimethoxy-phenyl)-propionylamino]-benzoic acid methyl ester (78) (45 mg, 0.12 mmol) in anhydrous DCM (1.2 mL), cool the solution to −78° C. and add dropwise $BBr_3$ (90 μL, 0.96 mmol). Stir the reaction mixture for 30 min at −78° C. and after slowly warming up for additional 3 h at rt. Add dropwise ice-water/THF (1+1) followed by MeOH and remove solvent. Purify the crude product by preparative RP HPLC (gradient, water/$CH_3CN$ 95:5 to 5:95) to obtain 4-[3-(3,4,5-Trihydroxy-phenyl)-propionylamino]-benzoic acid (79) (17 mg, 44%) as a white solid. $^1$H NMR (400 MHz, $CD_3OD$): 2.65 (t, 2H, J=7.5 Hz); 2.83 (t, 2H, J=7.5 Hz); 6.29 (s, 2H); 7.68 (d, 2H, J=8.3 Hz); 7.99 (d, 2H, J=8.6 Hz).

EXAMPLE 11

(5-{2-[(3',4',5'-Trihydroxy-biphenyl-2-carbonyl)-amino]-phenyl}-thiophen-2-yl)-acetic acid (87)

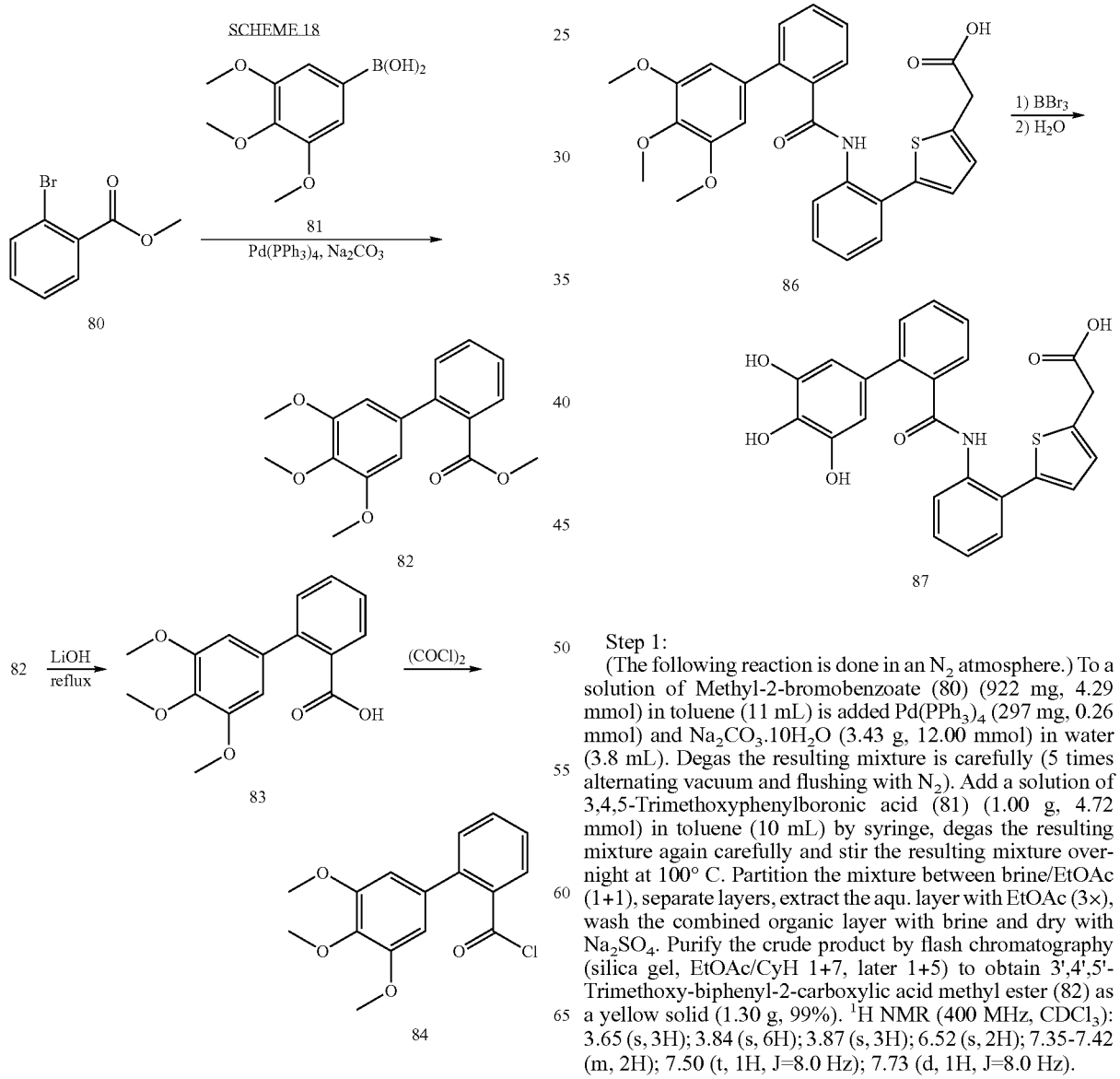

Step 1:

(The following reaction is done in an $N_2$ atmosphere.) To a solution of Methyl-2-bromobenzoate (80) (922 mg, 4.29 mmol) in toluene (11 mL) is added $Pd(PPh_3)_4$ (297 mg, 0.26 mmol) and $Na_2CO_3 \cdot 10H_2O$ (3.43 g, 12.00 mmol) in water (3.8 mL). Degas the resulting mixture is carefully (5 times alternating vacuum and flushing with $N_2$). Add a solution of 3,4,5-Trimethoxyphenylboronic acid (81) (1.00 g, 4.72 mmol) in toluene (10 mL) by syringe, degas the resulting mixture again carefully and stir the resulting mixture overnight at 100° C. Partition the mixture between brine/EtOAc (1+1), separate layers, extract the aqu. layer with EtOAc (3×), wash the combined organic layer with brine and dry with $Na_2SO_4$. Purify the crude product by flash chromatography (silica gel, EtOAc/CyH 1+7, later 1+5) to obtain 3',4',5'-Trimethoxy-biphenyl-2-carboxylic acid methyl ester (82) as a yellow solid (1.30 g, 99%). $^1$H NMR (400 MHz, $CDCl_3$): 3.65 (s, 3H); 3.84 (s, 6H); 3.87 (s, 3H); 6.52 (s, 2H); 7.35-7.42 (m, 2H); 7.50 (t, 1H, J=8.0 Hz); 7.73 (d, 1H, J=8.0 Hz).

Step 2:

Dissolve 3',4',5'-Trimethoxy-biphenyl-2-carboxylic acid methyl ester (82) (626 mg, 2.08 mmol) in MeOH (14 mL) at rt and add 1M aqu LiOH (4.2 mL, 4.20 mmol). Stir reaction mixture for 8 h under reflux. Remove solvent and partition the residue between 1M aqu. HCl and EtOAc, separate layers, extract the aqu. layer with EtOAc (3×), wash the combined organic layer with brine and dry with $Na_2SO_4$. Remove solvent and recrystallize residue from EtOAc/CyH 1+2 to obtain 3',4',5'-Trimethoxy-biphenyl-2-carboxylic acid (83) as a white solid (423 mg, 79%). $^1$H NMR (400 MHz, $CD_3OD$: 3.84 (s, 3H); 3.89 (s, 6H); 6.68 (s, 2H); 7.42-7.49 (m, 2H); 7.57 (t, 1H, J=7.5 Hz); 7.76 (d, 1H, J=8.0 Hz).

Step 3:

(The following reaction is done in an anhydrous $N_2$ atmosphere.) Dissolve 3',4',5'-Trimethoxy-biphenyl-2-carboxylic acid (83) (54 mg, 0.18 mmol) in anhydrous DCM (1.3 mL) and add anhydrous DMF (1 drop, cat. amount). Then add slowly oxalyl chloride (21 μL, 0.24 mmol) by keeping temperature at ca. 20° C. with a water bath and stir the turbid mixture for additional 2 h at rt. Remove solvent and dry in vacuum to obtain crude 3',4',5'-Trimethoxy-biphenyl-2-carbonyl chloride (84) as a yellow solid. No further purification.

Step 4:

Add a solution of 3',4',5'-Trimethoxy-biphenyl-2-carbonyl chloride (84) (0.18 mmol) in DCM (1.0 mL) to an ice cooled solution of [5-(2-Amino-phenyl)-thiophen-2-yl]-acetic acid methyl ester (46) (46 mg, 0.18 mmol) in anhydrous DCM (2.0 mL) and anhydrous pyridine (0.5 mL). Stir the reaction mixture for 1 h at 0° C. and additional 20 h at rt. Pour the reaction mixture into ice cooled 1M aqu. HCl, extract with EtOAc (2×) and DCM (2×), wash the combined organic layer with brine and dry with $Na_2SO_4$. Purify the crude product by preparative radial chromatography (silica gel, EtOAc/CyH 1+2) to obtain (5-{2-[(3',4',5'-Trimethoxy-biphenyl-2-carbonyl)-amino]-phenyl}-thiophen-2-yl)-acetic acid methyl ester (85) as a light brown solid (58 mg, 59%). $^1$H NMR (400 MHz, $CDCl_3$): 3.70 (s, 3H); 3.76 (s, 6H); 3.78 (s, 2H); 3.80 (s, 3H); 6.29 (d, 1H, J=3.4 Hz); 6.60 (s, 2H); 6.75 (d, 1H, J=3.4 Hz); 7.07 (t, 1H, J=7.6 Hz); 7.23 (d, 1H, J=7.6 Hz); 7.31 (t, 1H, J=8.0 Hz); 7.37-7.43 (m, 2H); 7.48 (t, 1H, J=7.6 Hz); 7.52 (s, 1H); 7.69 (d, 1H, J=8.0 Hz); 8.45 (d, 1H, J=8.0 Hz).

Step 5:

Dissolve (5-{2-[(3',4',5'-Trimethoxy-biphenyl-2-carbonyl)-amino]-phenyl}-thiophen-2-yl)-acetic acid methyl ester (85) (56 mg, 0.11 mmol) in MeCN (3.8 mL) at rt and add 1M aqu LiOH (76 μL, 0.76 mmol). Stir reaction mixture 18 h at rt. Quench reaction mixture (cooling bath) with 2M aqu. HCl. Extract the mixture with EtOAc (3×), wash the combined organic layer with brine and dry with $Na_2SO_4$ to obtain (5-{2-[(3',4',5'-Trimethoxy-biphenyl-2-carbonyl)-amino]-phenyl}-thiophen-2-yl)-acetic acid (86) (55 mg, 99%) as a brown solid. $^1$H NMR (400 MHz, $CDCl_3$): 3.76 (s, 6H), 3.80 (s, 3H); 3.83 (s, 2H); 6.32 (d, 1H, J=3.5 Hz); 6.60 (s, 2H); 6.78 (d, 1H, J=3.5 Hz); 7.07 (t, 1H, J=7.6 Hz); 7.23 (d, 1H, J=7.6 Hz); 7.32 (t, 1H, J=7.6 Hz); 7.36-7.54 (m, 3H); 7.69 (d, 1H, J=8.0 Hz); 8.43 (d, 1H, J=8.0 Hz).

Step 6:

(The following reaction is done in an anhydrous $N_2$ atmosphere.) Dissolve (5-{2-[(3',4',5'-Trimethoxy-biphenyl-2-carbonyl)-amino]-phenyl}-thiophen-2-yl)-acetic acid (86) (55 mg, 0.11 mmol) in anhydrous DCM (3.2 mL) at −78° C., add dropwise a 1M solution of $BBr_3$ in DCM (730 μL, 0.73 mmol) and stir for additional 30 min at −78° C. After slowly warming up stir the reaction solution for additional 4 h at rt. Cool reaction mixture to 0° C., add dropwise water. Extract the mixture with EtOAc (3×), wash combined organic layer with brine and dry it with $Na_2SO_4$. Purify the crude product by preparative RP HPLC (gradient, water/$CH_3CN$ 95:5 to 5:95) to obtain (5-{2-[(3',4',5'-Trihydroxy-biphenyl-2-carbonyl)-amino]-phenyl}-thiophen-2-yl)-acetic acid (87) (10 mg, 18%) as a yellow solid. $^1$H NMR (400 MHz, $CD_3OD$): 3.88 (s, 2H); 6.50 (s, 2H); 6.66 (d, 1H, J=3.5 Hz); 6.93 (d, 1H, J=3.5 Hz); 7.23 (t; 1H, J=7.3 Hz); 7.35 (t, 1H, J=7.6 Hz); 7.38-7.46 (m, 3H); 7.50 (t, 1H, J=7.3 Hz); 7.62 (d, 1H, J=8.0 Hz); 7.84 (d, 1H, J=8.0 Hz).

EXAMPLE 12

3-{3-[3-(3,4,5-Trihydroxy-phenyl)-propionylamino]-phenylamino}-benzoic acid (92)

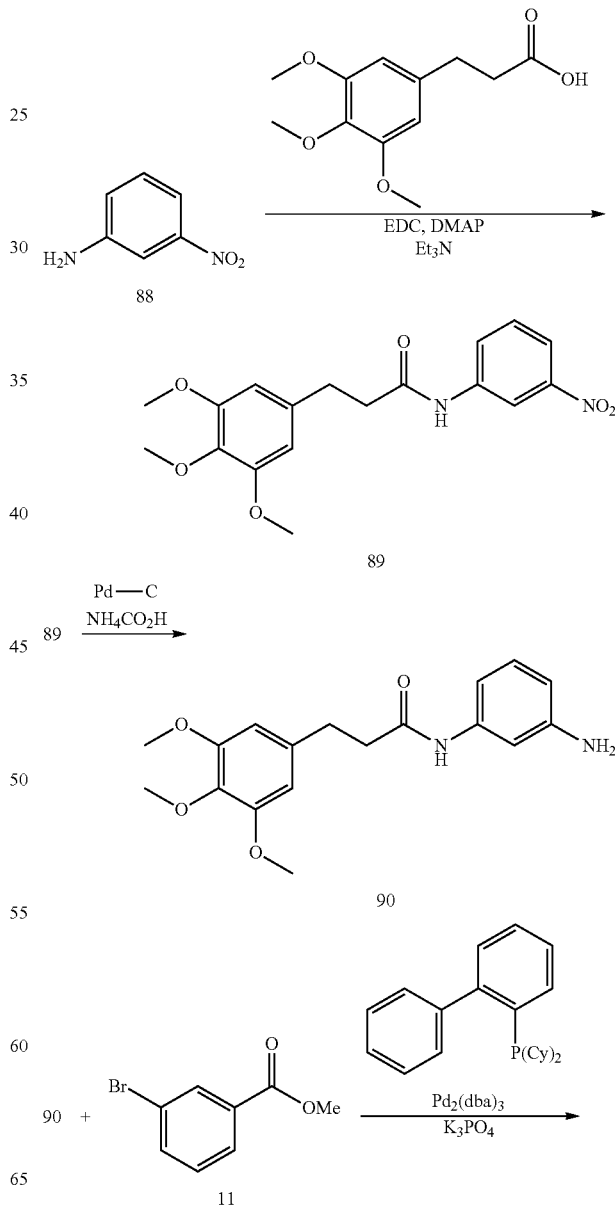

SCHEME 19

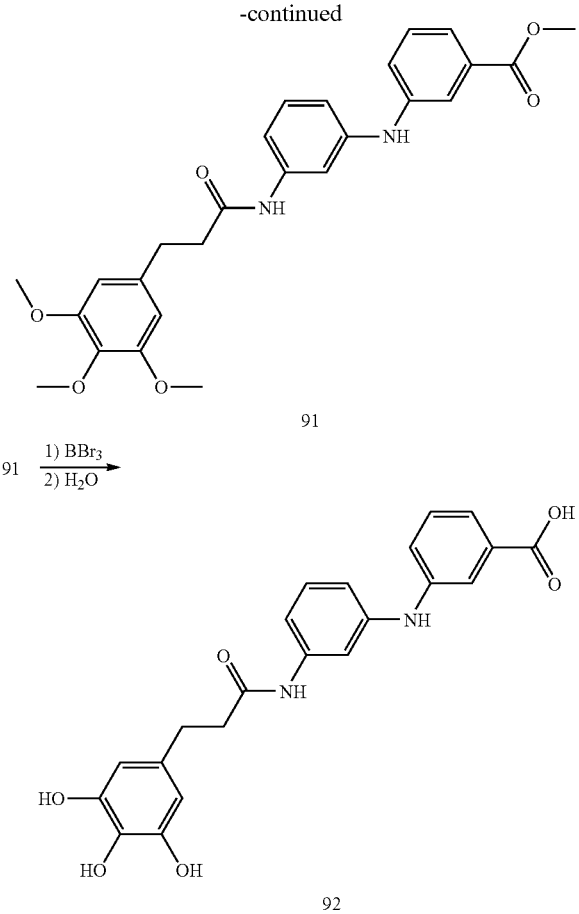

Step 1:
(The following reaction is done in an anhydrous N₂ atmosphere.) Suspend EDCHCl (402 mg, 2.10 mmol) and Et₃N (2934, 2.10 mmol) in anhydrous DCM (17 mL) and stir the resulting solution for 5 min at rt. Add 3-(3,4,5-Trimethoxy-phenyl)-propionic acid (480 mg, 2.00 mmol) and DMAP (24 mg, 0.20 mmol) and stir the resulting solution for 5 min. 3-Nitro-phenylamine (88) (414 mg, 3.00 mmol) and stir the reaction solution 24 h at rt. Quench reaction solution with sat. aqu. NH₄Cl and water, separate layers and extract aqu. layer with EtOAc (3 times). Wash combined organic layer with brine and dry with Na₂SO₄. Purify the crude product by preparative radial chromatography (silica gel, EtOAc/CyH 1+1) to obtain N-(3-Nitro-phenyl)-3-(3,4,5-trimethoxy-phenyl)-propionamide (89) (508 mg, 70%) as a yellow solid. ¹H NMR (400 MHz, CDCl₃): 2.65 (t, 2H, J=7.5 Hz); 2.98 (t, 2H, J=7.5 Hz); 3.79 (s, 6H); 3.81 (s, 3H); 6.42 (s, 2H); 7.41 (s, 1H); 7.45 (t, 1H, J=8.3 Hz); 7.84 (d, 1H, J=8.3 Hz); 7.92 (d, 1H, J=8.3 Hz); 8.31 (s, 1H).

Step 2:
(The following reaction is done in an N₂ atmosphere.) Dissolve N-(3-Nitro-phenyl)-3-(3,4,5-trimethoxy-phenyl)-propionamide (89) (100 mg, 0.28 mmol) in MeOH (4.5 mL) and add Pd on carbon (10% (w/w) Pd content, 29.5 mg, 0.028 mmol) followed by NH₄CO₂H (175 mg, 2.77 mmol) at rt. Degas the reaction mixture carefully (flush with N₂) and stir it for 75 min at rt. Filtrate reaction mixture through a short pad of celite and remove solvent. Treat residue with EtOAc, filtrate again through a short pad of celite and remove solvent to obtain N-(3-Amino-phenyl)-3-(3,4,5-trimethoxy-phenyl)-propionamide (90) (91 mg, 99%) as a white solid. No further purification. ¹H NMR (400 MHz, CD₃OD): 2.65 (t, 2H, J=7.5 Hz); 2.98 (t, 2H, J=7.5 Hz); 3.75 (s, 3H); 3.82 (s, 6H); 6.50 (dd, 1H, J₁=8.0 Hz, J₂=2.0 Hz); 6.58 (s, 2H); 6.80 (dd, 1H, J=8.0 Hz, J₂=2.0 Hz); 7.02-7.07 (m, 1H); 7.04 (t, 1H, J=8.0 Hz).

Step 3:
(The following reaction is done in an anhydrous N₂ atmosphere.) Charge a 2-necked round bottom flask with Pd₂(dba)₃ (5.5 mg, 0.006 mmol), 2-(Dicyclohexylphosphino)biphenyl (2 mg, 0.005 mmol), Methyl-3-bromobenzoate (11) (51 mg, 0.24 mmol) and potassium phosphate (71 mg, 0.33 mmol) and degas it carefully (flush with N₂). Add a solution of N-(3-Amino-phenyl)-3-(3,4,5-trimethoxy-phenyl)-propionamide (90) (91 mg, 0.27 mmol) in dry degassed DME (1.0 mL) and stir the resulting mixture for 15 h at 85° C. Cool the reaction suspension to rt, dilute it with EtOAc, filtrate through a short pad of celite and remove solvent. Purify the crude product preparative radial chromatography (silica gel, EtOAc/CyH 1+1) to obtain 3-{3-[3-(3,4,5-Trimethoxy-phenyl)-propionylamino]-phenylamino-benzoic acid methyl ester (91) (97 mg, 87%) as a yellow solid. ¹H NMR (400 MHz, (CD₃)₂SO): 2.59 (t, 2H, J=7.8 Hz); 2.83 (t, 2H, J=7.8 Hz); 3.60 (s, 3H), 3.72 (s, 6H); 3.82 (s, 3H); 6.54 (s, 2H); 6.75 (d, 1H, J=7.8 Hz); 7.07 (d, 1H, J=8.0 Hz); 7.16 (t, 1H, J=8.0 Hz); 7.29-7.40 (m, 3H); 7.48 (s, 1H), 7.63 (s, 1H); 8.40 (s, 1H); 9.83 (s, 1H).

Step 4:
(The following reaction is done in an anhydrous N₂ atmosphere.) Dissolve 3-{3-[3-(3,4,5-Trimethoxy-phenyl)-propionylamino]-phenylamino-benzoic acid methyl ester (91) (36 mg, 0.08 mmol) in anhydrous DCM (2.3 mL) at −78° C., add dropwise a 1M solution of BBr₃ in DCM (930 μL, 0.93 mmol) and stir for additional 30 min at −78° C. After slowly warming up stir the reaction solution for additional 4 h at rt. Cool reaction mixture to 0° C., add dropwise water/THF (1+1) and remove solvent. Purify the crude product by preparative RP HPLC (gradient, water/CH₃CN 95:5 to 5:95) to obtain 3-{3-[3-(3,4,5-Trihydroxy-phenyl)-propionylamino]-phenylamino}-benzoic acid (92) (10 mg, 33%) as a white solid. ¹H NMR (400 MHz, CD₃OD): 2.60 (t, 2H, J=7.7 Hz); 2.85 (t, 2H, J=7.7 Hz); 6.29 (s, 2H); 6.70 (dd, 1H, J₁=8.0 Hz, J₂=2.0 Hz); 7.06 (d, 1H, J=8.0 Hz), 7.21 (t, 1H, J=8.0 Hz), 7.33-7.37 (m, 2H), 7.45 (m_c, 1H); 7.50-7.54 (m, 1H); 7.77 (s, 1H).

The compounds referred to in the following SCHEME 20 are those compounds referred to as the particularly preferred compounds herein.

SCHEME 20

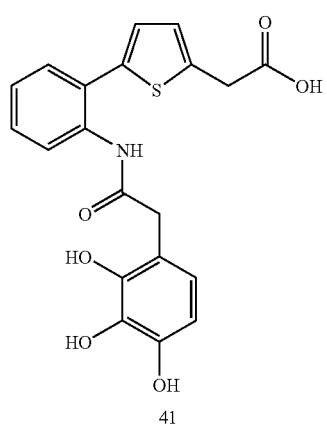

41

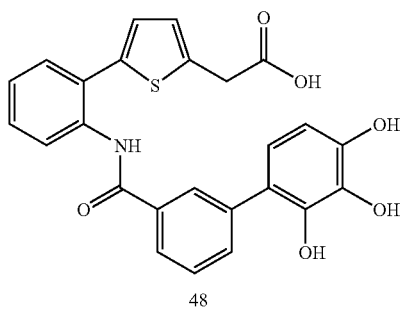
48
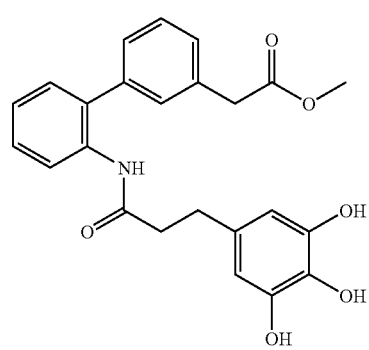
73
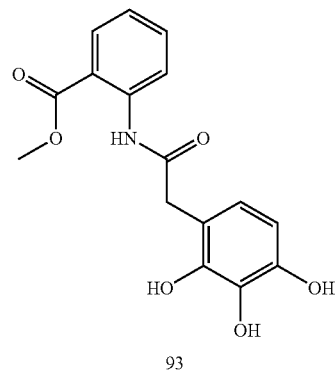
93
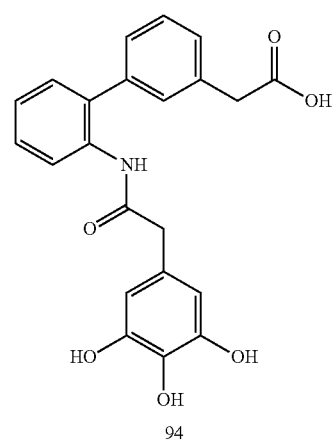
94
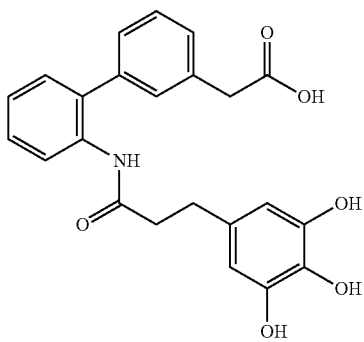
95
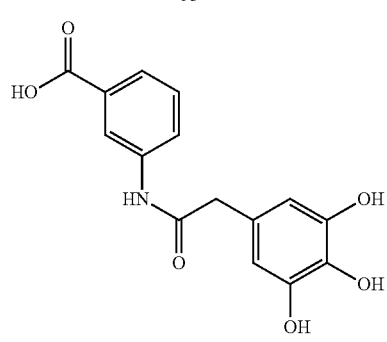
96
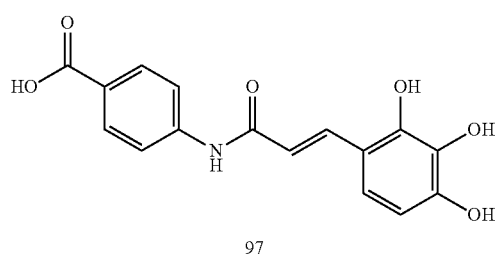
97
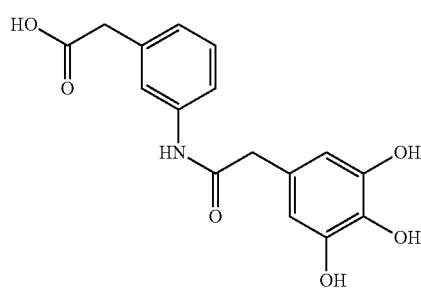
98
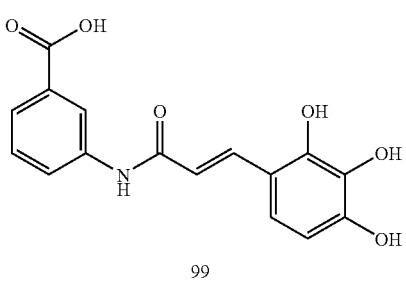
99

-continued
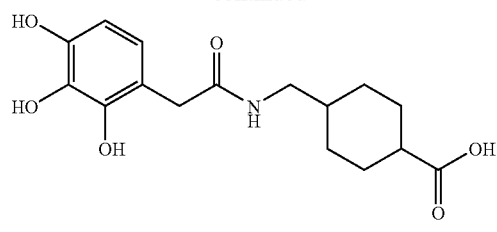
100
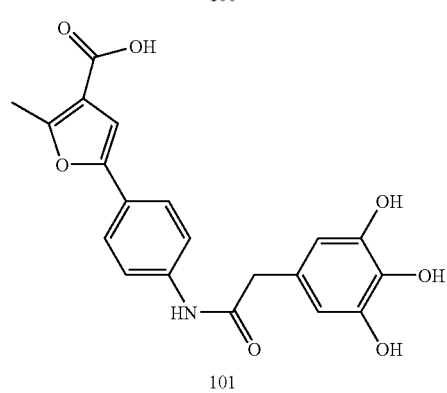
101
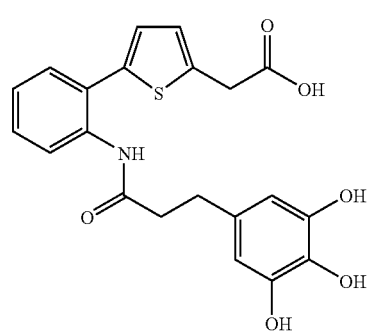
102
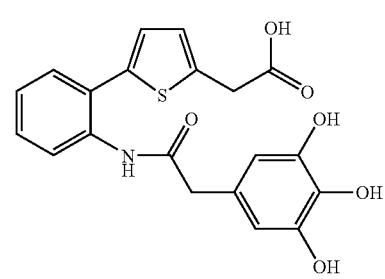
103
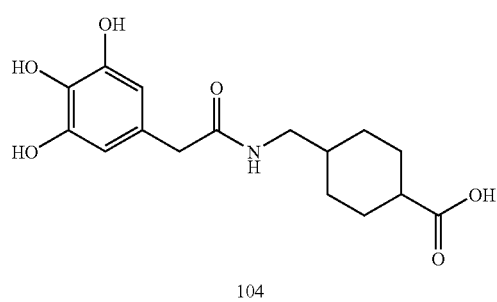
104
-continued
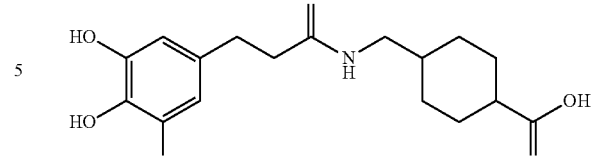
105
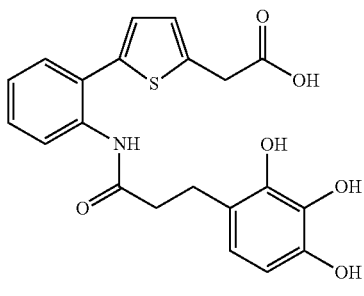
106
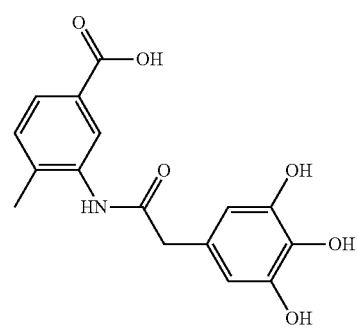
107
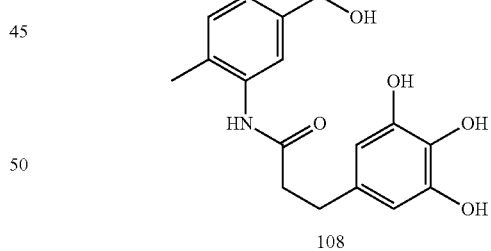
108
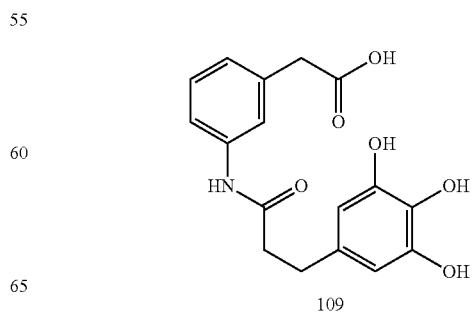
109

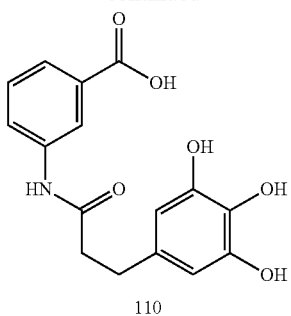
110
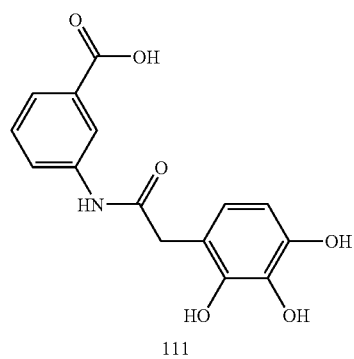
111
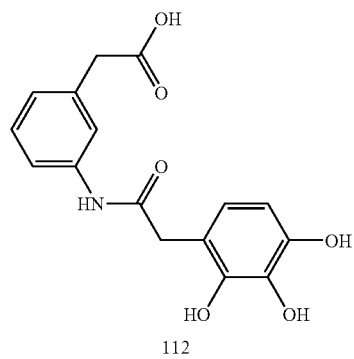
112
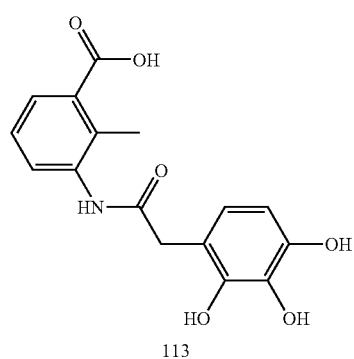
113
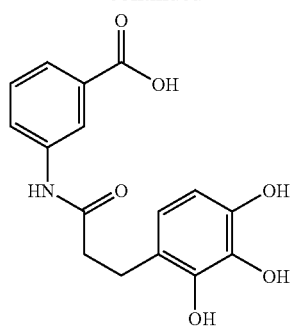
114
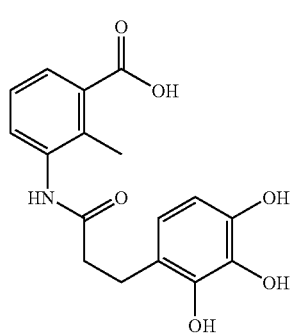
115
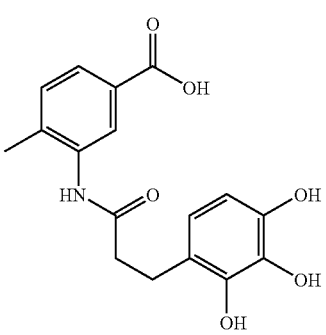
116
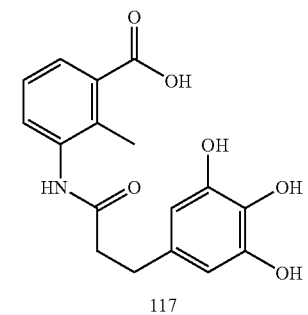
117
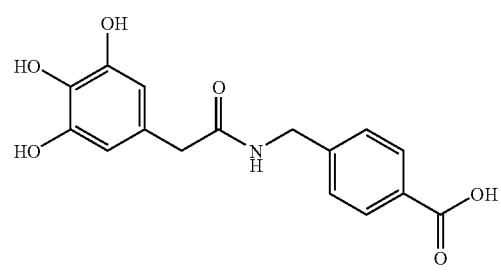
118

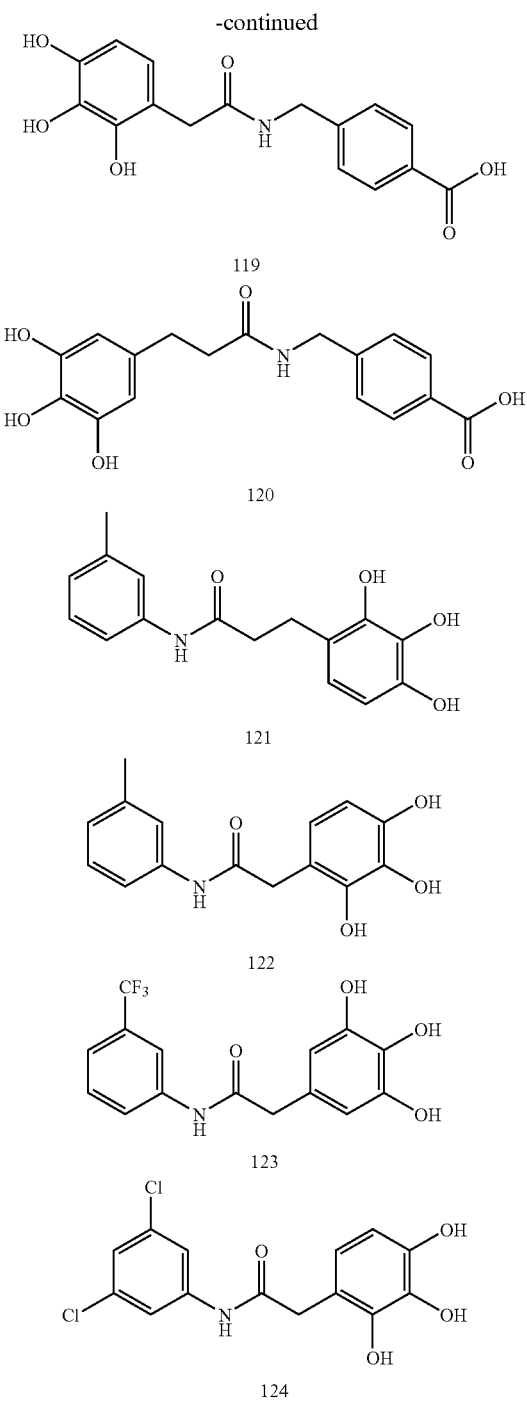

Sialyl Lewis$^x$ Tyrosine Sulfate Assay (sLe$^x$ TSA):

Compounds of the present invention are assayed on a molecular level for their ability to inhibit the binding of P-, L-, or E-selectin chimeric molecules to sLe$^x$ and tyrosinesulfate residues linked to a polymeric matrix as a PSGL-1 substitute. Selected 50% inhibitory concentrations (IC$_{50}$-values) are determined.

Microtiter plates are coated overnight in carbonate buffer pH9.6 with goat anti human Fc mAB (10 µg/ml). After washing in assay buffer (25 mM 4-(2-hydroxyethyl)-1-piperazineethanesulfonic acid (HEPES), 150 mM NaCl, 1 mM CaCl$_2$ pH7.4) and blocking (3% bovine serum albumin (BSA) in assay buffer) plates are incubated for 2 h at 37° C. with human P-Selectin-IgG-chimera (0.61 nM respectively 150 ng/mL) or human L-Selectin-IgG-chimera (0.61 nM respectively 89 ng/mL) or human E-Selectin-IgG-chimera (0.61 nM respectively 131 ng/mL). 5 µl of sLe$^x$-tyrosine sulfate polyacrylamide (1 mg/ml) carrying 15% sLe$^x$, 10% Tyrosine-sulfate and 5% biotin is complexed with 20 µl Streptavidin-Peroxidase solution (1 mg/ml) and 25 µl assay buffer without CaCl$_2$. For use in the assay, the ligand complex is diluted 1:10000 in assay buffer and further diluted 1:1 with varying amounts of compounds in assay buffer incl. 2% DMSO. This mixture is added to the wells precoated with E- or P-selectin. After incubation for 2 h at 37° C., wells are washed for six times with in assay buffer incl. 0.005% Polyoxyethylenesorbitan monolaurate (TWEEN 20), developed for 10-15 min with 20 µl 3,3',5,5'-tetramethylbenzidine (TMB)/H$_2$O$_2$ substrate solution and stopped with 20 µl M H$_2$SO$_4$. Bound sLe$^x$-Tyrosine sulfate ligand complex is determined by measuring optical density at 450 nm vs. 620 nm in a Fusion alpha-FP reader (sold from Packard Bioscience, Dreieich, Germany).

| Table of sLe TSA Data; in vitro-Inhibition of E-/P-/L-Selectin at 100 µM | | | |
|---|---|---|---|
| Compound | E-Selectin [% Inhib.] | P-Selectin [% Inhib.] | L-Selectin [% Inhib.] |
| 41 | 46 | 92 | 81 |
| 48 | 31 | 97 | 95 |
| 73 | 54 | 84 | 88 |
| 93 | 20 | 68 | 63 |
| 94 | 79 | 78 | 76 |
| 95 | 89 | 90 | 81 |
| 96 | 63 | 86 | 73 |
| 97 | 51 | 97 | 98 |
| 98 | 58 | 57 | 52 |
| 99 | 71 | 99 | 99 |
| 100 | 21 | 40 | 27 |
| 101 | 50 | 93 | 95 |
| 102 | 99 | 97 | 96 |
| 103 | 68 | 87 | 81 |
| 104 | 67 | 67 | 62 |
| 105 | 90 | 86 | 84 |
| 106 | 52 | 94 | 85 |
| 107 | 53 | 87 | 75 |
| 108 | 85 | 86 | 84 |
| 109 | 82 | 73 | 72 |
| 110 | 96 | 96 | 92 |
| 111 | 46 | 99 | 97 |
| 112 | 38 | 97 | 83 |
| 113 | 42 | 73 | 48 |
| 114 | 38 | 99 | 95 |
| 115 | n.a. | 89 | 88 |
| 116 | 92 | 88 | 87 |
| 117 | 94 | 86 | 89 |
| 118 | 53 | 79 | 66 |
| 119 | 14 | 82 | 55 |
| 120 | 92 | 88 | 87 |
| 121 | 29 | 73 | 77 |
| 122 | 70 | 81 | 87 |

| Results from sLe$^x$TSA: IC$_{50}$ Data for E-/P-/L-Selectin | | | |
|---|---|---|---|
| Compound | IC$_{50}$ E-Selectin [µM] | IC$_{50}$ P-Selectin [µM] | IC$_{50}$ L-Selectin [µM] |
| 41 | — | 7.6 | 14.6 |
| 48 | 132 | 5.8 | 9.8 |
| 94 | 4.9 | 4.2 | 8.7 |
| 96 | 0.8 | 1.1 | 1.4 |
| 97 | 285 | 3.5 | 6.2 |

-continued

Results from sLe$^x$TSA: IC$_{50}$ Data for E-/P-/L-Selectin

| Compound | IC$_{50}$ E-Selectin [μM] | IC$_{50}$ P-Selectin [μM] | IC$_{50}$ L-Selectin [μM] |
|---|---|---|---|
| 98 | 1.0 | 2.1 | — |
| 99 | — | 14.4 | 24.9 |
| 102 | 3.3 | 2.4 | 3.1 |
| 104 | 3.0 | 2.8 | 3.3 |
| 105 | 3.1 | 3.4 | 5.7 |
| 108 | 1.3 | 1.7 | 1.8 |
| 109 | 2.3 | 2.3 | 2.3 |
| 111 | 0.6 | 2.1 | 7.0 |
| 112 | — | 7.4 | 16.0 |
| 116 | 7.3 | 13.0 | 15.0 |
| 117 | 8.4 | 21.7 | 109 |
| 118 | 8.7 | 14.8 | 26.2 |
| 120 | 8.4 | 34.9 | 30.8 |

Flow Chamber Assay/Cell Adhesion and Rolling Under Flow Conditions

To assess the capability of compounds to inhibit cell binding under dynamic conditions resembling the flow in a blood vessel, flow chamber assays addressing/testing binding of HL-60 cells/various cell lines to P-selectin, L-selectin and E-selectin chimeric molecules are performed.

Cell attachment under flow conditions are determined using a parallel flow chamber system. A 35 mm polystyrene culture dish is coated for 1 hour at room temperature with coating buffer (50 mM tris-(hydroxymethyl)aminomethane buffer (Tris), 150 mM NaCl, 2 mM CaCl$_2$; pH 7,4) containing human E- or P-selectin-IgG chimera at concentrations of 2.5 μg/ml or 10 μg/ml, respectively. After removal of the coating solution non specific binding sites are blocked for an additional hour with 1% BSA in coating buffer at room temperature. After washing with assay buffer ("Roswell Park Memorial Institute 1640" (RPMI 1640)+10 mM HEPES) the dish is fitted into a parallel plate laminar flow chamber (sold from Glycotech, Rockville, Md.) and mounted on an inverted phase-contrast microscope (sold from Olympus, Hamburg, Germany) equipped with a CCD camera (JVC) that is connected to a PC. Employing a peristaltic pump (sold from Ismatec, Wertheim-Mondfeld, Germany) the re-circulating system is equilibrated with assay buffer containing 125 μM compound or vehicle control (DMSO). Cells (1 million/ml) are added to the chamber and allowed to distribute for 2 minutes at a high flow rate. The flow rate is then decreased resulting in a calculated flow shear of 1 dyne/cm$^2$. Video sequences of 10 low power fields are digitally recorded after 5 minutes continuous flow. The percentage of inhibition is calculated from the mean number of cells per field that attached to the coated dish surface in the presence versus absence of compound of at independent experiments.

Data from Flow Chamber Assay for E- and P-Selectin

| Compound | E-Selectin [% Inhib.] | P-Selectin [% Inhib.] |
|---|---|---|
| 41 | 26 | — |
| 48 | 61 | 55 |
| 97 | — | 47 |
| 99 | 28 | 96 |
| 101 | — | 99 |
| 102 | 35 | 11 |
| 108 | n.a. | 17 |
| 118 | 16 | 20 |
| 120 | 21 | 21 |
| 121 | 18 | 44 |
| 122 | 27 | 22 |
| 123 | 51 | — |
| 124 | 28 | 23 |

Parallel Artificial Membrane Permeation Assay (PAMPA)

The test compounds are dissolved at 10 mM in DMSO and diluted to 500 μM with PBS pH 7.4 or pH 4.0, respectively resulting in 'donor solutions'. For use as an artificial membrane, a 1% solution of lecithin (w/v) in dodecane is prepared and sonicated. Then, 5 μl of the lecithin/dodecane mixture are carefully pipetted into each donor plate well. Immediately after the application of the artificial membrane, 150 μl of drug containing donor solutions are added to each well of the donor plate. Each well of the acceptor plate is filled with 300 μl buffer (PBS with 5% DMSO at pH 7.4 or pH 4.0, respectively) and the drug-filled donor plate is placed onto the acceptor plate, making sure the membrane is in contact with the buffer. After replacement of the lid, the assembled plates are transferred into a sealed box equipped with a moistured towel and incubated at room temperature for 16 hours. Then, the wells of the acceptor plate are analyzed with LC/MS.

Data from PAMPA

| Compound | [% flux] at pH 4.0 | [% flux] at pH 7.4 |
|---|---|---|
| 93 | 0 | 17 |
| 97 | 0 | 16 |
| 118 | 0 | 1 |
| 121 | 12 | 12 |
| 122 | 6 | 0 |
| 123 | 27 | 0 |
| 124 | 100 | 0 |

The invention claimed is:

1. A pharmaceutical composition comprising at least one compound of formula (C) or (D) and a pharmaceutically acceptable carrier which is useful in a medicine

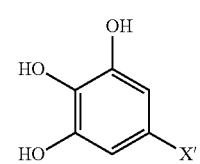

C

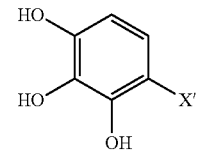

D wherein —X' is

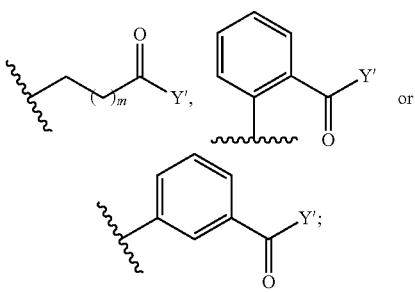

m is 0 or 1;
Y' is

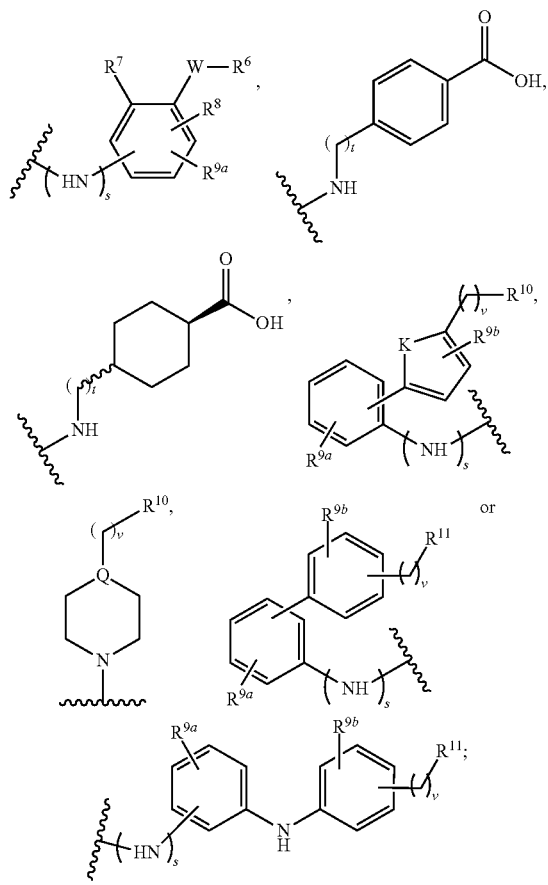

Q is CH or N;
K is S or O;
v is 0, 1, or 2;
$R^6$ is $CO_2H$, $CO_2Alkyl$, $CO_2Aryl$, $CO_2NH_2$, $CO_2Aralkyl$, $SO_3H$, $SO_2NH_2$, $PO(OH)_2$, 1-H-tetrazolyl, CHO, $COCH_3$, $CH_2OH$, $NH_2$, NHAlkyl, N(Alkyl)Alkyl', $OCH_3$, $CH_2OCH_3$, SH, F, Cl, Br, I, $CH_3$, $CH_2CH_3$, CN, or $CF_3$;
$R^7$, independently from $R^6$, is H, $CH_3$, $CH_2CH_3$, $CF_3$, F, Cl, Br, I, CN, or $NO_2$;
$R^8$, independently from $R^6$ and $R^7$, is H, $CH_3$, $CH_2CH_3$, $CF_3$, F, Cl, Br, I, CN, $NO_2$, or $R^6$;
$R^{9a}$ is H, $NO_2$, $CF_3$, F, Cl, Br, I, CN, $CH_3$, $OCH_3$, SH, or $NH_2$;
$R^{9b}$, independently from $R^{9a}$, is H, $NO_2$, $CF_3$, F, Cl, Br, I, CN, $CH_3$, $OCH_3$, SH, or $NH_2$;
$R^{10}$ is $CO_2H$, $CO_2alkyl$, $CO_2aryl$, $CO_2NH_2$, $CO_2aralkyl$, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2NHalkyl$, $CH_2N(alkyl)alkyl'$, $CH_2OCH_3$, or $CH_2SH$;
$R^{11}$ is $CO_2H$, $CO_2alkyl$, $CO_2aryl$, $CO_2NH_2$, $CO_2aralkyl$, $SO_3H$, $SO_2NH_2$, $PO(OH)_2$, 1-H-tetrazolyl, CHO, $COCH_3$, OH, $NH_2$, NHalkyl, N(alkyl)alkyl', $OCH_3$, or SH;
s is 1;
t is 0, 1, or 2;
—W— is $—(CH_2—)_v$, cis-CH=CH— or trans-CH=CH—, and v is 0, 1, or 2;
in case that $R^6$ is $NH_2$, $R^7$ or $R^8$ or $R^{9a}$ must not be H; and
in case that —W— is cis-CH=CH— or trans-CH=CH—, $R^6$ must not be $NH_2$ or SH;
or the pharmaceutically acceptable salts, esters, or amides of the compounds of formula (C) or (D).

2. A pharmaceutical composition of claim 1 wherein the at least one compound is a compound of formula (C).

3. A pharmaceutical composition of claim 1 wherein the at least one compound is a compound of formula (D).

4. A method of inhibiting the binding of P-selectin, L-selectin or E-selectin to $sLe^x$ or $sLe^a$ and tyrosinesulfate residues in a patient comprising the administration of a compound having the structure of formula (C) or (D) as defined in claim 1.

5. A chemical compound of the formula (C) or (D)

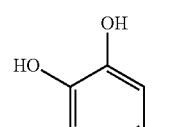
C

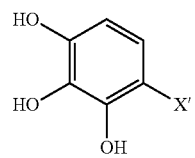
D wherein —X' is

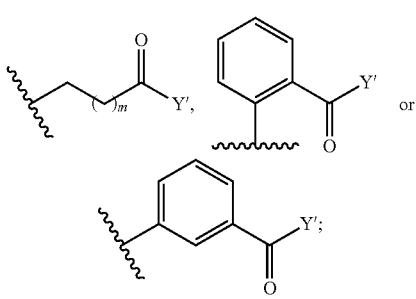

m is 0 or 1;

Y' is

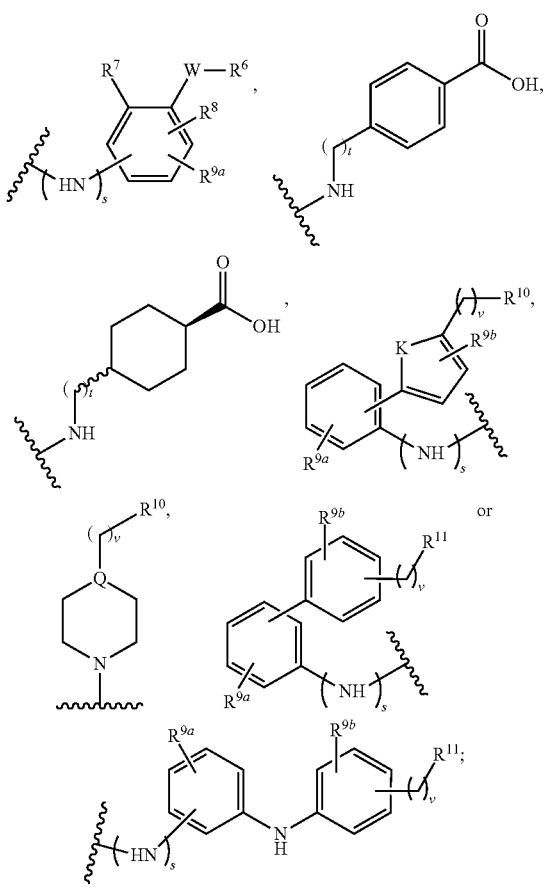

Q is CH or N;
K is S or O;
v is 0, 1, or 2;

$R^6$ is $CO_2H$, $CO_2$Alkyl, $CO_2$Aryl, $CO_2NH_2$, $CO_2$Aralkyl, $SO_3H$, $SO_2NH_2$, $PO(OH)_2$, 1-H-tetrazolyl, CHO, $COCH_3$, $CH_2OH$, $NH_2$, NHAlkyl, N(Alkyl)Alkyl', $OCH_3$, $CH_2OCH_3$, SH, F, Cl, Br, I, $CH_3$, $CH_2CH_3$, CN, or $CF_3$;

$R^7$, independently from $R^6$, is H, $CH_3$, $CH_2CH_3$, $CF_3$, F, Cl, Br, I, CN, or $NO_2$;

$R^8$, independently from $R^6$ and $R^7$, is H, $CH_3$, $CH_2CH_3$, $CF_3$, F, Cl, Br, I, CN, $NO_2$, or $R^6$;

$R^{9a}$ is H, $NO_2$, $CF_3$, F, Cl, Br, I, CN, $CH_3$, $OCH_3$, SH, or $NH_2$;

$R^{9b}$, independently from $R^{9a}$, is H, $NO_2$, $CF_3$, F, Cl, Br, I, CN, $CH_3$, $OCH_3$, SH, or $NH_2$;

$R^{10}$ is $CO_2H$, $CO_2$alkyl, $CO_2$aryl, $CO_2NH_2$, $CO_2$aralkyl, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2$NHalkyl, $CH_2$N(alkyl)alkyl', $CH_2OCH_3$, or $CH_2SH$;

$R^{11}$ is $CO_2H$, $CO_2$alkyl, $CO_2$aryl, $CO_2NH_2$, $CO_2$aralkyl, $SO_3H$, $SO_2NH_2$, $PO(OH)_2$, 1-H-tetrazolyl, CHO, $COCH_3$, OH, $NH_2$, NHalkyl, N(alkyl)alkyl', $OCH_3$, or SH;

s is 1;

t is 0, 1, or 2;

—W— is —$(CH_2)_v$—, cis-CH=CH— or trans-CH=CH—, and v is 0, 1, or 2;

in case that $R^6$ is $NH_2$, $R^7$ or $R^8$ or $R^{9a}$ must not be H; and in case that —W— is cis-CH=CH— or trans-CH=CH—, $R^6$ must not be $NH_2$ or SH;

or a pharmaceutically acceptable salt, ester, or amide of the above identified compound of formula (C) or (D).

6. The chemical compound of claim 5, wherein the compound is of formula (C) and all variables, indices, symbols, and substituents are as defined in 5, or a pharmaceutically acceptable salt, ester, or amide of the above identified compound of formula (C).

7. The chemical compound of claim 5, wherein the compound is of formula (D) and all variables, indices, symbols, and substituents are as defined in 5, or a pharmaceutically acceptable salt, ester, or amide of the above identified compound of formula (D).

* * * * *